(12) United States Patent
Chiba et al.

(10) Patent No.: US 8,729,240 B2
(45) Date of Patent: May 20, 2014

(54) MONOCLONAL ANTIBODY AGAINST OXIDIZED LOW-DENSITY LIPOPROTEIN

(75) Inventors: Hitoshi Chiba, Sapporo (JP); Seiichi Kobayashi, Sapporo (JP); Hiroyuki Furukawa, Sapporo (JP)

(73) Assignee: National University Corporation Hokkaido University, Hokkaido (JP)

( * ) Notice: Subject to any disclaimer, the term of this patent is extended or adjusted under 35 U.S.C. 154(b) by 0 days.

(21) Appl. No.: 13/695,043

(22) PCT Filed: Apr. 28, 2011

(86) PCT No.: PCT/JP2011/060376
§ 371 (c)(1),
(2), (4) Date: Dec. 19, 2012

(87) PCT Pub. No.: WO2011/136332
PCT Pub. Date: Nov. 3, 2011

(65) Prior Publication Data
US 2013/0253174 A1    Sep. 26, 2013

(30) Foreign Application Priority Data
Apr. 28, 2010   (JP) .................................. 2010-103663

(51) Int. Cl.
*C07K 16/00*    (2006.01)
(52) U.S. Cl.
USPC .................................................... 530/388.25
(58) Field of Classification Search
CPC ................................ A61K 51/10; C07K 16/18
See application file for complete search history.

(56) References Cited

U.S. PATENT DOCUMENTS 5,196,324 A      3/1993   Bumol et al.
7,959,923 B2 *   6/2011   You et al. ................... 424/155.1

FOREIGN PATENT DOCUMENTS

JP    4-159300 A    6/1992
JP    09-005323    1/1997

OTHER PUBLICATIONS

Rudikoff et al Proc Natl Acad Sci USA 79: 1979, 1982.*
Barrios et al J Molecular Recognition 17: 332-338, 2004.*
MacCallum et al Mol. Biol 262: 732-745, 1996.*
Pascalis et al The Journal of Immunology 169: 3076-3084, 2002.*
Paul, Fundamental Immunology, 3rd Edition, 1993, pp. 292-295, under the heading "Fv Structure and Diversity in Three Dimensions".*
Abe, The Saitama Journal of Medical Technology, 56(2):240-41 (2009) (w/ English abstract).
H. Chiba et al., J. Lipid Research, 38:1204-16 (1997).
Kozbor et al., Monoclonal Antibodies and Cancer Therapy, Alan R. Liss, Inc., 77-96 (1985).
Hirano et al., J. Atherosclerosis and Thrombosis, 12(2): 67-72 (2005).
Hui et al., Lipids 38(12):1287-92 (2003).
Itabe et al., J. Biological Chemistry, 269(21): 15274-79 (1994).
Köhler and Milstein, Nature, 256(5517):495-7 (1975).
Kotani et al., Biochimica et Biophysica Acta, 1215:121-25 (1994).
Kotani et al., Rinsho Byouri (Clinical Pathology), 45(1):47-54 (1997).
Kozbor and Roder, Immunology Today, 4(3):72-79 (1983).
Nagasaka, et al., J. Pediatri., 146(3):329-35 (2005).
International Search Report for International Application No. PCT/JP2011/060376 mailed Jun. 28, 2011 by Japanese Patent Office.

* cited by examiner

*Primary Examiner* — Shulamith H Shafer
(74) *Attorney, Agent, or Firm* — RatnerPrestia

(57) ABSTRACT

Provided is a monoclonal antibody against slightly oxidized LDL, which can play a role as an important tool in the research and development of oxidized LDL. Also provided are a kit for the simple detection of slightly oxidized LDL and a method for the simple detection of slightly oxidized LDL from the biological sample of a subject to be tested which use the monoclonal antibody. By means of ELISA (Enzyme-Linked Immunosorbent Assay) using the monoclonal antibody as the solid phase antibody and an anti-apolipoprotein B antibody as the detection antibody, the degree of reaction between a severely oxidized low-density lipoprotein and the monoclonal antibody is low in comparison to the degree of reaction between a slightly oxidized low-density lipoprotein and the monoclonal antibody, and the monoclonal antibody specifically reacts with an oxidized low-density lipoprotein.

9 Claims, 23 Drawing Sheets

Sequence Having the Highest Homology with G11-6-VH

```
>gb|ADM43408.1| immunoglobulin heavy chain variable region [Mus musculus]
Length=117

Score =  223 bits (569),  Expect = 5e-57, Method: Compositional matrix adjust.
Identities = 112/116 (97%), Positives = 112/116 (97%), Gaps = 1/116 (0%)

Query  1    VQLQQSGTVLARPGASVKMSCKASGYTFTSYWMHWVKQRPGQGLEWIGAIYPGNSDTSYN    60  (SEQ ID NO: 16)
            VQLQQSGTVLARPGASVKMSCKASGYTFTSYWMHWVKQRPGQGLEWIGAIYPGNSDTSYN      (SEQ ID NO: 17)
Sbjct  2    VQLQQSGTVLARPGASVKMSCKASGYTFTSYWMHWVKQRPGQGLEWIGAIYPGNSDTSYN    61  (SEQ ID NO: 18)

Query  61   QKFKGKAKLTAVTSTSTAYMELSSLTNEDSAVYYCTR-VYGRAMDYWGQGTSVTVS       115 (SEQ ID NO: 16)
            QKFKGKAKLTAVTSTSTAYMELSSLTNEDSAVYYCTR Y  AMDYWGQGTSVTVS           (SEQ ID NO: 17)
Sbjct  62   QKFKGKAKLTAVTSTSTAYMELSSLTNEDSAVYYCTRGNYYYAMDYWGQGTSVTVS       117 (SEQ ID NO: 18)
```

Sequence Having the Highest Homology with G11-6-VL

```
>gb|ABL61283.1| polyreactive immunoglobulin light chain VJ region [Mus musculus]
 gb|ABL61284.1| polyreactive immunoglobulin light chain VJ region [Mus musculus]
 gb|ACV40679.1| anti-chloramphenicol immunoglobulin kappa light chain variable
region [Mus musculus]
 gb|ACV40680.1| anti-chloramphenicol immunoglobulin kappa light chain variable
region [Mus musculus]
Length=108

Score =  224 bits (570),  Expect = 4e-57, Method: Compositional matrix adjust.
Identities = 108/108 (100%), Positives = 108/108 (100%), Gaps = 0/108 (0%)

Query  1    DIVLTQSPASLAVSLGQRATISYRASKSVSTSGYSYMHWNQQKPGQPPRLLIYLVSNLES    60  (SEQ ID NO: 19)
            DIVLTQSPASLAVSLGQRATISYRASKSVSTSGYSYMHWNQQKPGQPPRLLIYLVSNLES      (SEQ ID NO: 20)
Sbjct  1    DIVLTQSPASLAVSLGQRATISYRASKSVSTSGYSYMHWNQQKPGQPPRLLIYLVSNLES    60  (SEQ ID NO: 21)

Query  61   GVPARFSGSGSGTDFTLNIHPVEEEDAATYYCQHIRELTRSEGGPSWK               108 (SEQ ID NO: 19)
            GVPARFSGSGSGTDFTLNIHPVEEEDAATYYCQHIRELTRSEGGPSWK                   (SEQ ID NO: 20)
Sbjct  61   GVPARFSGSGSGTDFTLNIHPVEEEDAATYYCQHIRELTRSEGGPSWK               108 (SEQ ID NO: 21)
```

Figure 4

Sequence Having the Highest Homology with CDR1 of G11-6-VH

```
>gb|AEB00239.1| immunoglobulin mu heavy chain [Homo sapiens]
Length=158

Score =  24.0 bits (49),    Expect = 1441
Identities = 5/5 (100%),    Positives = 5/5 (100%),  Gaps = 0/5 (0%)

Query   1   SYWMH    5    ( SEQ ID NO: 22 )
            SYWMH         ( SEQ ID NO: 23 )
Sbjct  31   SYWMH   35    ( SEQ ID NO: 24 )
```

Sequence Having the Highest Homology with CDR2 of G11-6-VH

```
>gb|ADM43414.1| immunoglobulin heavy chain variable region [Mus musculus]
Length=117

Score =  57.5 bits (128),   Expect = 2e-07
Identities = 17/17 (100%),  Positives = 17/17 (100%), Gaps = 0/17 (0%)

Query   1   AIYPGNSDTSYNQKFKG   17   ( SEQ ID NO: 25 )
            AIYPGNSDTSYNQKFKG        ( SEQ ID NO: 26 )
Sbjct  50   AIYPGNSDTSYNQKFKG   66   ( SEQ ID NO: 27 )
```

Figure 5

Sequence Having the Highest Homology with CDR3 of G11-6-VH

>dbj|BAH47826.1| immunoglobulin heavy chain [Mus musculus]
Length=114

Score = 28.2 bits (59), Expect = 122
Identities = 7/7 (100%), Positives = 7/7 (100%), Gaps = 0/7 (0%)

Query  2    YGRAMDY    8      (SEQ ID NO: 28)
            YGRAMDY           (SEQ ID NO: 29)
Sbjct  101  YGRAMDY    107    (SEQ ID NO: 30)

Sequence Having the Highest Homology with CDR1 of G11-6-VL

>gb|ADJ00222.1| anti-furazolidone metabolite single-chain variable fragment antibody [synthetic construct]
Length=248

Score = 50.3 bits (111), Expect = 3e-05
Identities = 15/15 (100%), Positives = 15/15 (100%), Gaps = 0/15 (0%)

Query  1    RASKSVSTSGYSYMH    15     (SEQ ID NO: 31)
            RASKSVSTSGYSYMH           (SEQ ID NO: 32)
Sbjct  161  RASKSVSTSGYSYMH    175    (SEQ ID NO: 33)

Figure 6

Sequence Having the Highest Homology with CDR2 of G11-6-VL

```
>ref|ZP_08168462.1| conserved domain protein [Turicibacter sp. HGF1]
 gb|EGC91218.1| conserved domain protein [Turicibacter sp. HGF1]
Length=328

Score = 24.0 bits (49),  Expect = 2017
 Identities = 7/7 (100%), Positives = 7/7 (100%), Gaps = 0/7 (0%)

Query  1    LVSNLES  7      ( SEQ ID NO: 34 )
            LVSNLES         ( SEQ ID NO: 35 )
Sbjct  237  LVSNLES  243    ( SEQ ID NO: 36 )
```

Sequence Having the Highest Homology with CDR3 of G11-6-VL

```
>gb|AEA69713.1| putative glycosylase [Pseudomonas brassicacearum subsp. brassicacearum
NFM421]
Length=366

Score = 26.5 bits (55),  Expect = 346
 Identities = 7/7 (100%), Positives = 7/7 (100%), Gaps = 0/7 (0%)

Query  1    QHIRELT  7      ( SEQ ID NO: 37 )
            QHIRELT         ( SEQ ID NO: 38 )
Sbjct  331  QHIRELT  337    ( SEQ ID NO: 39 )
```

Figure 7

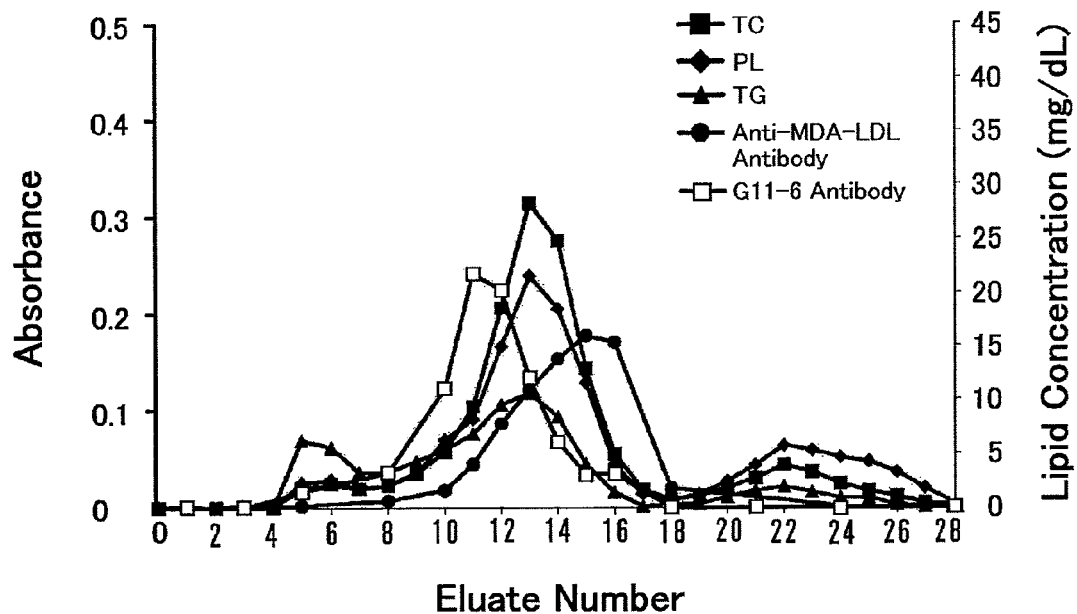
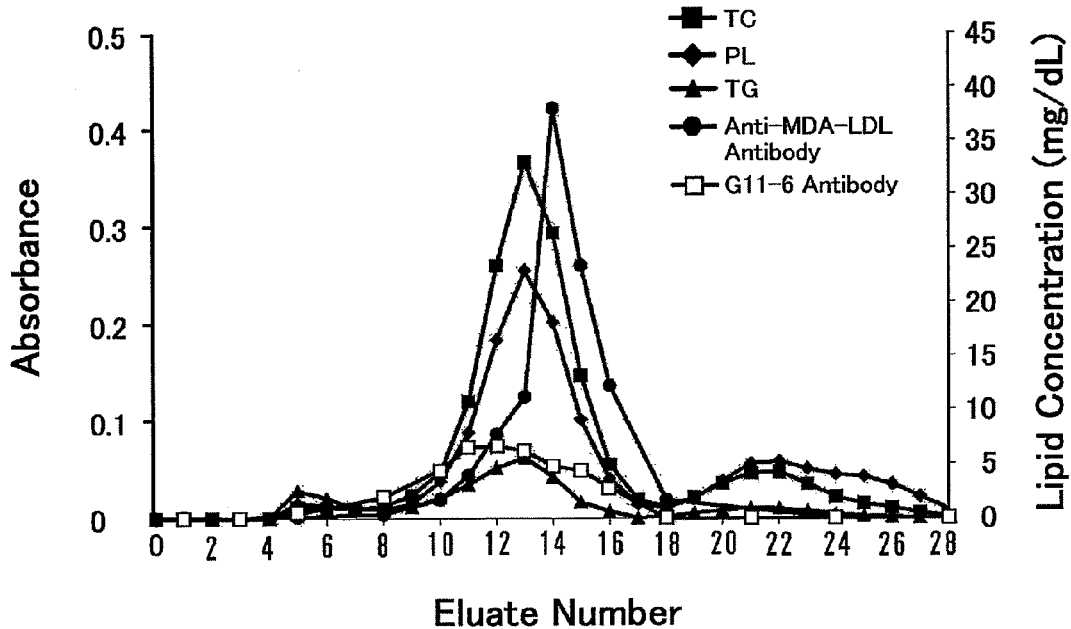
Figure 15

SEQUENCE LISTING

<160> NUMBER OF SEQ ID NOS: 39

<210> SEQ ID NO 1
<211> LENGTH: 34
<212> TYPE: DNA
<213> ORGANISM: Artificial Sequence
<220> FEATURE:
<223> OTHER INFORMATION: 5' primer
<220> FEATURE:
<221> NAME/KEY: misc_feature
<223> OTHER INFORMATION: R is adenine(A) or guanine(G).S is cytosine(C)

-continued or guanine(G).Y is cytosine(C) or thymine(T).W is adenine(A) or thymine(T).

<400> SEQUENCE: 1
gggaattcat graatgsasc tgggtywtyc tctt                          34

<210> SEQ ID NO 2
<211> LENGTH: 32
<212> TYPE: DNA
<213> ORGANISM: Artificial Sequence
<220> FEATURE:
<223> OTHER INFORMATION: 3' primer

<400> SEQUENCE: 2
cccaagctta cgagggggaa gacatttggg aa                            32

<210> SEQ ID NO 3
<211> LENGTH: 33
<212> TYPE: DNA
<213> ORGANISM: Artificial Sequence
<220> FEATURE:
<223> OTHER INFORMATION: 5' primer

<400> SEQUENCE: 3
gggaattcat ggagacagac acactcctgc tat                           33

<210> SEQ ID NO 4
<211> LENGTH: 30
<212> TYPE: DNA
<213> ORGANISM: Artificial Sequence
<220> FEATURE:
<223> OTHER INFORMATION: 3' primer

<400> SEQUENCE: 4
cccaagctta ctggatggtg ggaagatgga                               30

<210> SEQ ID NO 5
<211> LENGTH: 20
<212> TYPE: DNA
<213> ORGANISM: Artificial Sequence
<220> FEATURE:
<223> OTHER INFORMATION: T3 primer

<400> SEQUENCE: 5
attaaccctc actaaaggga                                          20

<210> SEQ ID NO 6
<211> LENGTH: 348
<212> TYPE: DNA
<213> ORGANISM: Mus musculus
<220> FEATURE:
<221> NAME/KEY: CDS
<222> LOCATION: (1)..(348)

<400> SEQUENCE: 6

```
gtt cag ctc cag cag tct ggg act gtg ctg gca agg cct ggg gct tca      48
Val Gln Leu Gln Gln Ser Gly Thr Val Leu Ala Arg Pro Gly Ala Ser
1               5                   10                  15 gtg aag atg tcc tgc aag gct tct ggc tac acc ttt acc agc tac tgg      96
Val Lys Met Ser Cys Lys Ala Ser Gly Tyr Thr Phe Thr Ser Tyr Trp
            20                  25                  30 atg cac tgg gta aaa cag agg cct gga cag ggt ctg gaa tgg att ggc     144
Met His Trp Val Lys Gln Arg Pro Gly Gln Gly Leu Glu Trp Ile Gly
        35                  40                  45
```

```
gct att tat cct gga aat agt gat act agc tac aac cag aag ttc aag    192
Ala Ile Tyr Pro Gly Asn Ser Asp Thr Ser Tyr Asn Gln Lys Phe Lys
 50                  55                  60 ggc aag gcc aaa ctg act gca gtc aca tcc acc agc act gcc tac atg    240
Gly Lys Ala Lys Leu Thr Ala Val Thr Ser Thr Ser Thr Ala Tyr Met
 65                  70                  75                  80 gag ctc agc agc ctg aca aat gag gac tct gcg gtc tat tac tgt aca    288
Glu Leu Ser Ser Leu Thr Asn Glu Asp Ser Ala Val Tyr Tyr Cys Thr
                 85                  90                  95 aga gtc tac ggt agg gct atg gac tac tgg ggt caa gga acc tca gtc    336
Arg Val Tyr Gly Arg Ala Met Asp Tyr Trp Gly Gln Gly Thr Ser Val
            100                 105                 110 acc gtc tcc tca                                                    348
Thr Val Ser Ser
        115

<210> SEQ ID NO 7
<211> LENGTH: 116
<212> TYPE: PRT
<213> ORGANISM: Mus musculus

<400> SEQUENCE: 7

Val Gln Leu Gln Gln Ser Gly Thr Val Leu Ala Arg Pro Gly Ala Ser
 1               5                  10                  15

Val Lys Met Ser Cys Lys Ala Ser Gly Tyr Thr Phe Thr Ser Tyr Trp
                20                  25                  30

Met His Trp Val Lys Gln Arg Pro Gly Gln Gly Leu Glu Trp Ile Gly
             35                  40                  45

Ala Ile Tyr Pro Gly Asn Ser Asp Thr Ser Tyr Asn Gln Lys Phe Lys
 50                  55                  60

Gly Lys Ala Lys Leu Thr Ala Val Thr Ser Thr Ser Thr Ala Tyr Met
 65                  70                  75                  80

Glu Leu Ser Ser Leu Thr Asn Glu Asp Ser Ala Val Tyr Tyr Cys Thr
                 85                  90                  95

Arg Val Tyr Gly Arg Ala Met Asp Tyr Trp Gly Gln Gly Thr Ser Val
            100                 105                 110

Thr Val Ser Ser
        115

<210> SEQ ID NO 8
<211> LENGTH: 5
<212> TYPE: PRT
<213> ORGANISM: Mus musculus

<400> SEQUENCE: 8

Ser Tyr Trp Met His
 1               5

<210> SEQ ID NO 9
<211> LENGTH: 17
<212> TYPE: PRT
<213> ORGANISM: Mus musculus

<400> SEQUENCE: 9

Ala Ile Tyr Pro Gly Asn Ser Asp Thr Ser Tyr Asn Gln Lys Phe Lys
 1               5                  10                  15

Gly

<210> SEQ ID NO 10
<211> LENGTH: 8
<212> TYPE: PRT
```

<213> ORGANISM: Mus musculus

<400> SEQUENCE: 10

```
Val Tyr Gly Arg Ala Met Asp Tyr
1               5
```

<210> SEQ ID NO 11
<211> LENGTH: 324
<212> TYPE: DNA
<213> ORGANISM: Mus musculus
<220> FEATURE:
<221> NAME/KEY: CDS
<222> LOCATION: (1)..(324)

<400> SEQUENCE: 11

```
gac att gtg ctg aca cag tct cct gct tcc tta gct gta tct ctg ggg    48
Asp Ile Val Leu Thr Gln Ser Pro Ala Ser Leu Ala Val Ser Leu Gly
1               5                   10                  15 cag agg gcc acc atc tca tac agg gcc agc aaa agt gtc agt aca tct    96
Gln Arg Ala Thr Ile Ser Tyr Arg Ala Ser Lys Ser Val Ser Thr Ser
                20                  25                  30 ggc tat agt tat atg cac tgg aac caa cag aaa cca gga cag cca ccc   144
Gly Tyr Ser Tyr Met His Trp Asn Gln Gln Lys Pro Gly Gln Pro Pro
            35                  40                  45 aga ctc ctc atc tat ctt gta tcc aac cta gaa tct ggg gtc cct gcc   192
Arg Leu Leu Ile Tyr Leu Val Ser Asn Leu Glu Ser Gly Val Pro Ala
        50                  55                  60 agg ttc agt ggc agt ggg tct ggg aca gac ttc acc ctc aac atc cat   240
Arg Phe Ser Gly Ser Gly Ser Gly Thr Asp Phe Thr Leu Asn Ile His
65                  70                  75                  80 cct gtg gag gag gag gat gct gca acc tat tac tgt cag cac att agg   288
Pro Val Glu Glu Glu Asp Ala Ala Thr Tyr Tyr Cys Gln His Ile Arg
                85                  90                  95 gag ctt aca cgt tcg gag ggg gga cca agc tgg aaa                   324
Glu Leu Thr Arg Ser Glu Gly Gly Pro Ser Trp Lys
                100                 105
```

<210> SEQ ID NO 12
<211> LENGTH: 108
<212> TYPE: PRT
<213> ORGANISM: Mus musculus

<400> SEQUENCE: 12

```
Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
                20                  25                  30

Gly Tyr Ser Tyr Met His Trp Asn Gln Gln Lys Pro Gly Gln Pro Pro
            35                  40                  45

Arg Leu Leu Ile Tyr Leu Val Ser Asn Leu Glu Ser Gly Val Pro Ala
        50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
                100                 105
```

<210> SEQ ID NO 13
<211> LENGTH: 15
<212> TYPE: PRT
<213> ORGANISM: Mus musculus

<400> SEQUENCE: 13

Arg Ala Ser Lys Ser Val Ser Thr Gly Tyr Ser Tyr Met His
1               5                   10                  15

<210> SEQ ID NO 14
<211> LENGTH: 7
<212> TYPE: PRT
<213> ORGANISM: Mus musculus

<400> SEQUENCE: 14

Leu Val Ser Asn Leu Glu Ser
1               5

<210> SEQ ID NO 15
<211> LENGTH: 7
<212> TYPE: PRT
<213> ORGANISM: Mus musculus

<400> SEQUENCE: 15

Gln His Ile Arg Glu Leu Thr
1               5

<210> SEQ ID NO 16
<211> LENGTH: 115
<212> TYPE: PRT
<213> ORGANISM: Mus musculus

<400> SEQUENCE: 16

Val Gln Leu Gln Gln Ser Gly Thr Val Leu Ala Arg Pro Gly Ala Ser
1               5                   10                  15

Val Lys Met Ser Cys Lys Ala Ser Gly Tyr Thr Phe Thr Ser Tyr Trp
            20                  25                  30

Met His Trp Val Lys Gln Arg Pro Gly Gln Gly Leu Glu Trp Ile Gly
        35                  40                  45

Ala Ile Tyr Pro Gly Asn Ser Asp Thr Ser Tyr Asn Gln Lys Phe Lys
    50                  55                  60

Gly Lys Ala Lys Leu Thr Ala Val Thr Ser Thr Ser Thr Ala Tyr Met
65                  70                  75                  80

Glu Leu Ser Ser Leu Thr Asn Glu Asp Ser Ala Val Tyr Tyr Cys Thr
                85                  90                  95

Arg Val Tyr Gly Arg Ala Met Asp Tyr Trp Gly Gln Gly Thr Ser Val
            100                 105                 110

Thr Val Ser
        115

<210> SEQ ID NO 17
<211> LENGTH: 112
<212> TYPE: PRT
<213> ORGANISM: Artificial Sequence
<220> FEATURE:
<223> OTHER INFORMATION: sequence of matched amino acids

<400> SEQUENCE: 17

Val Gln Leu Gln Gln Ser Gly Thr Val Leu Ala Arg Pro Gly Ala Ser
1               5                   10                  15

Val Lys Met Ser Cys Lys Ala Ser Gly Tyr Thr Phe Thr Ser Tyr Trp
            20                  25                  30

Met His Trp Val Lys Gln Arg Pro Gly Gln Gly Leu Glu Trp Ile Gly
        35                  40                  45

Ala Ile Tyr Pro Gly Asn Ser Asp Thr Ser Tyr Asn Gln Lys Phe Lys

```
                    50                  55                  60
Gly Lys Ala Lys Leu Thr Ala Val Thr Ser Thr Ser Thr Ala Tyr Met
 65                  70                  75                  80

Glu Leu Ser Ser Leu Thr Asn Glu Asp Ser Ala Val Tyr Tyr Cys Thr
                 85                  90                  95

Arg Tyr Ala Met Asp Tyr Trp Gly Gln Gly Thr Ser Val Thr Val Ser
            100                 105                 110
```

<210> SEQ ID NO 18
<211> LENGTH: 116
<212> TYPE: PRT
<213> ORGANISM: Mus musculus

<400> SEQUENCE: 18

```
Val Gln Leu Gln Gln Ser Gly Thr Val Leu Ala Arg Pro Gly Ala Ser
  1               5                  10                  15

Val Lys Met Ser Cys Lys Ala Ser Gly Tyr Thr Phe Thr Ser Tyr Trp
             20                  25                  30

Met His Trp Val Lys Gln Arg Pro Gly Gln Gly Leu Glu Trp Ile Gly
         35                  40                  45

Ala Ile Tyr Pro Gly Asn Ser Asp Thr Ser Tyr Asn Gln Lys Phe Lys
 50                  55                  60

Gly Lys Ala Lys Leu Thr Ala Val Thr Ser Thr Ser Thr Ala Tyr Met
 65                  70                  75                  80

Glu Leu Ser Ser Leu Thr Asn Glu Asp Ser Ala Val Tyr Tyr Cys Thr
                 85                  90                  95

Arg Gly Asn Tyr Tyr Tyr Ala Met Asp Tyr Trp Gly Gln Gly Thr Ser
            100                 105                 110

Val Thr Val Ser
        115
```

<210> SEQ ID NO 19
<211> LENGTH: 108
<212> TYPE: PRT
<213> ORGANISM: Mus musculus

<400> SEQUENCE: 19

```
Asp Ile Val Leu Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
             20                  25                  30

Gly Tyr Ser Tyr Met His Trp Asn Gln Gln Lys Pro Gly Gln Pro Pro
         35                  40                  45

Arg Leu Leu Ile Tyr Leu Val Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ile Arg
                 85                  90                  95

Glu Leu Thr Arg Ser Glu Gly Gly Pro Ser Trp Lys
            100                 105
```

<210> SEQ ID NO 20
<211> LENGTH: 108
<212> TYPE: PRT
<213> ORGANISM: Artificial Sequence
<220> FEATURE:
<223> OTHER INFORMATION: sequence of matched amino acids -continued

```
<400> SEQUENCE: 20

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105

<210> SEQ ID NO 21
<211> LENGTH: 108
<212> TYPE: PRT
<213> ORGANISM: Mus musculus

<400> SEQUENCE: 21

Asp Ile Val Leu Thr Gln Ser Pro Ala Ser Leu Ala Val Ser Leu Gly
1               5                   10                  15

Gln Arg Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ile Arg
                85                  90                  95

Glu Leu Thr Arg Ser Glu Gly Gly Pro Ser Trp Lys
            100                 105

<210> SEQ ID NO 22
<211> LENGTH: 5
<212> TYPE: PRT
<213> ORGANISM: Mus musculus

<400> SEQUENCE: 22

Ser Tyr Trp Met His
1               5

<210> SEQ ID NO 23
<211> LENGTH: 5
<212> TYPE: PRT
<213> ORGANISM: Artificial Sequence
<220> FEATURE:
<223> OTHER INFORMATION: sequence of matched amino acids

<400> SEQUENCE: 23

Ser Tyr Trp Met His
1               5

<210> SEQ ID NO 24
<211> LENGTH: 5
<212> TYPE: PRT
```

```
<213> ORGANISM: Homo sapiens

<400> SEQUENCE: 24

Ser Tyr Trp Met His
1               5

<210> SEQ ID NO 25
<211> LENGTH: 17
<212> TYPE: PRT
<213> ORGANISM: Mus musculus

<400> SEQUENCE: 25

Ala Ile Tyr Pro Gly Asn Ser Asp Thr Ser Tyr Asn Gln Lys Phe Lys
1               5                   10                  15

Gly

<210> SEQ ID NO 26
<211> LENGTH: 17
<212> TYPE: PRT
<213> ORGANISM: Artificial Sequence
<220> FEATURE:
<223> OTHER INFORMATION: sequence of matched amino acids

<400> SEQUENCE: 26

Ala Ile Tyr Pro Gly Asn Ser Asp Thr Ser Tyr Asn Gln Lys Phe Lys
1               5                   10                  15

Gly

<210> SEQ ID NO 27
<211> LENGTH: 17
<212> TYPE: PRT
<213> ORGANISM: Mus musculus

<400> SEQUENCE: 27

Ala Ile Tyr Pro Gly Asn Ser Asp Thr Ser Tyr Asn Gln Lys Phe Lys
1               5                   10                  15

Gly

<210> SEQ ID NO 28
<211> LENGTH: 7
<212> TYPE: PRT
<213> ORGANISM: Mus musculus

<400> SEQUENCE: 28

Tyr Gly Arg Ala Met Asp Tyr
1               5

<210> SEQ ID NO 29
<211> LENGTH: 7
<212> TYPE: PRT
<213> ORGANISM: Artificial Sequence
<220> FEATURE:
<223> OTHER INFORMATION: sequence of matched amino acids

<400> SEQUENCE: 29

Tyr Gly Arg Ala Met Asp Tyr
1               5

<210> SEQ ID NO 30
<211> LENGTH: 7
<212> TYPE: PRT
<213> ORGANISM: Mus musculus

<400> SEQUENCE: 30
```

-continued

```
Tyr Gly Arg Ala Met Asp Tyr
1               5

<210> SEQ ID NO 31
<211> LENGTH: 15
<212> TYPE: PRT
<213> ORGANISM: Mus musculus

<400> SEQUENCE: 31

Arg Ala Ser Lys Ser Val Ser Thr Ser Gly Tyr Ser Tyr Met His
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: sequence of matched amino acids

<400> SEQUENCE: 32

Arg Ala Ser Lys Ser Val Ser Thr Ser Gly Tyr Ser Tyr Met His
1               5                   10                  15

<210> SEQ ID NO 33
<211> LENGTH: 15
<212> TYPE: PRT
<213> ORGANISM: Artificial Sequence
<220> FEATURE:
<223> OTHER INFORMATION: synthetic construct

<400> SEQUENCE: 33

Arg Ala Ser Lys Ser Val Ser Thr Ser Gly Tyr Ser Tyr Met His
1               5                   10                  15

<210> SEQ ID NO 34
<211> LENGTH: 7
<212> TYPE: PRT
<213> ORGANISM: Mus musculus

<400> SEQUENCE: 34

Leu Val Ser Asn Leu Glu Ser
1               5

<210> SEQ ID NO 35
<211> LENGTH: 7
<212> TYPE: PRT
<213> ORGANISM: Artificial Sequence
<220> FEATURE:
<223> OTHER INFORMATION: sequence of matched amino acids

<400> SEQUENCE: 35

Leu Val Ser Asn Leu Glu Ser
1               5

<210> SEQ ID NO 36
<211> LENGTH: 7
<212> TYPE: PRT
<213> ORGANISM: Turicibacter sp. HGF1

<400> SEQUENCE: 36

Leu Val Ser Asn Leu Glu Ser
1               5

<210> SEQ ID NO 37
<211> LENGTH: 7
<212> TYPE: PRT
<213> ORGANISM: Mus musculus
```

```
<400> SEQUENCE: 37

Gln His Ile Arg Glu Leu Thr
1               5

<210> SEQ ID NO 38
<211> LENGTH: 7
<212> TYPE: PRT
<213> ORGANISM: Artificial Sequence
<220> FEATURE:
<223> OTHER INFORMATION: sequence of matched amino acids

<400> SEQUENCE: 38

Gln His Ile Arg Glu Leu Thr
1               5

<210> SEQ ID NO 39
<211> LENGTH: 7
<212> TYPE: PRT
<213> ORGANISM: Pseudomonas brassicacearum subsp. brassicacearum NFM421

<400> SEQUENCE: 39

Gln His Ile Arg Glu Leu Thr
1               5
```

MONOCLONAL ANTIBODY AGAINST OXIDIZED LOW-DENSITY LIPOPROTEIN

CROSS REFERENCE TO RELATED APPLICATIONS

This is a U.S. national application of International Application PCT/JP2011/060376, filed Apr. 28, 2011, which claims priority to Japanese Application No. 2010-103663, filed Apr. 28, 2010, the contents of each of which applications are incorporated herein by reference in their entireties for all purposes.

FIELD OF THE INVENTION

The present invention relates to a monoclonal antibody against slightly oxidized low-density lipoprotein, a hybridoma for producing the monoclonal antibody, a kit for detecting slightly oxidized low-density lipoprotein, and a method for detecting slightly oxidized low-density lipoprotein contained in a biological sample collected from a subject.

BACKGROUND OF THE INVENTION

Oxidation of low-density lipoprotein (LDL) occurs due to excessive active oxygen, namely oxidative stress conditions, caused by disruption of the balance between generation and elimination of active oxygen in vivo. LDL is a giant molecule having a conjugate between apolipoprotein B and lipids such as cholesterol, phospholipid, and triglyceride. First, active oxygen oxidizes unsaturated fatty acid in the component lipids during the LDL oxidation. Next, a subsequent chain oxidation reaction occurs, followed by undergoing conjugated diene synthesis to generate lipid peroxide and aldehyde. This chain oxidation reaction or a direct oxidation reaction due to active oxygen also oxidizes apolipoprotein B to be cleaved. These oxidation reactions result in loss of the spherical structure of LDL, an increase in negative charge, and an altered affinity for receptors. This can produce oxidized LDL having characteristics different from those of native-LDL.

Oxidized LDL is present in atherosclerotic lesions, and is detected at a high concentration in sera from patients with hyperlipidemia, diabetes mellitus, or liver disease, etc., when compared with those from healthy subjects. Thus, oxidized LDL is considered to be an important substance in various diseases involved in oxidative stress. In order to be used for elucidation, treatment, diagnosis, and evaluation of these diseases, oxidized LDL-specific antibodies have been developed.

Examples of the antibodies can include: an anti-oxidized-phospholipid antibody that is produced by using, as an immunogen, oxidized LDL purified from atherosclerotic lesions and that recognizes, as an antigen, phospholipid having oxidatively cleaved fatty acid (Non Patent Literature 1); an anti-MDA-LDL antibody that is produced by using, as an immunogen, malondialdehyde-modified LDL (MDA-LDL) prepared from native-LDL in serum (Non Patent Literatures 2 and 3); and an antibody that is produced by preparing acetylated LDL, MDA-LDL, and metal-oxidized LDL from native-LDL in serum and by using, as an immunogen, a solution containing an equivalent amount of each of them (Patent Literature 1).

LDL is a giant particle having many sites susceptible to oxidation, so that the degree of the oxidation varies. In general, a large number of antioxidants such as vitamin C are present in blood in vivo. Oxidized LDL with a high degree of oxidation (highly oxidized LDL) is recognized as a foreign substance, and is thus rapidly removed by macrophages. Hence, oxidized LDL with a low degree of oxidation (slightly oxidized LDL) accounts for a large proportion of oxidized LDL present in blood, in particular. Meanwhile, highly oxidized LDL seems to account for a large proportion of oxidized LDL present in vascular walls and atherosclerotic lesions. The above-described reason seems to explain why the antibody disclosed in Non Patent Literature 1 is an antibody against highly oxidized LDL, but not against slightly oxidized LDL.

In addition, since in the antibodies disclosed in Non Patent Literatures 2 and 3, an antigen recognition site is present inside of LDL, a sample must undergo pretreatment to expose its antigenic site.

Furthermore, any of the antibodies disclosed in Non Patent Literatures 1 to 3 and Patent Literature 1 has not been produced using, as an immunogen, oxidized LDL present in serum. Consequently, when they are used for a serum or plasma sample, a false positive reaction occurs and their sensitivity is low. It is therefore difficult to detect effects resulting from drug administration or improvement in lifestyle.

CITATION LIST

Patent Literature

Patent Literature 1: Japanese Patent Laid-Open No. 09-5323

Non Patent Literature

Non Patent Literature 1: H. Itabe et al., J. Biol. Chem., vol. 269, p. 15274-15279, 1994
Non Patent Literature 2: K. Kotani et al., Biochim. Biophys. Acta., vol. 1215, p. 121-125, 1994
Non Patent Literature 3: K. Kotani et al., "Rinsho Byouri" (Clinical Pathology), vol. 45, p. 47-54, 1997

SUMMARY OF THE INVENTION

It is an object of the present invention to provide a monoclonal antibody against slightly oxidized LDL, the antibody being able to play a role as a critical tool for oxidized LDL-related research and development. It is also another object of the present invention to provide a simple kit for detecting slightly oxidized LDL by using the monoclonal antibody and a simple method for detecting slightly oxidized LDL contained in a biological sample collected from a subject.

The present inventors have conducted intensive research and have used, as an immunogen, triglyceride-rich low-density lipoprotein (TG-rich LDL) of slightly oxidized LDL occurring in sera from patients with liver disease to generate a hybridoma. Then, the present inventors have found that a monoclonal antibody produced from the selected hybridoma is characterized by having a higher degree of reactivity toward slightly oxidized LDL and a lower degree of reactivity toward highly oxidized LDL, and have completed the following respective embodiments of the present invention.

(1) A monoclonal antibody which specifically reacts with oxidized low-density lipoprotein, wherein an ELISA (Enzyme-linked immunosorbent assay) is carried out using the monoclonal antibody as a solid-phase antibody and using an anti-apolipoprotein B antibody as a detection antibody; and wherein a degree of reactivity between the monoclonal antibody and an antigen set forth in (b) is smaller than a degree of reactivity between the monoclonal antibody and an antigen set forth in (a) as follows:

(a) metal-oxidized low-density lipoprotein as obtained by reacting native low-density lipoprotein (native-LDL) at a final concentration of 0.493 g/L with copper sulfate at a final concentration of 3.29 µmol/L at 37° C. for 0.5 hour; and (b) metal-oxidized low-density lipoprotein as obtained by reacting native low-density lipoprotein (native-LDL) at a final concentration of 0.493 g/L with copper sulfate at a final concentration of 3.29 µmol/L at 37° C. for 24 hours.

(2) The monoclonal antibody according to (1), wherein the oxidized low-density lipoprotein is triglyceride-rich low-density lipoprotein (TG-rich LDL).

(3) The monoclonal antibody according to (1) or (2), wherein the oxidized low-density lipoprotein is human oxidized low-density lipoprotein.

(4) A monoclonal antibody which specifically reacts with oxidized small dense LDL in a healthy subject.

(5) A monoclonal antibody which specifically reacts with oxidized LDL at a particle size similar to a particle size of native-LDL in a patient with non-alcoholic steatohepatitis (NASH).

(6) A monoclonal antibody which specifically reacts with oxidized remnant lipoprotein in a patient with dyslipidemia.

(7) The monoclonal antibody according to any of (1) to (6), comprising a variable region comprising an amino acid sequence set forth in SEQ ID NO: 10.

(8) The monoclonal antibody according to any of (1) to (7), comprising a variable region (a) and/or a variable region (b) as follows:

(a) the variable region comprising, in the order from its N-terminus, an amino acid sequence set forth in SEQ ID NO: 8, an amino acid sequence set forth in SEQ ID NO: 9, and an amino acid sequence set forth in SEQ ID NO: 10; and (b) the variable region comprising, in the order from its N-terminus, an amino acid sequence set forth in SEQ ID NO: 13, an amino acid sequence set forth in SEQ ID NO: 14, and an amino acid sequence set forth in SEQ ID NO: 15.

(9) The monoclonal antibody according to any of (1) to (8), comprising a variable region consisting of an amino acid sequence set forth in SEQ ID NO: 7.

(10) The monoclonal antibody according to any of (1) to (9), comprising a variable region consisting of an amino acid sequence set forth in SEQ ID NO: 12.

(11) A monoclonal antibody which is produced from a hybridoma deposited under accession number NITE BP-916.

(12) A hybridoma which produces the monoclonal antibody according to any of (1) to (11).

(13) The hybridoma according to (12), which is a hybridoma deposited under accession number NITE BP-916.

(14) A kit for detecting oxidized low-density lipoprotein, comprising the monoclonal antibody according to any of (1) to (11).

(15) A method for detecting oxidized low-density lipoprotein contained in a biological sample collected from a subject, comprising the steps of: specifically reacting the monoclonal antibody according to any of (1) to (11) with oxidized low-density lipoprotein contained in a biological sample collected from a subject to form a complex; and detecting the complex.

(16) A method for detecting oxidized low-density lipoprotein contained in a biological sample collected from a subject, comprising the steps of: immobilizing the monoclonal antibody according to any of (1) to (11) on a support; specifically reacting the monoclonal antibody immobilized on the support with oxidized low-density lipoprotein contained in a biological sample collected from a subject to form a complex; and detecting the complex.

A monoclonal antibody, a hybridoma for producing the monoclonal antibody, a kit for detecting slightly oxidized LDL, and a method for detecting slightly oxidized LDL contained in a biological sample collected from a subject according to embodiments of the present invention can effectively and conveniently carry out elucidation, treatment, diagnosis, evaluation of various diseases involved in oxidized LDL such as TG-rich LDL. In addition, they can contribute to developing and thus providing a pharmaceutical composition having excellent drug efficacy.

BRIEF DESCRIPTION OF THE DRAWINGS

FIG. 4 shows the amino acid sequences which showed highest homology with the amino acid sequences of G11-6-VH and G11-6-VL in a homology search with known amino acid sequences.

FIG. 5 shows the amino acid sequences which showed highest homology with the amino acid sequences of two, CDR1 and CDR2, of the three complementarity determining regions (CDRs), CDR1, CDR2, and CDR3 of G11-6-VH in a homology search with known amino acid sequences.

FIG. 6 shows the amino acid sequences which showed highest homology with the amino acid sequences of CDR3 of G11-6-VH and CDR1 of G11-6-VL in a homology search with known amino acid sequences.

FIG. 7 shows the amino acid sequences which showed highest homology with the amino acid sequences of CDR2 and CDR3 of G11-6-VL in a homology search with known amino acid sequences.

FIG. 15 shows results of the determination of TC concentration, TG concentration, and PL concentration in gel filtration eluates of sera from patients with dyslipidemia (n=2), and ELISA of the eluates with an immobilized G11-6 antibody, and with an immobilized anti-MDA-LDL antibody.

DETAILED DESCRIPTION OF THE INVENTION

Figure 1:
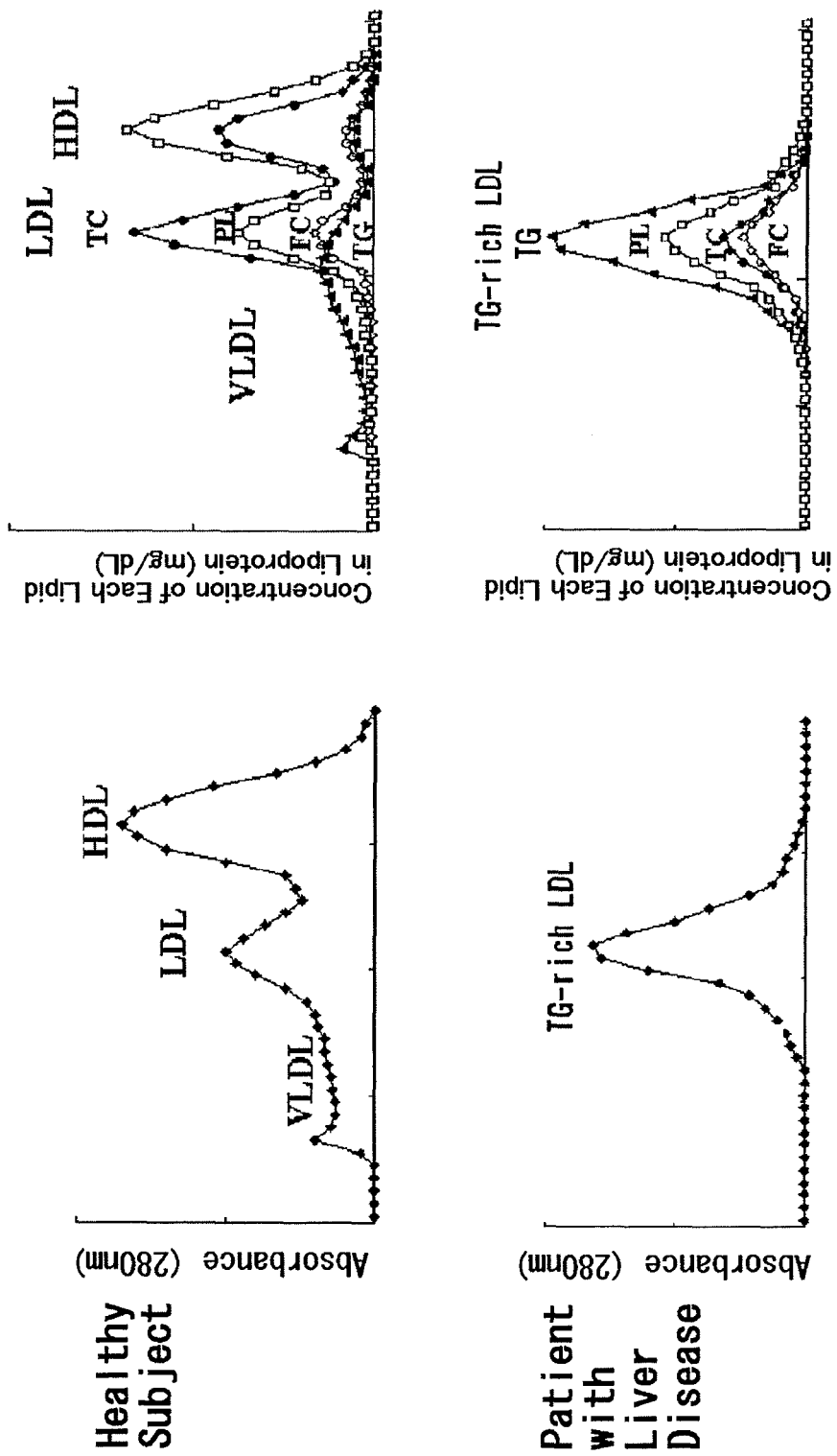
FIG. 1 shows gel filtration chromatography (upper and lower left panels) of total lipoprotein fractions separated by ultracentrifugation of serum from a healthy subject (n=1) or a patient with liver disease (n=1) and measurement results of lipid concentrations in the respective eluates from the gel filtration chromatography (upper and lower right panels). In the graph, TC denotes total cholesterol, PL denotes phospholipid, FC denotes free cholesterol, and TG denotes triglyceride. In each panel, the abscissa represents fraction numbers, which indicate a size; the size is smaller at positions in the line direction (right) on the abscissa.

Hereinafter, described in detail are a monoclonal antibody against slightly oxidized LDL, a hybridoma for producing the monoclonal antibody, a kit for detecting slightly oxidized LDL, and a method for detecting slightly oxidized LDL contained in a biological sample collected from a subject according to embodiments of the present invention. A monoclonal antibody against slightly oxidized LDL according to an embodiment of the present invention has a high degree of reactivity toward slightly oxidized LDL and a low degree of reactivity toward highly oxidized LDL.

Hereinafter, as used herein, the term "slightly oxidized LDL" refers to oxidized LDL (i.e., LDL that has been slightly oxidized) that has a relatively low number of oxidation products such as lipid peroxide, aldehyde, and cleaved apolipoprotein B generated in an oxidation reaction and that has a higher negative charge than native-LDL. The term "highly oxidized LDL" refers to oxidized LDL (i.e., LDL that has been highly oxidized) that has a relatively large number of oxidation products such as lipid peroxide, aldehyde, and cleaved apolipoprotein B generated in an oxidation reaction and that has a markedly higher negative charge than native-LDL.

In an embodiment of the present invention, the slightly oxidized LDL and the highly oxidized LDL can be each prepared in accordance with conventional procedures. For example, they can be prepared by metal-mediated oxidation of native-LDL in serum. In this case, the oxidation degree of the resulting oxidized LDL increases in proportion to the metal concentration or time of reaction with native-LDL. For example, slightly oxidized LDL can be produced by reacting native-LDL at a final concentration of about 0.493 g/L with copper sulfate at a final concentration of about 3.29 μmol/L at 37° C. for H1 hours (0<H1<24), by reacting native-LDL at a final concentration of about 0.493 g/L with copper sulfate at a final concentration of about 6.579 μmol/L at 37° C. for H2 hours (0<H2<8), by reacting native-LDL at a final concentration of about 0.476 g/L with copper sulfate at a final concentration of about 23.81 μmol/L at 37° C. for H3 hours (0<H3<8), or by reacting native-LDL at a final concentration of about 0.476 g/L with copper sulfate at a final concentration of about 47.62 µmol/L at 37° C. for H4 hours (0<H4<8). Highly oxidized LDL can be produced by reacting native-LDL at a final concentration of about 0.493 g/L with copper sulfate at a final concentration of about 3.29 µmol/L at 37° C. for at least 24 hours, by reacting native-LDL at a final concentration of about 0.493 g/L with copper sulfate at a final concentration of about 6.579 µmol/L at 37° C. for H5 hours (H5≤8), by reacting native-LDL at a final concentration of about 0.476 g/L with copper sulfate at a final concentration of about 23.81 µmol/L at 37° C. for H6 hours (H6≥8), or by reacting native-LDL at a final concentration of about 0.476 g/L with copper sulfate at a final concentration of about 47.62 µmol/L at 37° C. for H7 hours (H7≥8).

In an embodiment of the present invention, an ELISA using the monoclonal antibody as a solid-phase antibody and using an anti-apolipoprotein B antibody as a detection antibody, for example, can verify whether or not the monoclonal antibody has a high degree of reactivity toward slightly oxidized LDL and the monoclonal antibody has a low degree of reactivity toward highly oxidized LDL. That is, in this ELISA, if the degree of reactivity toward a sample using the highly oxidized LDL is lower than that of a sample using the slightly oxidized LDL, the monoclonal antibody used as the solid-phase antibody is characterized by having a high degree of reactivity toward slightly oxidized LDL and a low degree of reactivity toward highly oxidized LDL.

As used herein, the slightly oxidized LDL can include slightly oxidized LDL from birds or mammals such as a human, mouse, rat, monkey (i.e., a primate excluding a human), goat, dog, pig, guinea pig, rabbit, sheep, and chicken. Preferred is, however, slightly oxidized LDL from a human. In addition, the slightly oxidized LDL is preferably TG-rich LDL.

The TG-rich LDL is an LDL present in serum of at least a patient with liver disease. The TG-rich LDL is characterized by having a high content of triacylglycerol, which is triglyceride, (triglyceride, tri-O-acylglycerol; TG, TAG). In this respect, the TG-rich LDL is a lipoprotein different from native-LDL, which has a high cholesterol content. As liver disease progresses, the concentration of TG-rich LDL in serum increases. At the terminal stage of liver disease, the TG-rich LDL accounts for a large proportion of lipoprotein present in serum. The concentrations of very-low-density lipoprotein (VLDL), native-LDL, and high-density lipoprotein (HDL) in serum, however, markedly decrease (H. Nagasaka et al., J. Pediatr., vol. 146, p. 329-335, 2005).

In addition, TG-rich LDL can convert cultured macrophages into foam cells. The rate of formation of macrophage foam cells by TG-rich LDL is proportional to the serum concentration of malondialdehyde-modified LDL (MDA-LDL), a species of oxidized LDL (H. Nagasaka et al., J. Pediatr., vol. 146, p. 329-335, 2005). Although TG peroxide is hardly detected in plasma from a healthy subject, a marked increase in the TG peroxide concentration is observed in plasma from a patient with liver disease (SP. Hui et al., Lipids, vol. 38, p. 1287-1292, 2003). Because of this, TG-rich LDL is considered to be a species of oxidized LDL. Furthermore, a large amount of highly oxidized LDL cannot be present in serum. A large amount of TG-rich LDL, however, is present in serum from a patient with liver disease. Thus, the TG-rich LDL is considered to be a species of slightly oxidized LDL.

TG-rich LDL has a larger ratio by weight of TG than native-LDL. In addition, TG-rich LDL converts macrophages into foam cells. Such TG-rich LDL includes oxidized intermediate density lipoprotein [IDL (also referred to as a midband, including a remnant lipoprotein corresponding to IDL as a fraction)] (i.e., including oxidized remnant lipoprotein) and oxidized small dense LDL (sd-LDL, denatured LDL), the particle size of which is 25.5 nm or less and which is an oxidized lipoprotein corresponding to LDL at a density of 1.040 to 1.063 when fractionated.

Here, FIG. 1 and Table 1 show typical results of determining a ratio by weight of TG in TG-rich LDL. The upper and lower left graphs of FIG. 1 show the results of carrying out gel filtration chromatography of the total lipoprotein fraction while measuring absorbance at 280 nm, the total lipoprotein fraction being separated from sera of a healthy subject (the upper graph) and a patient with liver disease (the lower graph), respectively, by a ultracentrifugal method. The upper and lower right graphs of FIG. 1 show the results of carrying out gel filtration chromatography of the total lipoprotein fraction and determining the concentration of each lipid contained in the resulting respective eluates, the total lipoprotein fraction being separated from sera of a healthy subject (the upper graph) and a patient with liver disease (the lower graph), respectively, by a ultracentrifugal method. Meanwhile, Table 1 shows the results of the calculation of the average and standard deviation as obtained by determining the concentration of each lipid by the above procedure with regard to four patients with liver disease and seven healthy subjects.

TABLE 1

| | {Ratio by Weight (%)} | | | | |
|---|---|---|---|---|---|
| | Cholesteryl Ester (CE) | Free Cholesterol (FC) | Triglyceride (TG) | Phospholipid (PL) | Protein (Apolipoprotein) |
| Healthy Subject (n = 7) | 39.1 ± 1.8 | 8.2 ± 0.8 | 8.4 ± 1.5 | 22.5 ± 0.4 | 21.3 ± 1.3 |
| Patient with Liver Disease(n = 4) | 10.7 ± 6.5 | 11.6 ± 1.5 | 29.8 ± 6.3 | 26.0 ± 2.6 | 21.9 ± 3.1 |

The upper and lower left graphs of FIG. 1 demonstrate that in a patient with liver disease, VLDL and HDL disappear and TG-rich LDL with a particle size similar to that of native-LDL is present at a high concentration. The right graphs of FIG. 1 and Table 1 demonstrate that a ratio by weight of TG in the TG-rich LDL present at a high concentration is definitely larger than that of TG in native-LDL. Table 1, however, shows that a ratio by weight of each lipid in the TG-rich LDL has a large standard deviation. This indicates some degree of variation in a ratio by weight of TG in the TG-rich LDL.

In addition, the particle size of the TG-rich LDL can be determined by polyacrylamide gel electrophoresis or high performance liquid chromatography (HPLC) to produce a result similar to that of native-LDL. This result may somewhat vary depending on individual difference and disease severity of a subject.

The charge of TG-rich LDL can be determined by agarose gel electrophoresis to produce a result similar to that of native-LDL or to produce a result indicating a slightly more negative charge than that of native-LDL. This result may somewhat vary depending on individual difference and disease severity of a subject.

TG-rich LDL can be collected from serum of a patient with liver disease, but seems to be present in serum of not only a patient with liver disease, but also a patient with another disease, in particular, a disease involved in oxidative stress, or a subject suspected of suffering from such a disease. Examples of such a disease can include liver disease (e.g., acute hepatitis, chronic hepatitis, hepatic cirrhosis, hepatic fibrosis, benign recurrent intrahepatic cholestasis, biliary atresia, steatohepatitis, non-alcoholic steatohepatitis (NASH)), dyslipidemia (e.g., hypercholesterolemia, hyper-LDL cholesterolemia, low-HDL cholesterolemia, hypertriglyceridemia), atherosclerotic disease (e.g., cerebral infarction, ischemic heart disease, aortic aneurysm, nephrosclerosis, arteriosclerosis obliterans), diabetes mellitus, hypertension, and the like.

An antibody, in general, has two polypeptides of each light chain (L chain; molecular weight of about 25,000) and each heavy chain (H chain; molecular weight of about 50,000 to 77,000). The different polypeptides are bonded via a disulfide bond to form a basic structure of a Y-shaped heterotetramer. The tip portion of the Y-shaped structure is referred to as a variable region. The rest is called a constant region. Further, the variable region of a light chain is referred to as a VL region, and the variable region of a heavy chain is referred to as a VH region. The variable region constitutes an antigen-recognition site, and different antibodies have a wide variation in its amino acid sequence. In contrast, the amino acid sequence of the constant region has a relatively less variation among antibodies. Within the variable region, there is a region that directly contacts an antigen and plays a central role in binding to the antigen. This region has a markedly large variation in its amino acid sequence among antibodies, and is referred to as a complementarity determining region (CDR) or a hypervariable region. In addition, within the variable region, a region excluding the CDR is referred to as a framework region (FR). It has been generally known that the variable region has three CDRs (CDR1, CDR2, and CDR3) and four FRs (FR1, FR2, FR3, and FR4) surrounding the CDRs.

Variable regions (a VH region and a VL region) according to an embodiment of the present invention may include any amino acid sequence as long as: a monoclonal antibody according to an embodiment of the present invention has a high degree of reactivity toward slightly oxidized LDL and a low degree of reactivity toward highly oxidized LDL; the monoclonal antibody has a characteristic of specifically reacting with oxidized small dense LDL in a healthy subject; the monoclonal antibody has a characteristic of specifically reacting with oxidized LDL with a particle size similar to that of native-LDL in a patient with NASH; or the monoclonal antibody has a characteristic of specifically reacting with oxidized remnant lipoprotein in a patient with dyslipidemia. Also, examples of embodiments of amino acid sequences of variable regions (a VH region and a VL region) according to an embodiment of the present invention can include the following (i) to (v).

(i) An amino acid sequence comprising an amino acid sequence set forth in SEQ ID NO: 10;

(ii) an amino acid sequence comprising, in the order from its N terminus, an amino acid sequence set forth in SEQ ID NO: 8, an amino acid sequence set forth in SEQ ID NO: 9, and an amino acid sequence set forth in SEQ ID NO: 10;

(iii) an amino acid sequence comprising, in the order from its N terminus, an amino acid sequence set forth in SEQ ID NO: 13, an amino acid sequence set forth in SEQ ID NO: 14, and an amino acid sequence set forth in SEQ ID NO: 15;

(iv) an amino acid sequence set forth in SEQ ID NO: 7; and (v) an amino acid sequence set forth in SEQ ID NO: 12.

In an embodiment of the present invention, an amino acid sequence of a variable region can be verified in accordance with a common procedure. Such a procedure includes: first, for example, extracting RNA from a hybridoma that produces a monoclonal antibody according to an embodiment of the present invention as described below; and carrying out a reverse transcription reaction to yield cDNA. Next, the procedure further includes: amplifying a cDNA sequence of a variable region by a PCR using this cDNA as a template and using primers corresponding to known sequences suitable for amplifying the variable region; carrying out cloning as needed, and thereafter; and carrying out sequencing with a sequencer to determine the DNA sequence. Last, the procedure further includes converting the DNA sequence of the determined variable region into an amino acid sequence by using triplet codons to identify the amino acid sequence.

As used herein, the term "reacting" is interchangeable with the term "interacting", "binding", or "recognizing". In addition, in an embodiment of the present invention, an antibody "specifically reacts" with a specific antigen (immunogen). This may mean that the antibody apparently has reactivity toward the specific antigen. The case where the antibody "specifically reacts" with the specific antigen includes the case where the antibody does not react with any other antigen. The case, however, also includes the case where the antibody reacts with another antigen as well as markedly reacts with the specific antigen.

Next, a hybridoma according to an embodiment of the present invention produces a monoclonal antibody according to an embodiment of the present invention. A hybridoma according to an embodiment of the present invention can be generated by any method that can be appropriately selected by those skilled in the art. Examples of such a method can include a hybridoma method (Nature, vol. 256, p. 495-497, 1975), a trioma method, a human B-cell hybridoma method (Immunology Today, vol. 4, p. 72, 1983) and an EBV-hybridoma method (MONOCLONAL ANTIBODIES AND CANCER THERAPY, p. 77-96, Alan R. Liss, Inc., 1985). The examples also include a method comprising the following steps (i) to (iv).

(i) First, an immunogen is prepared. The immunogen may be prepared by any procedure. In an embodiment of the present invention, however, a TG-rich LDL fraction can be separated from serum, and then be concentrated by ultrafiltration, followed by dialysis to prepare the immunogen. Here, examples of a method for examining whether or not serum contains TG-rich LDL can include methods that can be appropriately selected by those skilled in the art. The examples of the method, however, can include agarose gel electrophoresis. In an embodiment of the present invention, sera from a subject and a healthy subject are subjected to agarose gel electrophoresis. When a band at the α-position is not detected in the subject serum and a band at the β-position is detected at a position located closer to the anode than that of the healthy subject serum, it can be determined that the subject serum contains TG-rich LDL.

In addition, examples of a method for separating a TG-rich LDL fraction from serum can include methods that can be appropriately selected by those skilled in the art. The examples of the method, however, can include a method comprising: subjecting a total lipoprotein fraction separated from serum by density gradient centrifugation to gel filtration chromatography, thereby separating a TG-rich LDL fraction, according to previous reports (H. Chiba et al., J. Lipid Res., vol. 38, p. 1204-1216, 1997; T. Hirano et al., J. Atherosclerosis and Thrombosis, vol. 12, p. 67-72, 2005).

(ii) Next, an animal is immunized with the separated TG-rich LDL fraction as an immunogen. The immunization can be appropriately performed using a common procedure. Also, examples of the immune animal can include, but are not limited to, a mouse, rat, monkey (a primate excluding a human), goat, dog, pig, guinea pig, rabbit, sheep, and chicken.

(iii) Then, antibody-producing cells are collected from the immunized animal. Examples of the antibody-producing cells can include splenocytes, lymph node cells, and peripheral blood cells. Further, in order to produce a hybridoma, the collected antibody-producing cell is fused to another cell. Examples of a procedure for collecting and fusing an antibody-producing cell can include procedures that can be appropriately selected by those skilled in the art. Also, a cell having a high proliferative potential is preferably used for a cell that is fused to the antibody-producing cell. For example, a cell line derived from a generally available myeloma cell can be used. The cell line used preferably has characteristics as follows: the cell line has drug selectivity; it cannot survive in a HAT selection medium (containing hypoxanthine, aminopterin, and thymidine) when not fused; and it can survive only when fused to the antibody-producing cell.

(iv) After that, a hybridoma producing a monoclonal antibody is screened from the generated hybridomas, the monoclonal antibody having a low degree of reactivity toward native-LDL and a high degree of reactivity toward metal-oxidized LDL. The screening can be carried out using a common procedure such as an ELISA and immunoblotting, a procedure that can be appropriately selected by those skilled in the art. In the case of screening using an ELISA, for example, an ELISA is carried out on an immobilized native-LDL by using a culture supernatant of a hybridoma. Next, the ELISA reaction is detected with an appropriately labeled (anti-immune animal) antibody. Then, a hybridoma is identified by identifying a culture supernatant that has a low degree of reactivity toward native-LDL and a high degree of reactivity toward metal-oxidized LDL.

The resulting hybridoma as obtained by a procedure comprising the above steps (i) to (iv) can be defined as a hybridoma according to an embodiment of the present invention. The cell, however, can be purified by additional cloning and screening to prepare a hybridoma according to an embodiment of the present invention. Examples of such cloning and screening can include limiting dilution, a trypsin filter paper method, and a penicillin cup method.

In addition, the monoclonal antibody produced from the hybridoma as so obtained can be a monoclonal antibody according to an embodiment of the present invention. Also, the antibody produced from the antibody-producing cell as collected in the step (iii) of the above procedure can be a monoclonal antibody according to an embodiment of the present invention. Examples of a process for extracting a monoclonal antibody from a hybridoma or an antibody-producing cell can include common processes such as a cell culture process and an ascites method. The extracted monoclonal antibody can be purified by appropriately selecting or combining known methods such as ammonium sulfate precipitation, HPLC, ion exchange chromatography, gel filtration chromatography, and affinity chromatography.

The class of the resulting monoclonal antibody can be determined according to an appropriate common procedure such as a procedure using an IsoStrip mouse monoclonal antibody isotyping kit (Roche, Inc.) when an immunized animal is a mouse. Any of IgG, IgA, IgM, IgD, and IgE can be used as a class of a monoclonal antibody according to an embodiment of the present invention.

Depending on the need, a monoclonal antibody according to an embodiment of the present invention can be used and labeled by a biotin, a radioisotope, a fluorescent substance, an enzyme, or the like. In addition, depending on the need, the antibody can be used and immobilized on a support such as a plate made of polystyrene, a plate made of polypropylene, a plate made of silicon, microbeads made of polystyrene, magnetic beads, and latex particles.

In addition, depending on the need, an animal having the ability to produce a human immunoglobulin can be immunized to produce a monoclonal antibody according to an embodiment of the present invention as a human antibody. Also, a chimeric antibody including an immune-animal-derived variable region and a human-derived constant region can be produced by using a genetic engineering technique. Furthermore, a humanized antibody having an immune-animal-derived hypervariable region while the rest of the antibody is derived from a human can be produced.

It is notable that a monoclonal antibody according to an embodiment of the present invention can include, but is not limited to, the monoclonal antibody produced by a hybridoma deposited on Mar. 17, 2010, at Patent Microorganisms Depository (NPMD), Incorporated Administrative Agency National Institute of Technology and Evaluation (2-5-8 Kazusakamatari Kisarazu-shi, Chiba-ken 292-0818, JAPAN), the accession number of which is NITE BP-916. Likewise, a hybridoma according to an embodiment of the present invention can include, but is not limited to, the hybridoma whose accession number is NITE BP-916 at the above depository.

Specifically, as demonstrated in Examples below, examples of a monoclonal antibody according to an embodiment of the present invention include a monoclonal antibody that specifically reacts with oxidized small dense LDL in a healthy subject, a monoclonal antibody that specifically reacts with oxidized LDL with a particle size similar to that of native-LDL in a patient with NASH, and a monoclonal antibody that specifically reacts with oxidized remnant lipoprotein in a patient with dyslipidemia.

As used herein, the term "healthy subject" refers to a healthy individual without disabilities ("Koujien", the sixth edition, by Iwanami Shoten, Publishers) and an individual not suffering from a disease at least involved in oxidized LDL.

Next, an embodiment of the present invention provides a kit for detecting slightly oxidized LDL according to an embodiment of the present invention. The kit according to an embodiment of the present invention includes a monoclonal antibody according to an embodiment of the present invention, but may also include its components such as a substance useful for practicing an immunological detection method (e.g., a secondary antibody, a labeled substance), a buffer, and an instrument as long as the kit does not lose its features.

Further, an embodiment of the present invention provides a method for detecting slightly oxidized LDL contained in a biological sample collected from a subject. A method for detecting slightly oxidized LDL according to an embodiment of the present invention may comprise an incubation step or a washing step without impairing the method for detecting slightly oxidized LDL according to an embodiment of the present invention.

The method for detecting slightly oxidized LDL according to an embodiment of the present invention is a method for detecting slightly oxidized LDL contained in a biological sample collected from a subject, the method comprising the following steps (i) and (ii):

(i) a step of specifically reacting a monoclonal antibody according to an embodiment of the present invention with oxidized LDL contained in a biological sample collected from a subject to form a complex (a complex formation step)

(ii) a step of detecting the complex (a detection step).

A process for forming a complex in the complex formation step (i) can include any process that can be appropriately selected by those skilled in the art. Examples of such a process can include a process for mixing a solution containing a monoclonal antibody of an embodiment of the present invention with a biological sample to form a complex, a process for immobilizing a biological sample on a support to react with a solution containing a monoclonal antibody of an embodiment of the present invention, and a process for immobilizing a monoclonal antibody of an embodiment of the present invention on a support to react with a biological sample.

Examples of a process for detecting a complex in the detection step (ii) can include common procedures (e.g., an ELISA, an indirect antibody method, latex agglutination, a turbidimetric method, a CLEIA), and a procedure for pre-labeling a monoclonal antibody or biological sample, followed by detecting the labeled moiety.

Next, a different embodiment of a method for detecting slightly oxidized LDL according to an embodiment of the present invention is a method for detecting oxidized LDL contained in a biological sample collected from a subject, the method comprising the following steps (i) to (iii):

(i) a step of immobilizing a monoclonal antibody of an embodiment of the present invention on a support (an immobilization step);

(ii) a step of specifically reacting the monoclonal antibody immobilized on the support with oxidized LDL contained in a biological sample collected from a subject to form a complex (an immobilized-complex formation step); and (iii) a step of detecting the complex (an immobilized-complex detection step).

In the immobilization step (i), any support can be used for a support having an immobilized monoclonal antibody according to an embodiment of the present invention. Examples of such a support can include those similar to the above support. In addition, the immobilization process is not particularly limited, and can be carried out depending on the support used with proper setting.

In the immobilized-complex formation step (ii) and the immobilized-complex detection step (iii), a process for forming an immobilized complex and a process for detecting an immobilized complex can include processes similar to the above complex formation step (i) and detection step (ii), respectively.

A kit for detecting slightly oxidized LDL and a method for detecting the same according to an embodiment of the present invention can be used for elucidation and diagnosis of not only liver disease but also various diseases involved in oxidized LDL, and evaluations of their severity, treatment efficacy, and oxidation degree of lipoprotein, etc.

Hereinafter, based on Examples, described are a monoclonal antibody against slightly oxidized LDL, a hybridoma for producing the monoclonal antibody, a kit for detecting slightly oxidized LDL, and a method for detecting slightly oxidized LDL contained in a biological sample collected from a subject according to embodiments of the present invention. It is notable that the scope of the present invention is not limited to features indicated by these Examples.

EXAMPLES

Example 1

Production of Monoclonal Antibody by Using TG-Rich LDL as Immunogen (1) Examination of TG-Rich LDL by Agarose Gel Electrophoresis Blood collected from a patient with terminal liver disease and a healthy subject was placed at room temperature for 1 hour, and then was subjected to centrifugation under conditions at 3500 rpm and 4° C. for 10 minutes to prepare sera from a patient with terminal liver diseases and a healthy subject. Next, 1.5 µL each of the resulting sera was applied to an agarose gel (Universal gel/8; HELENA, Inc.). The gel was placed in a barbital buffer solution at pH 8.6 with an ionic strength of 0.06, and was subjected to electrophoresis at 100 V and 150 W for 45 minutes. Then, the gel was dried with a dryer. Subsequently, two drops of Triton X-100 were added to 20 mL of methanol containing 0.03% (w/v) of Fat Red 7B (HELENA, Inc.). Additional 4 mL of 0.1 mol/L aqueous sodium hydroxide was added thereto to prepare a staining solution. The dried gel was impregnated in the staining solution for 10 minutes and stained. After that, the gel was destained by soaking in 75% (v/v) aqueous methanol solution for 10 seconds.

Figure 2:
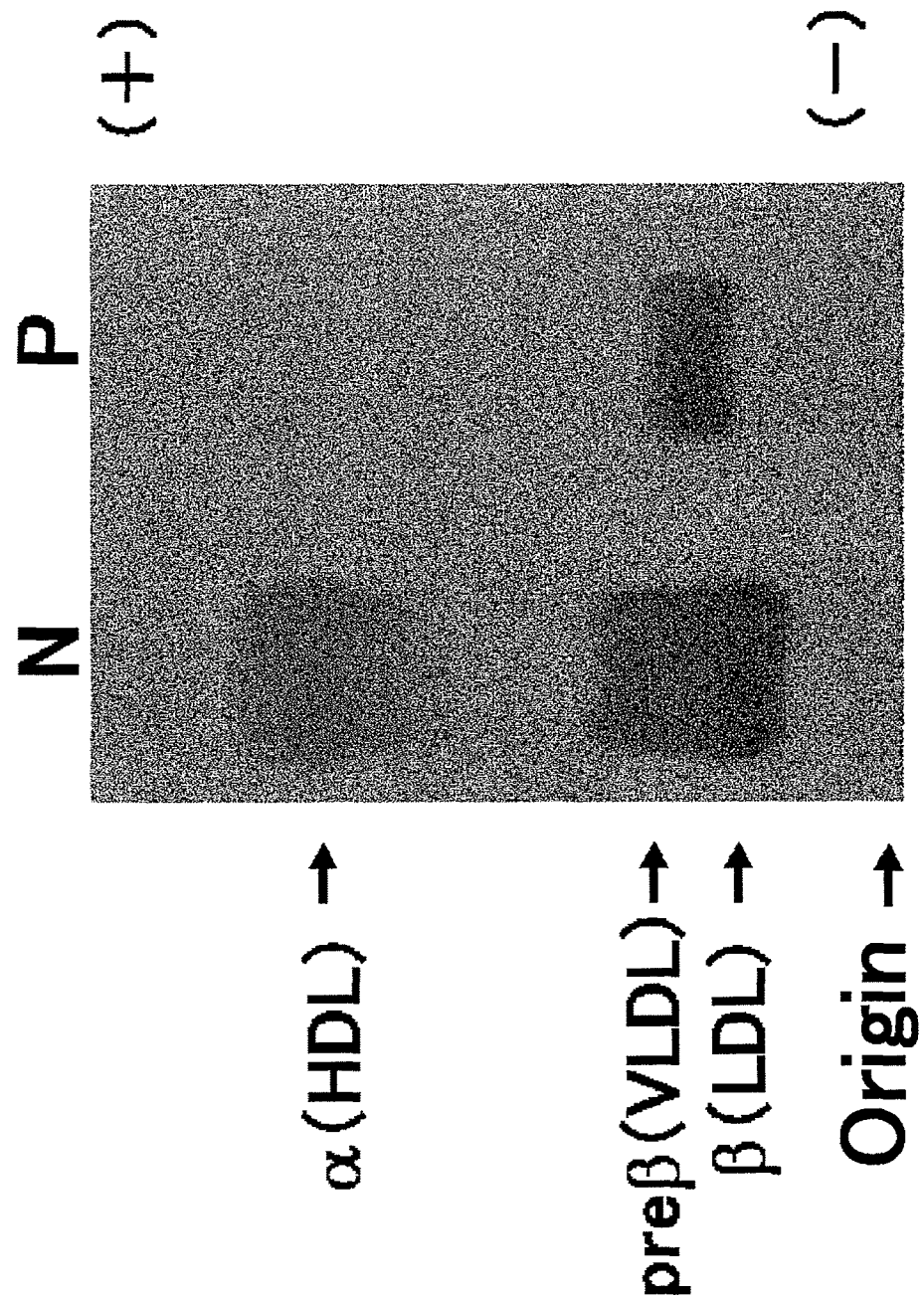
FIG. 2 shows a result of agarose gel electrophoresis of sera from a healthy subject (N) and a patient with terminal liver disease (P).

As shown in FIG. 2, in a serum (N) of a healthy subject, each band was detected at the α position corresponding to HDL and at the β position corresponding to LDL. In contrast, in a serum (P) of a patient with terminal liver disease, no band was detected at the α position. In addition, a band at the β position of the serum (P) of a patient with terminal liver disease was detected at a position located closer to the anode than that of a band at the β position of the serum (N) of a healthy subject. These results demonstrated that the serum of this patient with terminal liver disease did not contain HDL, but contained TG-rich LDL.

(2) Preparation of Immunogen

[2-1] Separation of Total Lipoprotein Fraction by Density Gradient Centrifugation This Example (1) demonstrated that a serum of a patient with terminal liver disease contained TG-rich LDL. The serum was subjected to density gradient centrifugation as previously reported (H. Chiba et al., J. Lipid Res., vol. 38, p. 1204-1216, 1997; T. Hirano et al., J. Atherosclerosis and Thrombosis, vol. 12, p. 67-72, 2005) to yield a total lipoprotein fraction. Specifically, to the serum of a patient with terminal liver disease of this Example (1) were added 0.7 mmol/L of 5,5'-dithiobis(2-nitrobenzoic acid) (DTNB; Wako Pure Chemical Industries, Ltd.) and 2.7 mmol/L (pH 7.4) of EDTA-2Na (Dojindo Molecular Technologies, Inc.). In addition, an appropriate amount of potassium bromide (Kanto Kagaku, Inc.) was added, and the mixture was adjusted at a specific gravity, d, of d=1.225 kg/L to prepare a sample solution. Next, an appropriate amount of potassium bromide (Kanto Kagaku, Inc.) was added to an aqueous solution (d=1.006 kg/L) containing 0.20 mol/L of sodium chloride, 0.27 mmol/L of EDTA-2Na (pH7.4), and 1 mmol/L of sodium hydroxide. The mixture was adjusted at a specific gravity, d, of d=1.225 kg/L to prepare a baric solution. Then, 12 mL of the sample solution was poured into a centrifuge tube (40PA; Hitachi Koki Co., Ltd.). The tube was filled with the baric solution, and centrifuged with an ultracentrifuge, himac CP60E ultracentrifuge (Hitachi Koki Co., Ltd.), and a rotor, RPV-50T rotor (Hitachi Koki Co., Ltd.), under conditions at 40000 rpm and 15° C. for 18 hours. After that, an upper layer (d<1.225 kg/L) was collected as a total lipoprotein fraction. About 8 mL of the total lipoprotein fraction collected was concentrated to 2 to 3 mL with an Amicon stirred cell Model 8050 (Millipore Corporation) and an ultrafilter, Amicon XM50 (Millipore Corporation), under a nitrogen gas atmosphere according to the attached protocol.

[2-2] Separation of TG-Rich LDL Fraction by Gel Filtration Chromatography

The total lipoprotein fraction of this Example (2)[2-1] was subjected to gel filtration chromatography as previously reported (H. Chiba et al., J. Lipid Res., vol. 38, p. 1204-1216, 1997; T. Hirano et al., J. Atherosclerosis and Thrombosis, vol. 12, p. 67-72, 2005) to yield a TG-rich LDL fraction. Specifically, the following instrument, reagents, and conditions were used to perform gel filtration chromatography while measuring absorbance at 280 nm. Then, 3 mL of each eluate was collected.

Sample: 2 to 3 mL of the total lipoprotein fraction of this Example (2) [2-1] (column load)
Column: Sepharose CL-4B (GE Healthcare, Inc.)
Buffer: 200 mL of 5 mmol/L Tris-HCl buffer (pH 7.4) containing 0.15 mol/L NaCl, 0.27 mmol/L EDTA-2Na, and 3 mmol/L $NaN_3$
Conditions: Chromatographic chamber at 4° C.
Flow rate at 0.15 mL/min Among the collected eluates, 9 mL (3 mL×3 fractions) of eluates before and after the absorbance peak were combined to prepare 18 mL (3 mL×6 fractions) of the TG-rich LDL fraction.

[2-3] Concentration and Dialysis of TG-Rich LDL Fraction

First, 18 mL of the TG-rich LDL fraction of this Example (2) [2-2] was concentrated to 2 to 3 mL with an Amicon stirred cell Model 8050 (Millipore Corporation) and an ultrafilter, Amicon XM50 (Millipore Corporation), under a nitrogen gas atmosphere according to the attached protocol. Then, the fraction was dialyzed overnight at 4° C. by using a phosphate buffer solution (PBS) as a dialysis solution and by using a dialysis membrane (cellulose tube 20/32; Sanko Junyaku Co., Ltd.) to prepare 2 to 3 mL of a TG-rich LDL solution. During the dialysis, the dialysis solution was changed three times.

[2-4] Determination of Protein Concentration of TG-Rich LDL Solution

The protein concentration of the TG-rich LDL solution of this Example (2) [2-3] was determined by a modified Lowry procedure as previously reported (M.A. Markwell et al., Anal. Biochem., vol. 87, p. 206-210, 1978). Specifically, an aqueous solution containing 2% (w/v) sodium carbonate, 0.4% (w/v) sodium hydroxide, 0.16% (w/v) tartrate, and 1% (w/v) sodium dodecyl sulfate (SDS) was prepared. This aqueous solution and 4% (w/v) copper sulfate aqueous solution were mixed at a volume ratio of 100:1 to prepare a reaction solution. In addition, deionized water and an equivalent amount of a phenol reagent (Folin & Ciocalteu's reagent: Wako Pure Chemical Industries, Ltd.) were mixed to prepare a Folin & Ciocalteu's reagent solution. Also, 500 µg/mL bovine serum albumin (BSA) aqueous solution was prepared as a standard solution. First, 3 mL of the reaction solution prepared was added to 1 mL each of the TG-rich LDL solution of this Example (2) [2-3] and the standard solution to carry out reaction at room temperature for 30 minutes. Next, 300 µL of the Folin & Ciocalteu's reagent solution prepared was added while vigorously stirring to carry out reaction at room temperature for 45 minutes. Then, each absorbance at 660 nm was determined. By comparing with the measured value of the standard solution, the protein concentration of the TG-rich LDL solution of this Example (2) [2-3] was calculated.

[2-5] Adjustment of Protein Concentration of TG-Rich LDL Solution

Based on the result as obtained by calculation in this Example (2) [2-4], the protein concentration of the TG-rich LDL solution of this Example (2) [2-3] was adjusted with PBS at 1 mg/mL, and the solution was then stored at 4° C.

(3) Immunization of Mouse by Using TG-Rich LDL as Immunogen and Generation of Hybridoma First, 0.1 mL of 0.5 to 1 mg/mL TG-rich LDL solution of this Example (2) [2-5] was made to pass through a filter with a pore size of 0.45 mm (DISMIC-25CS: ADVANTEC, Inc.). Next, a BALB/c mouse that had been injected with pertussis adjuvant according to a common procedure was intraperitoneally injected three times with the solution to perform immunization. Then, according to a common procedure, splenocytes were collected from the immunized mouse, and were fused with a mouse myeloma cell line P3U1 by using 50% polyethylene glycol 1500 (Roche, Inc.) to produce hybridomas. The hybridomas were cultured about 10 days by using RPMI 1640 medium containing penicillin/streptomycin, 10% (w/v) fetal calf serum (FCS), and a HAT solution until colonies were able to be observed according to a common procedure.

(4) Hybridoma Screening by ELISA with Immobilized TG-Rich LDL, Native-LDL, or Metal-Oxidized LDL

[4-1] Preparation of Native-LDL Fraction

According to procedures described in these Examples (2) [2-1], [2-2], [2-3], [2-4], and [2-5], a native-LDL solution was prepared from a serum of a healthy subject.

[4-2] Preparation of Metal-Oxidized LDL Fraction

To 1 mg/mL of the native-LDL solution of this Example (4) [4-1] was added copper sulfate at 25 µmol/L, and the mixture was incubated at 37° C. for 24 hours. The mixture was dialyzed overnight at 4° C. by using PBS as a dialysis solution to prepare a metal-oxidized LDL solution.

[4-3] ELISA with Immobilized Native-LDL or Metal-Oxidized LDL

The native-LDL solution of this Example (4) [4-1] and the metal-oxidized LDL solution of this Example (4) [4-2] were each diluted with PBS at 20 µg/mL. Next, 50 µL/well of each solution was each placed in a 96-well plate (Nunc MaxiSorp: Nalgene Nunc International, Inc.) and was reacted overnight at 4° C. This made each of the native-LDL and the metal-oxidized LDL immobilized on the plate. The liquid was removed, and 1% (w/v) BSA-containing PBS was dispensed at 150 µL/well and incubated at 37° C. for 2 hours to perform blocking. Then, the plate was washed four times with 0.05% (v/v) Tween 20-containing PBS (0.05% Tween-PBS). Subsequently, 50 µL/well of the culture supernatant of each colony of this Example (3) was dispensed in a well with immobilized native-LDL and a well with immobilized metal-oxidized LDL to carry out reaction at room temperature for 1 hour. The plate was then washed four times with 0.05% Tween-PBS. Thereafter, a biotin-labeled rat anti-mouse κ chain antibody (Zymed Laboratories, Inc.) which had been diluted 500 times with PBS was dispensed in each well at 50 µL/well to carry out reaction at room temperature for 1 hour. The plate was then washed four times with 0.05% Tween-PBS. After that, an alkaline phosphatase-labeled streptavidin (ALP-SA; Zymed Laboratories, Inc.) which had been diluted 500 times with 0.05% Tween-PBS was dispensed at 50 µL/well to carry out reaction at room temperature for 30 minutes. The plate was then washed four times with 0.05% Tween-PBS. Next, a 10 mmol/L diethanolamine solution containing 0.5 mmol/L MgCl$_2$ was used to adjust disodium p-nitrophenyl phosphate hexahydrate (Wako Pure Chemical Industries, Ltd.) at 1 mg/mL. This solution was dispensed at 100 μL/well to carry out reaction at room temperature for 30 minutes. Subsequently, the absorbance was read with a microplate reader (Bio-Rad Laboratories, Inc.) at the first wavelength of 405 nm and the second wavelength of 600 nm. Colonies were selected by identifying a culture supernatant exhibiting low absorbance in a well with immobilized native-LDL and by identifying a culture supernatant exhibiting high absorbance in a well with immobilized metal-oxidized LDL.

[4-4] Cloning and Screening by Limiting Dilution

Cells forming a colony as selected in this Example (4) [4-3] was plated on a 96-well plate at 1 cell/well, and cultured using RPMI1640 medium (10% FCS-HT-HFCS-RPMI1640) containing penicillin/streptomycin, 10% (v/v) FCS, hypoxanthine, thymidine, and a hybridoma fusion cloning supplement (Roche, Inc.). These culture supernatants were subjected to an ELISA again according to a procedure described in this Example (4) [4-3]. A clone was selected by identifying a culture supernatant exhibiting low absorbance in a well with immobilized native-LDL and by identifying a culture supernatant exhibiting high absorbance in a well with immobilized metal-oxidized LDL. As a result, the resulting hybridoma was designated as G11-6.

(5) Purification of G11-6 Antibody

According to a common procedure, a mouse that had been injected with 2,6,10,14-tetramethyl-2-pentadecenoic acid (pristene) was intraperitoneally injected and inoculated with G11-6 of this Example (4) to grow ascites containing a monoclonal antibody (G11-6 antibody) produced by G11-6.

According to a common procedure, the resulting ascites was subjected to saturated ammonium sulfate precipitation to yield a crude monoclonal antibody solution. Specifically, while the resulting ascites was cooled on ice, an equivalent amount of saturated ammonium sulfate was slowly added dropwise. Next, the mixture was centrifuged to remove a supernatant. Then, a 50% saturated ammonium sulfate solution was added to the resulting precipitate, and the mixture was centrifuged again to remove a supernatant for washing. The resulting precipitate was dissolved in PBS to prepare a crude G11-6 antibody solution.

Following that, 300 μL of the crude G11-6 antibody solution was subjected to HPLC according to a common procedure using the following instrument apparatus, elute, and conditions. Last, 0.5 mL of each eluate was fractionated to yield about 1.4 mL of a purified G11-6 antibody solution at 80 μg/mL.

Column: Superose 6 10/300 GL (GE Healthcare, Inc.)
Elute: 50 mmol/L NaPB solution (pH 7.2)
System controller: CBM-20A (Shimadzu Corporation)
Feed pump: LC-20AD (Shimadzu Corporation)
Autosampler: SIL-20A (Shimadzu Corporation)
Column oven: CTO-20AC (Shimadzu Corporation)
Detector: SPD-20A (Shimadzu Corporation)
Conditions: Flow rate at 0.5 mL/min
Detection wavelength at 280 nm Example 2

Class Determination of G11-6 Antibody

The class of G11-6 antibody of Example 1 (5) was determined by immunochromatography using an IsoStrip mouse monoclonal antibody isotyping kit (Roche, Inc.) according to the attached protocol. The result revealed that the class of G11-6 antibody was IgM.

Example 3

Identifying Sequence of Variable Region of G11-6 Antibody (1) RNA Extraction

Hybridoma G11-6 of Example 1 (4) was inoculated in a 25-cm$^3$ flask containing 10 mL of 10% FCS-containing RPMI1640 medium, and was cultured under 5% CO$_2$ atmosphere at 37° C. for 72 hours. Next, a supernatant was removed by centrifugation under conditions at ordinary temperature and 8500 rpm for 5 minutes to recover a cell pellet. Then, RNA was extracted from the recovered cell pellet by using an Absolutely RNA Miniprep kit (Stratagene, Inc.) according to the attached protocol.

Specifically, first, 4.2 μL of β-mercaptoethanol was added to 600 μL of a lysis buffer, and the mixture was applied to a cell pellet. After sheared with a 18G syringe (the outer diameter of 1.2 mm, the inner diameter of 0.94 mm), the whole amount was loaded on a prefilter spin cup (Cup1), and was centrifuged under conditions at ordinary temperature and 14000 rpm for 5 minutes to collect about 600 μL of a filtrate. Here, 600 μL of 70% (v/v) ethanol was added and mixed by inversion to prepare about 1200 mL of an ethanol mixture. Next, 700 μL of the mixture was transferred to an RNA binding spin cup (Cup2), the cup was centrifuged under conditions at ordinary temperature and 14000 rpm for 1 minute to remove a filtrate. The rest of about 500 μL of the ethanol mixture was added, and the mixture was centrifuged again under conditions at ordinary temperature and 14000 rpm for 1 minute. Then, a filtrate was removed, and 600 μL of a low salt wash buffer was added. The cup was centrifuged under conditions at ordinary temperature and 14000 rpm for 1 minute, followed by additional centrifugation to remove a filtrate. Subsequently, the cup was centrifuged under conditions at ordinary temperature and 14000 rpm for 2 minutes to remove a filtrate. 50 μL of a DNase digestion buffer and 5 μL of reconstituted RNase-free DNase I were mixed and added to the Cup2, and were incubated at 37° C. for 15 minutes. Furthermore, 600 μL of a high-salt wash buffer was added to the Cup2, and was centrifuged under conditions at ordinary temperature and 14000 rpm for 1 minute to remove a filtrate. To the Cup2 was added 600 μL of the low salt wash buffer, and the cup was centrifuged under conditions at ordinary temperature and 14000 rpm for 1 minute to remove a filtrate. In addition, 300 μL of the low salt wash buffer was added to the Cup2, and was centrifuged under conditions at ordinary temperature and 14000 rpm for 2 minutes to transfer the content of the Cup2 to a new 1.5-mL Eppendorf tube. Subsequently, 50 μL of an elution buffer heated to 60° C. was added to the Cup2, and the cup was kept at room temperature for 2 minutes. After that, the Cup2 was centrifuged under conditions at ordinary temperature and 14000 rpm for 1 minute to collect a filtrate. The filtrate was designated as an RNA solution. The RNA concentration of the RNA solution was determined with a NanoDrop1000 (Thermo Scientific, Inc.), and was 128 ng/μL. Then, an appropriate amount of DEPC water was added to the RNA solution, and the RNA concentration was adjusted at about 100 ng/μL.

(2) cDNA Preparation

By using the RNA solution of this Example (1) as a template, a reverse transcription reaction was carried out using a SuperScript™ first-strand synthesis system for RT-PCR (Invitrogen, Inc.) according to the attached protocol to prepare a cDNA. Specifically, first, reaction solution A and reaction solution B having the following compositions were prepared.

Reaction solution A: 8 µL of about 100 ng/µL RNA solution, 1 µL of 10 mmol/L dNTP mix, and 1 µL of 50 ng/µL random hexamers Reaction solution B: 2 µL of 10×RT buffer, 4 µL of 25 mmol/L MgCl$_2$, 2 µL of 0.1 mol/L DTT, and 1 µL of 40 U/mL RNaseOUT™

The reaction solution A was mixed and incubated at 65° C. for 5 minutes. Then, the solution was placed on ice for 1 minute. Subsequently, the reaction solution B was added to the reaction solution A, and the mixture was incubated at room temperature for 2 minutes. Following that, 1 µL of Superscript™ II RT was added and incubated, in sequence, at room temperature for 10 minutes, at 42° C. for 50 minutes, and at 70° C. for 15 minutes. This allowed for a reverse transcription reaction to prepare a cDNA. The resulting cDNA solution was stored at 4° C.

(3) Amplification of DNA Sequences of Variable Region of Heavy Chain (G11-6-VH) and Variable Region of Light Chain (G11-6-VL) of G11-6 Antibody By using the cDNA solution of this Example (2) as a template, a PCR was carried out with a thermal cycler (Gene-Amp PCR System 2400; Applied Biosystems, Inc.). Then, DNA sequences of the variable region of the heavy chain of G11-6 antibody (G11-6-VH) and the variable region of the light chain of G11-6 antibody (G11-6-VL) were each amplified. The following describes primers used for the PCR, compositions of the PCR reaction solution, and conditions for the PCR.

Primers used for the PCR [Mouse Ig-Primer Set (Novagen, Inc.)] G11-6-VH (5' primer; MuIgVH5'-B): 5'-GGGAAT-TCATGRAATGSASCTGGGTYWTYCTCTT-3' (R represents A or G, S represents C or G, Y represents C or T, and W represents A or T; SEQ ID NO: 1) G11-6-VH (3' primer; MuIgMVH3'): 5'-CCCAAGCTTACGAGGGGGAAGA-CATTTGGGAA-3' (SEQ ID NO: 2) G11-6-VL (5' primer; MuIgkVL5'-B): 5'-GGGAATTCATGGAGACAGACA-CACTCCTGCTAT-3' (SEQ ID NO: 3) G11-6-VL (3' primer; MuIgkVL3'): 5'-CCCAAGCTTACTGGATGGTGGGAA-GATGGA-3' (SEQ ID NO: 4)

Compositions of the PCR reaction solution: 2.5 µL of 10×PCR buffer (Mg$^{2+}$ free), 0.75 µL of 50 mmol/L MgCl$_2$, 2.0 µL of 2.5 mmol/L dNTP mix, 1.0 µL of 250 pmol/L 5' primer, 1.0 µL of 250 µmol/L 3' primer, 1.0 µL of cDNA solution, 0.25 µL of Platinum Taq DNA polymerase, and 16.5 µL of DEPC water Conditions for the PCR: After 2 minutes of reaction at 94° C., 40 cycles, each of which consists of a reaction at 94° C. for 30 seconds, a reaction at 50° C. for 30 seconds, and a reaction at 72° C. for 2 minutes, were repeated. Then, a reaction was performed at 72° C. for 6 minutes.

A solution containing the amplified DNA sequence of G11-6-VH (VH-PCR product solution) and a solution containing the amplified DNA sequence of G11-6-VL (VL-PCR product solution) were stored at 4° C.

(4) Examination of PCR Product by Electrophoresis

Figure 3:
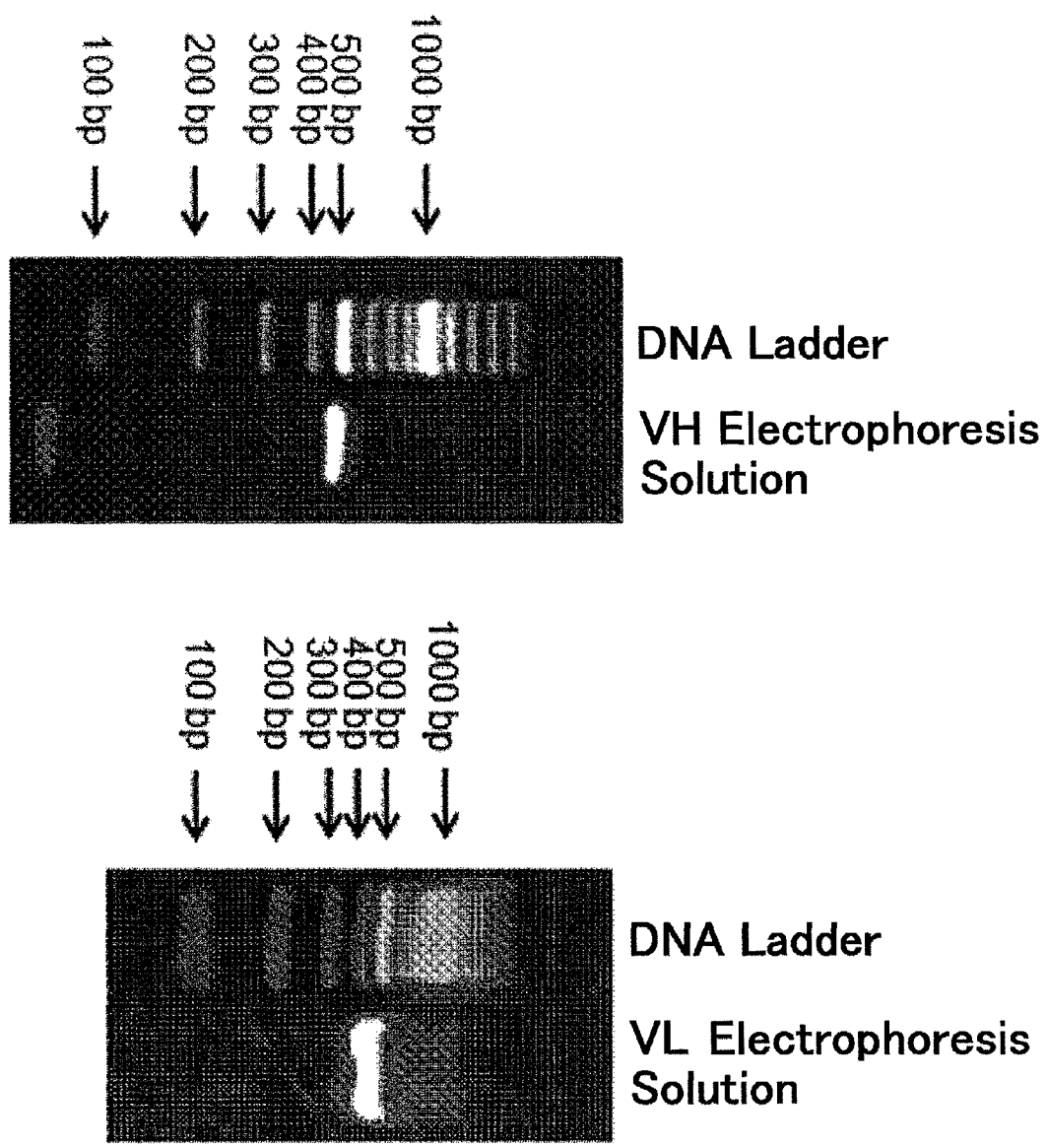
FIG. 3 shows a result of electrophoresis of the VH electrophoresis solution prepared by performing PCR for the DNA sequence of the variable region of the heavy chain of G11-6 antibody (G11-6-VH), and adding a loading buffer to a solution containing the resulting PCR product (left panel); and the VL electrophoresis solution prepared by performing PCR for the cDNA sequence of the variable region of the light chain of G11-6 antibody (G11-6-VL), and adding a loading buffer to a solution containing the resulting PCR product (right panel).

First, 5 µL each of the VH-PCR product solution and the VL-PCR product solution was pipetted, and 2 µL of a loading buffer (6× Orange DNA Loading Dye; Fermentas, Inc.) was added to each solution to prepare a VH electrophoresis solution and a VL electrophoresis solution. The VH electrophoresis solution, the VL electrophoresis solution, and a DNA ladder (O' GeneRuler™ 100 bp DNA Ladder Plus; Fermentas, Inc.) were applied to 0.007% (v/v) ethidium bromide (Nippon Gene Co., Ltd.)-containing 3% (w/v) agarose gel (NuSieve GTG Agarose; CAMBREX, Inc.). Next, 2 µL of ethidium bromide (Nippon Gene Co., Ltd.) was added to electrophoresis buffer (1×TAB buffer; Nippon Gene Co., Ltd.) at the anode side, and was mixed. Then, electrophoresis was performed at 100 V for about 40 minutes. After that, the resulting electrophoresis image was analyzed with a UV detector (Dolphin-View; KURABO, Inc.). FIG. 3 shows the results.

As shown in the left image of FIG. 3, a band of about 450 bp was detected in a lane for the VH electrophoresis solution. A band of about 400 bp was detected in a lane for the VL electrophoresis solution. This result verified that the DNA sequence of G11-6-VH was amplified using the VH-PCR product solution, and the DNA sequence of G11-6-VL was amplified using the VL-PCR product solution.

(5) Recovery and Insertion of PCR Product into Vector

First, 15 µL each of the VH-PCR product solution and the VL-PCR product solution of this Example (3) was dispensed, and was subjected to electrophoresis according to a procedure described in Example (4). Subsequently, a band of about 450 bp was excised from the agarose gel in which the VH-PCR product solution had been electrophoresed, and a band of about 400 bp was excised from the agarose gel in which the VL-PCR product solution had been electrophoresed. Next, a solution containing the DNA fragment was recovered with a QIAquick gel extraction kit (Qiagen, Inc.) according to the attached protocol to prepare a G11-6-VH-DNA solution and a G11-6-VL-DNA solution. Then, by using a TOPO TA cloning kit for sequencing (Invitrogen, Inc.), a VH ligation reaction solution containing 4 µL of the G11-6-VH-DNA solution, 1 µL of a salt solution, and 1 µL of a TOPO vector and a VL ligation reaction solution containing 4 µL of the G11-6-VL-DNA solution, 1 µL of a salt solution, and 1 µL of a TOPO vector were prepared and kept at room temperature for 5 minutes to insert the DNA fragment into the vector.

(6) Transformation and Culture of E. coli

First, 2 µL of the VH ligation reaction solution and 2 µL of the VL ligation reaction solution of this Example (5) were each added to TOP10 chemically competent E. coli (One Shot TOP10 Chemically Competent E. coli; Invitrogen, Inc.) and mixed. The mixture was placed on ice for 30 minutes. Next, the mixture was placed at 42° C. for 30 seconds, and then was immediately cooled on ice. After that, 250 µL of an E. coli growth medium, S.O.C. medium (Invitrogen, Inc.) was added to each mixture, and the resulting mixture was kept at 37° C. for 1 hour to transform E. coli. A solution containing E. coli transformed with the VH ligation reaction solution was designated as a VH E. coli solution. A solution containing E. coli transformed with the VL ligation reaction solution was designated as a VL E. coli solution.

Six 4% (w/v) LB agar plates (Invitrogen, Inc.) containing 1% (v/v) ampicillin (Invitrogen, Inc.) were prepared, and divided into two groups of a VH plate group and a VL plate group, each of which has three plates. Then, 10 µL, 50 µL, and 100 µL of the VH E. coli solution and the VL E. coli solution were added to and plated on the respective plates of the VH plate group and the VL plate group, respectively. After that, all the plates were incubated at 37° C. for 15 hours. Following that, eight colonies on the plate from the VH plate group and seven colonies from the VL plate group were picked up with a sterilized tooth pick. Each picked-up colony was added to 5 mL of 2% (w/v) LB Broth Base solution (Invitrogen, Inc.) containing 1% (v/v) ampicillin (Invitrogen, Inc.). These solutions were cultured at 37° C. for 15 hours while shaking with a BIO-SHAKER BR-15 (TAITEC, Inc.) at a shaking speed of 200 min$^{-1}$ to yield VH E. coli cultures (total of eight samples) and VL E. coli cultures (total of seven samples).

(7) Purification of Plasmid DNA

One sample of the VH *E. coli* cultures and one sample of the VL *E. coli* cultures of this Example (6) were centrifuged under conditions at ordinary temperature and 3000 rpm for 10 minutes, and a supernatant was then removed to collect a VH *E. coli* pellet and a VL *E. coli* pellet. After that, a plasmid was purified with a QIAprep Spin Miniprep kit (Fermentas, Inc.) to prepare a VH plasmid solution and a VL plasmid solution. Specifically, 250 µL of P1 solution was added to each of the VH *E. coli* pellet and the VL *E. coli* pellet, and the mixture was suspended. After the mixture was transferred to a 1.5-mL Eppendorf tube, 250 µL of P2 solution was added and mixed by inversion. Then, the mixture was left for several minutes, and the *E. coli* was lysed. Subsequently, 350 µL of N3 solution was added and mixed by inversion for neutralization. After the mixture was centrifuged under conditions at ordinary temperature and 14000 rpm for 1 minute, each supernatant was collected and loaded on a column. Following that, this column was centrifuged under conditions at ordinary temperature and 14000 rpm for 1 minute to remove a filtrate. Then, 750 µL of PE solution was added to the column, and the column was centrifuged under conditions at ordinary temperature and 14000 rpm for 1 minute to remove a filtrate. This allowed the column to be washed. The column was transferred to a new 1.5-mL Eppendorf tube. Then, 50 µL each of EB solution was added to keep the column for 1 minute. After that, the column was centrifuged under conditions at ordinary temperature and 14000 rpm for 2 minutes to collect a filtrate. This filtrate was designated as a plasmid solution. The plasmid solution as obtained from the VH *E. coli* pellet was designated as a VH plasmid solution. The plasmid solution as obtained from the VL *E. coli* pellet was designated as a VL plasmid solution. The VH plasmid solution and the VL plasmid solution were stored at 4° C.

(8) Sequencing

By using each of the VH plasmid solution and the VL plasmid solution of this Example (7) as a template, a sequencing reaction was carried out using a BigDye Terminator v3.1 Cycle Sequencing kit (Applied Biosystems, Inc.) and a T3 primer (ATTAACCCTCACTAAAGGGA: SEQ ID NO: 5). Compositions of the sequence reaction solution and conditions for the sequencing reaction were as follows.

Compositions of the sequence reaction solution: 2 µL of Ready Reaction Mix, 1 µL of a sequencing buffer, 1 µL of T3 primer, 5 µL of DEPC water, and 1 µL of a template DNA.

Conditions for the sequencing reaction: After 10 seconds of reaction at 96° C., 25 cycles, each of which consists of a reaction at 96° C. for 10 seconds, a reaction at 50° C. for 5 seconds, and a reaction at 60° C. for 3 minutes, were repeated. Then, the sample was kept at 4° C.

Subsequently, 45 µL of a SAM™ solution (Applied Biosystems, Inc.) and 10 µL of a BigDye X Terminator™ solution (Applied Biosystems, Inc.) were added to a sequencing reaction solution using the VH plasmid solution as a template DNA (i.e., a VH sequencing reaction solution) and a sequencing reaction solution using the VL plasmid solution as a template DNA (i.e., a VL sequencing reaction solution). Then, the mixture was stirred with a MicroMixer E-36 (TAITEC, Inc.) for 30 minutes under dark conditions at room temperature. After that, the mixture was centrifuged under conditions at ordinary temperature and 14000 rpm for 10 seconds to recover a supernatant. The DNA sequence was analyzed with a sequencer (3730×1 DNA Analyzer; Applied Biosystems, Inc.). Following that, software (MacVector; MacVector, Inc.) was used to convert the resulting DNA sequences to amino acid sequences and complementarity determining regions (CDRs), namely, CDR1, CDR2 and CDR3. The following shows the results.

DNA sequence of G11-6-VH:

```
                                                                      (SEQ ID NO: 6)
GTTCAGCTCCAGCAGTCTGGGACTGTGCTGGCAAGGCCTGGGGCTTCAGTGAAGATGTCCTGCAAGGCTTCTGGCTAC

ACCTTTACCAGCTACTGGATGCACTGGGTAAAACAGAGGCCTGGACAGGGTCTGGAATGGATTGGCGCTATTTATCCT

GGAAATAGTGATACTAGCTACAACCAGAAGTTCAAGGGCAAGGCCAAACTGACTGCAGTCACATCCACCAGCACTGCC

TACATGGAGCTCAGCAGCCTGACAAATGAGGACTCTGCGGTCTATTACTGTACAAGAGTCTACGGTAGGGCTATGGAC

TACTGGGGTCAAGGAACCTCAGTCACCGTCTCCTCA
```

Amino acid sequence of G11-6-VH (The underline portion indicates, in sequence, CDR1, CDR2, and CDR3 regions):

```
                                                                      (SEQ ID NO: 7)
VQLQQSGTVLARPGASVKMSCKASGYTFTSYWMHWVKQRPGQGLEWIGAIYPGNSDTSYNQKFKGKAKLTAVTSTSTA

YMELSSLTNEDSAVYYCTRVYGRAMDYWGQGTSVTVSS
```

CDR1 of VH region: SYWMH (SEQ ID NO: 8)
CDR2 of VH region: AIYPGNSDTSYNQKFKG (SEQ ID NO: 9)
CDR3 of VH region: VYGRAMDY (SEQ ID NO: 10)
DNA sequence of G11-6-VL:

```
                                                                      (SEQ ID NO: 11)
GACATTGTGCTGACACAGTCTCCTGCTTCCTTAGCTGTATCTCTGGGGCAGAGGGCCACCATCTCATACAGGGCCAGC

AAAAGTGTCAGTACATCTGGCTATAGTTATATGCACTGGAACCAACAGAAACCAGGACAGCCACCCAGACTCCTCATC

TATCTTGTATCCAACCTAGAATCTGGGGTCCCTGCCAGGTTCAGTGGCAGTGGGTCTGGGACAGACTTCACCCTCAAC
```

-continued
ATCCATCCTGTGGAGGAGGAGGATGCTGCAACCTATTACTGTCAGCACATTAGGGAGCTTACACGTTCGGAGGGGGA

CCAAGCTGGAAA

Amino acid sequence of G11-6-VL (The underline portion indicates, in sequence, CDR1, CDR2, and CDR3 regions):

(SEQ ID NO: 12)
DIVLTQSPASLAVSLGQRATISYRASKSVSTSGYSYMHWNQQKPGQPPRLLIYLVSNLESGVPARFSGSGSGTDFTLN

IHPVEEEDAATYYCQHIRELTRSEGGPSWK

CDR1 of VL region: RASKSVSTSGYSYMH (SEQ ID NO: 13)
CDR2 of VL region: LVSNLES (SEQ ID NO: 14)
CDR3 of VL region: QHIRELT (SEQ ID NO: 15)

(9) Homology Search with Amino Acid Sequence

Sequences of G11-6-VH and G11-6-VL of this Example (8) and the respective amino acid sequences of CDR1, CDR2, and CDR3 thereof are analyzed with software (MacVector; MacVector, Inc.) to conduct Clustal W and BLAST analysis, thereby searching homology with existing amino acid sequences. As a result of the homology search, FIGS. 4 to 7 show those with the highest homology.

As shown in FIGS. 4 to 7, a known amino acid sequence having 100% identity with the amino acid sequence of G11-6-VL was detected. No known amino acid sequence having 100% identity with the amino acid sequence of G11-6-VH, however, was detected. In addition, a known amino acid sequence having 100% identity with each of CDR1 of G11-6-VH, CDR2 of G11-6-VH, CDR1 of G11-6-VL, CDR2 of G11-6-VL, and CDR3 of G11-6-VL was detected. No known amino acid sequence having 100% identity with the amino acid sequence of CDR 3 of G11-6-VH, however, was detected. These results demonstrated that G11-6 antibody was a novel antibody.

Example 3

Reactivity Toward Serum of Patient with Liver Disease in ELISA with Immobilized G11-6 Antibody (1) Preparation of Serum Sample Serum was collected as a sample from a patient with liver disease and a healthy subject.

(2) ELISA with Immobilized G11-6 Antibody

[2-1] Preparation of Biotin-Labeled Anti-Apolipoprotein B Antibody (Detection Antibody)

<2-1-1> Purification of Anti-Apolipoprotein B Antibody

Goat antiserum containing an anti-apolipoprotein B polyclonal antibody (WatPa; Enterprises, Inc.) was precipitated with saturated ammonium sulfate according to a common procedure and a procedure as described in Example 1(5) to yield a crude anti-apolipoprotein B antibody solution. Subsequently, the crude anti-apolipoprotein B antibody solution was subjected to affinity column chromatography according to a common procedure to yield a purified anti-apolipoprotein B antibody. Specifically, first, the crude anti-apolipoprotein B antibody solution was diluted 10 times with PBS, and was then made to circulate and pass through an affinity column by using the following instrument apparatus and conditions.

Column: Protein G Sepharose 4 Fast Flow (GE Healthcare, Inc.)
Feed pump: Peristaltic pump (SJ-1215; ATTO, Inc.)
Conditions: 4° C.; Flow rate of about 0.2 mL/min Subsequently, the inside of the column was washed with PBS, and 0.1 mol/L of glycine-HCl (pH 2.7) was then made to pass through the column at a flow rate of about 0.2 mL/min. A column-bound anti-apolipoprotein B antibody was eluted, and 0.5 mL of each eluate was then collected.

After the fractionated eluates were neutralized by immediately adding 1 mol/L Tris-HCl (pH 8.0), absorbance of each eluate was measured at a wavelength of 280 nm. This made it possible to select an eluate in which a protein was verified to be present. The selected eluates were combined. Their absorbance was determined at a wavelength of 280 nm, and a protein concentration was estimated. The result demonstrated that 3.5 mL of the purified anti-apolipoprotein B antibody solution at 4.7 mg/mL was obtained. Following that, a dialysis membrane (cellulose tube 20/32; Sanko Junyaku Co., Ltd.) was used for dialysis overnight at 4° C. by using PBS as a dialysis solution to yield 3.5 mL of a purified anti-apolipoprotein B antibody solution. During the dialysis, the dialysis solution was changed three times. Then, PBS was used to adjust its protein concentration at 2 mg/mL.

<2-1-2> Biotin Labeling of Anti-Apolipoprotein B Antibody

An N-hydroxysuccinimide ester of biotin (EZ-Link NHS-Biotin Reagents; Thermo Fisher Scientific K. K.) was dissolved at 10 mmol/L into dimethylsulfoxide (Wako Pure Chemical Industries, Ltd.) to prepare a biotin-labeling solution. Next, 27 μL of the prepared biotin-labeling solution was added to 1 mL of the anti-apolipoprotein B antibody solution of this Example (2) [2-1] <2-1-1>, and the mixture was reacted at room temperature for 4 hours while stirring. Then, dialysis was carried out using PBS as a dialysis solution to remove unreacted biotin. This allowed a biotin-labeled anti-apolipoprotein B antibody to be prepared. After that, the antibody was diluted with PBS at a protein concentration of 0.01 mg/mL.

[2-2] ELISA with Immobilized G11-6 Antibody

The G11-6 antibody of Example 1(5) was diluted with PBS at a protein concentration of 5 μg/mL. This sample was dispensed in a 96-well plate (Nunc MaxiSorp; Nalgene Nunc International, Inc.) at 50 μL/well, and was incubated at 37° C. for 2 hours to immobilize the G11-6 antibody on the plate. The liquid was removed, and 1% (w/v) BSA-containing PBS was dispensed at 150 μL/well. After blocked by incubation at 37° C. for 2 hours, the plate was washed four times with 0.05% Tween-PBS. Subsequently, PBS was used to dilute the serum sample of this Example (1) by 20 times. The sample was dispensed at 50 μL/well, and was incubated overnight at 4° C. Then, the plate was washed four times with 0.05%

Tween-PBS. Next, the biotin-labeled goat anti-apolipoprotein B antibody of this Example (2) [2-1] <2-1-2> was dispensed at 50 μL/well, and was reacted at room temperature for 1 hour. Then, the plate was washed four times with 0.05% Tween-PBS. Following that, ALP-SA (Zymed Laboratories, Inc.) which had been diluted 250 times with 0.05% Tween-PBS was dispensed at 50 μL/well, and was reacted at room temperature for 30 minutes. Then, the plate was washed four times with 0.05% Tween-PBS. Further, 0.5 mmol/L $MgCl_2$-containing 10 mmol/L diethanolamine solution was used to adjust disodium p-nitrophenyl phosphate hexahydrate (Wako Pure Chemical Industries, Ltd.) at 1 mg/mL. The resulting solution was dispensed at 100 μL/well, and was subjected to coloring reaction at room temperature for 60 minutes. After that, absorbance was read with a microplate reader (Multiskan FC; Thermo Fisher Scientific K. K.) at the first wavelength of 405 nm and the second wavelength of 620 nm.
(3) ELISA with Immobilized Anti-Oxidized-Phospholipid Antibody Reactivity of the serum sample of this Example (1) in an ELISA was determined using an oxidized-LDL ELISA kit (oxidized-LDL determination reagent "MX"; Kyowa Medex Co., Ltd.) according to the attached protocol. Specifically, a reaction buffer was dispensed at 100 μL/well in a plate on which the mouse anti-oxidized-phospholipid monoclonal antibody had been immobilized. The serum samples of this Example (1) were diluted 250 times by using the attached sample diluent. Each sample was dispensed at 20 μL/well, and was incubated at 37° C. for 2 hours. Then, the plate was washed four times with the attached wash solution. Following that, the peroxidase-labeled goat anti-human apolipoprotein B polyclonal antibody was dispensed at 100 μL/well, and was incubated at 37° C. for 1 hour. Then, the plate was washed four times with the above wash solution. After that, a 3,3',5, 5'-tetramethylbenzidine solution was dispensed at 100 μL/well, and was incubated at 37° C. for 30 minutes. After the reaction was terminated by addition of 0.5 mol/L sulfuric acid at 50 μL/well, absorbance was read with a microplate reader (Multiskan FC; Thermo Fisher Scientific K. K.) at the first wavelength of 450 nm and the second wavelength of 620 nm.
(4) ELISA with Immobilized Anti-MDA-LDL Antibody Reactivity of the serum sample of this Example (1) in an ELISA was determined using an oxidized-LDL ELISA kit (oxidized-LDL ELISA "DAIICHI"; Sekisui Medical Co., Ltd.) according to the attached protocol. Specifically, the attached wash solution was used to wash three times a plate on which the mouse anti-MDA-LDL monoclonal antibody had been immobilized. Subsequently, a sample diluent (HEPES buffer) was used to dilute the serum sample of this Example (1) by 2000 times. Each sample was dispensed at 100 μL/well, and was reacted at room temperature for 2 hours. Then, the plate was washed three times with the attached wash solution. Following that, a β-galactosidase-labeled mouse anti-apolipoprotein B monoclonal antibody was dispensed at 100 μL/well, and was reacted at room temperature for 1 hour. Then, the plate was washed three times with the attached wash solution. After that, a substrate, which was an o-nitrophenyl-β-D-galactopyranoside solution, was dispensed at 100 μL/well, and was reacted at room temperature for 2 hours. Thereafter, aqueous sodium carbonate was added at 100 μL/well to stop the reaction. Finally, absorbance was read with a microplate reader (NOVAPATH; Bio-Rad Laboratories, Inc.) at the first wavelength of 415 nm and the second wavelength of 655 nm.

Figure 8:
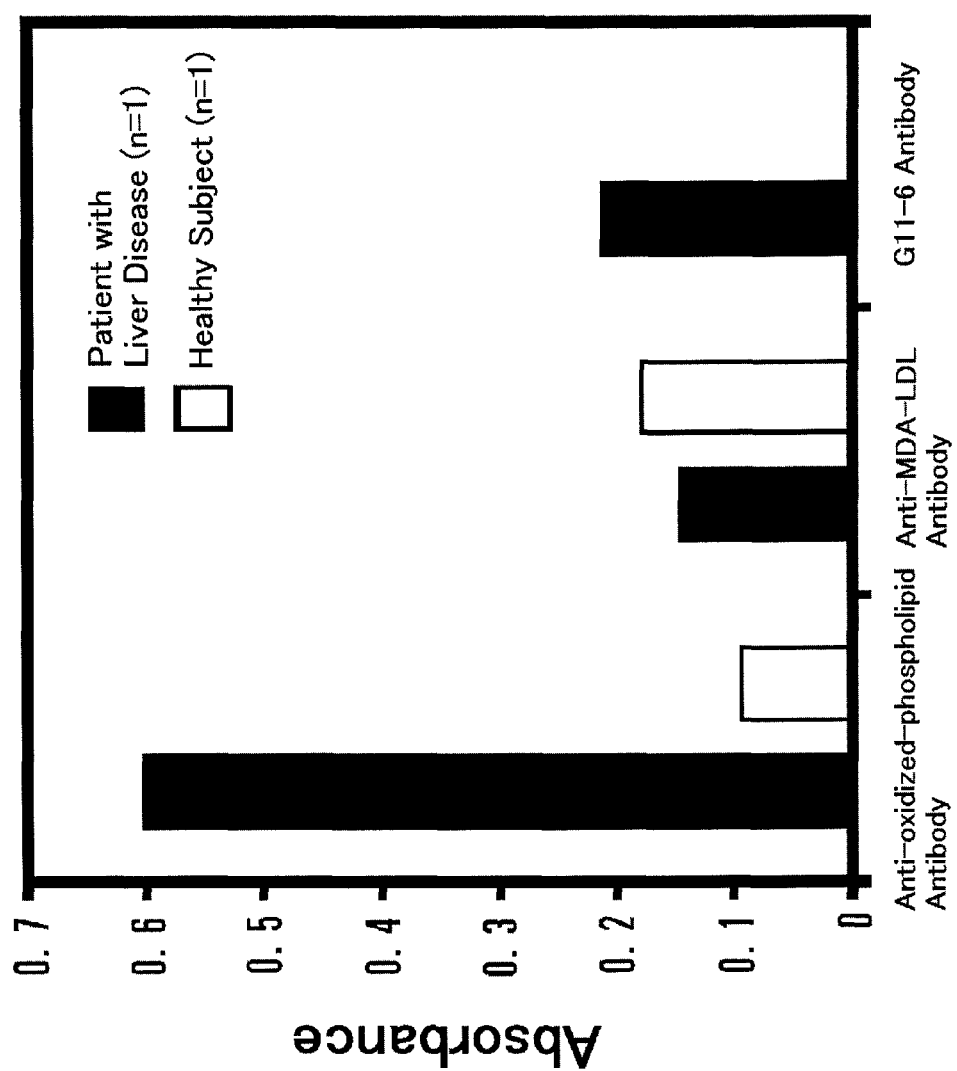
FIG. 8 shows results of ELISA of sera from a patient with liver disease (n=1) and a healthy subject (n=1), with an immobilized G11-6 antibody, with an immobilized anti-oxidized-phospholipid antibody, and with an immobilized anti-MDA-LDL antibody.

FIG. 8 shows the results of these Examples (2), (3), and (4). As shown in FIG. 8, the ELISA with an immobilized G11-6 antibody demonstrated that the absorbance was 0.212 in a patient with liver disease and almost no absorbance was detected in a healthy subject. In contrast, the ELISA with an immobilized anti-oxidized-phospholipid antibody demonstrated that the absorbance was 0.602 in the patient with liver disease and was 0.094 in the healthy subject. In addition, the ELISA with an immobilized anti-MDA-LDL antibody demonstrated that the absorbance was 0.146 in the patient with liver disease and was 0.179 in the healthy subject.

These results demonstrated that the anti-oxidized-phospholipid antibody and the anti-MDA-LDL antibody substantially reacted with serum not only from a patient with liver disease but also from a healthy subject. In contrast, the G11-6 antibody reacted with serum from a patient with liver disease, but hardly reacted with serum from a healthy subject. This indicated that the G11-6 antibody had excellent specificity.

Example 4

Figure 9:
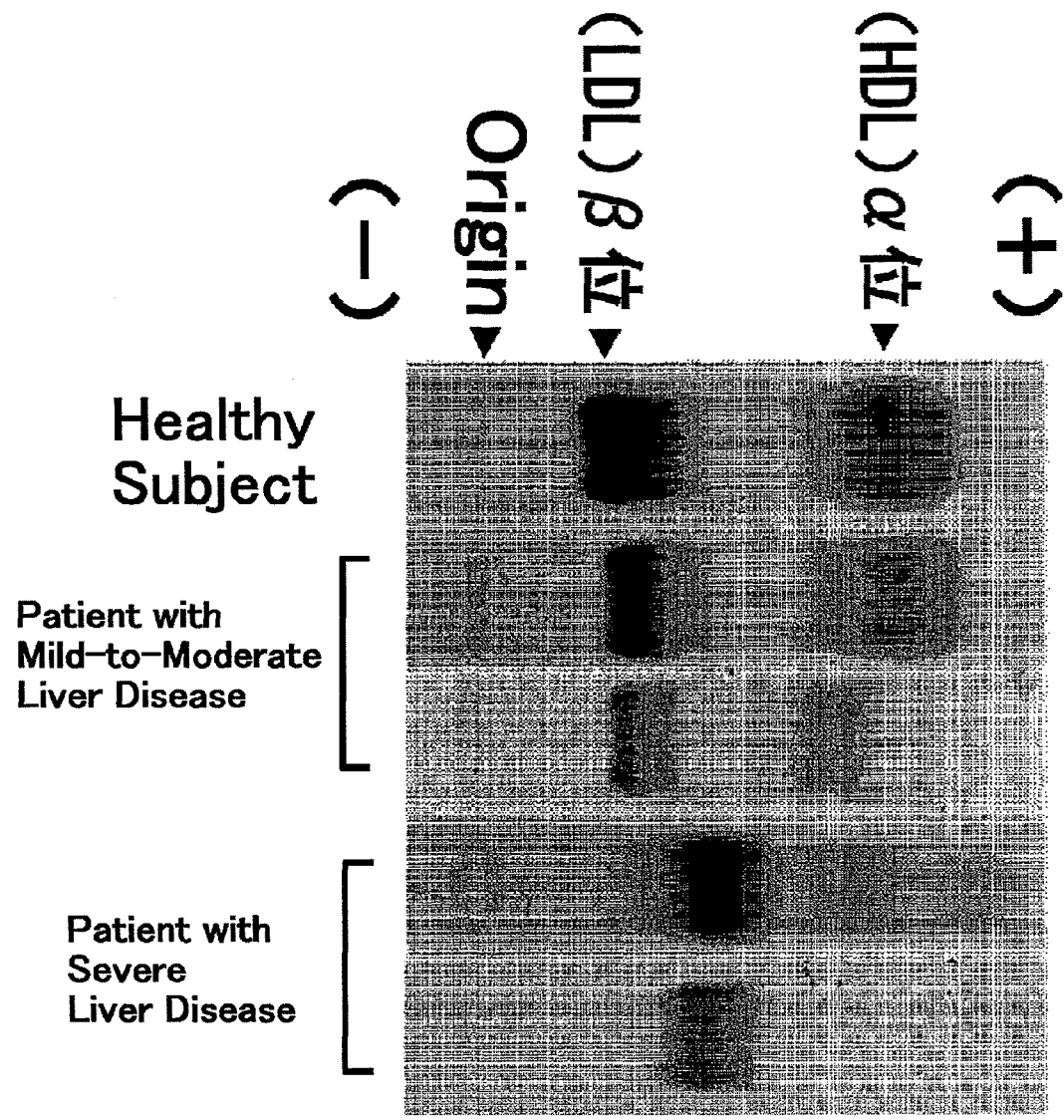
FIG. 9 shows a result of agarose gel electrophoresis of sera from a healthy subject, patients with mild-to-moderate liver disease, and patients with severe liver disease.

Association Between Liver Disease Severity and Reactivity in ELISA with Immobilized G11-6 Antibody (1) Determination of Liver Disease Severity by Agarose Gel Electrophoresis Serum of each of 9 patients with liver disease and 14 healthy subjects was collected, and was subjected to agarose gel electrophoresis according to a procedure described in Example 1(1). FIG. 9 shows the typical results of electrophoresis of the serum from a healthy subject and the serum from a patient with liver disease.

Figure 10:
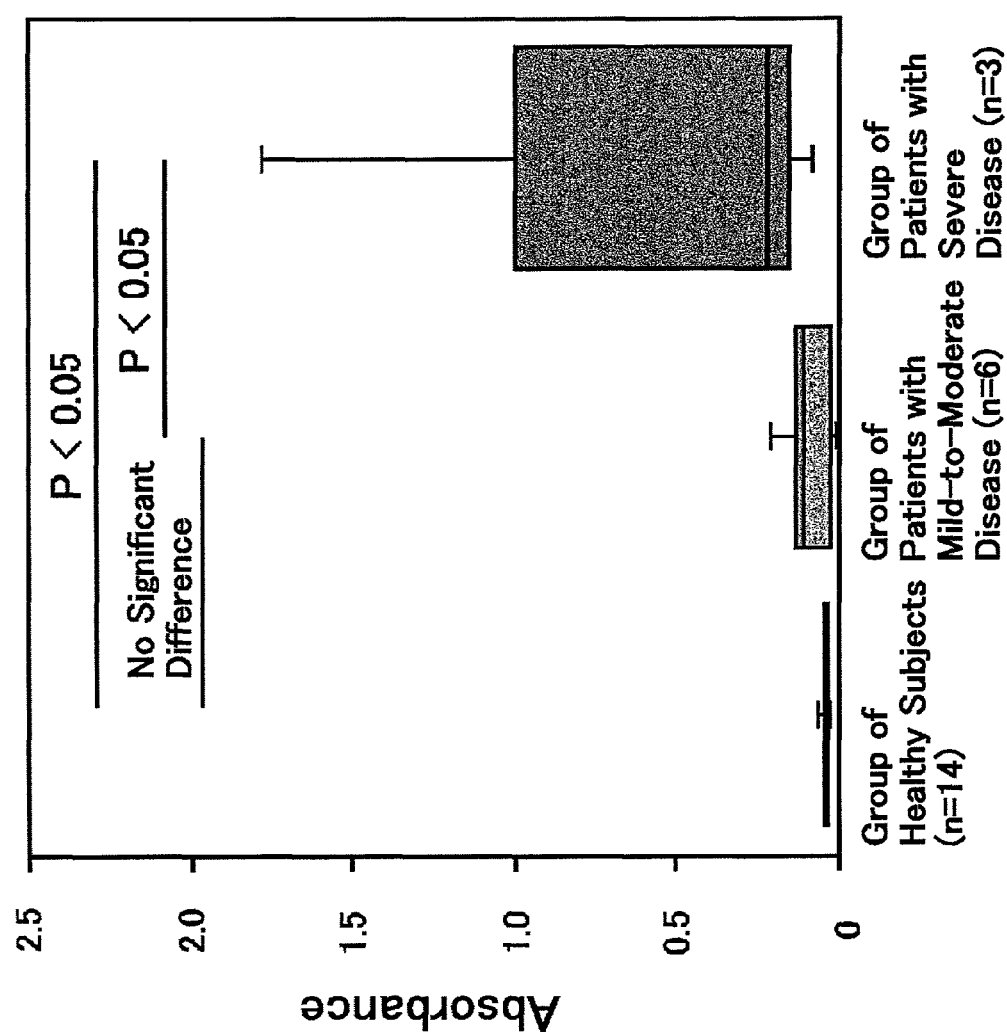
FIG. 10 shows results of ELISA of sera from healthy subjects (n=14), a group of patients with mild-to-moderate disease (n=6), and a group of patients with severe disease (n=3), using an immobilized G11-6 antibody. The results were calculated from the values of the measured absorbance for the group of healthy subjects, the group of patients with mild-to-moderate disease, and the group of patients with severe disease.

As shown in FIG. 9, some sera from patients with liver disease had a band at the α position (corresponding to HDL), and the others did not. Thus, based on this result, patients with liver disease whose serum did not have a band at the α position (corresponding to HDL) at all when compared with that of a healthy subject in an electrophoresis pattern were determined as a group of patients with severe disease. Patients with liver disease whose serum had a band at the α position (corresponding to HDL) were determined as a group of patients with mild-to-moderate disease. Of nine patients with liver disease, six fell under a group of patients with mild-to-moderate disease, and three fell under a group of patients with severe disease.
(2) ELISA with Immobilized G11-6 Antibody An ELISA with an immobilized G11-6 antibody was carried out according to a procedure described in Example 3(2) [2-2]. Here, instead of using the serum samples of Example 3(1), used was a total of 23 samples of this Example (1), including sera from 14 healthy subjects, 6 individuals of a group of patients with mild-to-moderate disease, and 3 individuals of a group of patients with severe disease. Measured values of absorbance were separately tallied for each of a group of healthy subjects, a group of patients with mild-to-moderate disease, and a group of patients with severe disease, and their average was estimated. FIG. 10 shows the results. Each group was compared by one-way analysis of variance and Scheffe's multiple comparison test. If P<0.05, differences were defined as statistically significant.

FIG. 10 demonstrated that the absorbance of a group of healthy subjects was 0.052±0.024; the absorbance of a group of patients with mild-to-moderate disease was 0.105±0.074; and the absorbance of a group of patients with severe disease was 0.699±0.942. The results of the multiple comparison test indicated P<0.05 between a group of patients with severe disease and a group of healthy subjects. Thus, a significant difference was found. In addition, the results indicated P<0.05 between a group of patients with severe disease and a group of patients with mild-to-moderate disease. Thus, a significant difference was found. In contrast, no significant difference was observed between a group of healthy subjects and a group of patients with mild-to-moderate disease.

These results demonstrated that an ELISA with an immobilized G11-6 antibody is useful for severity diagnosis of liver disease in a patient with liver disease.

Example 5

Reactivity Toward Serum from Patient with Dyslipidemia in ELISA with Immobilized G11-6 Antibody (1) Determination of Serum Lipid Components A total of 20 serum samples was collected from 1 healthy subject, 7 patients with dyslipidemia (referred to as dyslipidemia 1, dyslipidemia 2, . . . , and dyslipidemia 7) and 12 patients with liver disease (referred to as liver disease 1, liver disease 2, . . . , and liver disease 12). Serum lipid concentrations were determined using the following reagents and HITACHI Automatic analyzer 7170 (Hitachi High-Technologies Corporation) according to the attached protocol. Next, the measured values were separately tallied for each of a group of healthy subjects, a group of patients with dyslipidemia, and a group of patients with liver disease. Then, their average was estimated. Table 2 shows the results.

- Total cholesterol (TC): Cholestest CHO (Sekisui Medical Co., Ltd.)
- Triglyceride (TG): EXCELIZA TG (Sekisui Medical Co., Ltd.)
- Phospholipid (PL): PureAuto S PL (Sekisui Medical Co., Ltd.)
- Cholesterol in high-density lipoprotein (HDL-C): Cholestest N HDL (Sekisui Medical Co., Ltd.)
- Cholesterol in low-density lipoprotein (LDL-C): Cholestest LDL (Sekisui Medical Co., Ltd.)

those of other dyslipidemia patients, and was the same as or larger than those of liver disease patients 1 to 10 and liver disease patient 12. Meanwhile, it was found that the measured values of the absorbance of liver disease patients 1 to 12 were larger than those of the healthy subject, and was larger than those of the dyslipidemia patients on the whole. These results demonstrated that in an ELISA with an immobilized G11-6 antibody, while a healthy subject had little reactivity, patients with dyslipidemia and patients with liver disease had relatively large reactivity.

Figure 11:
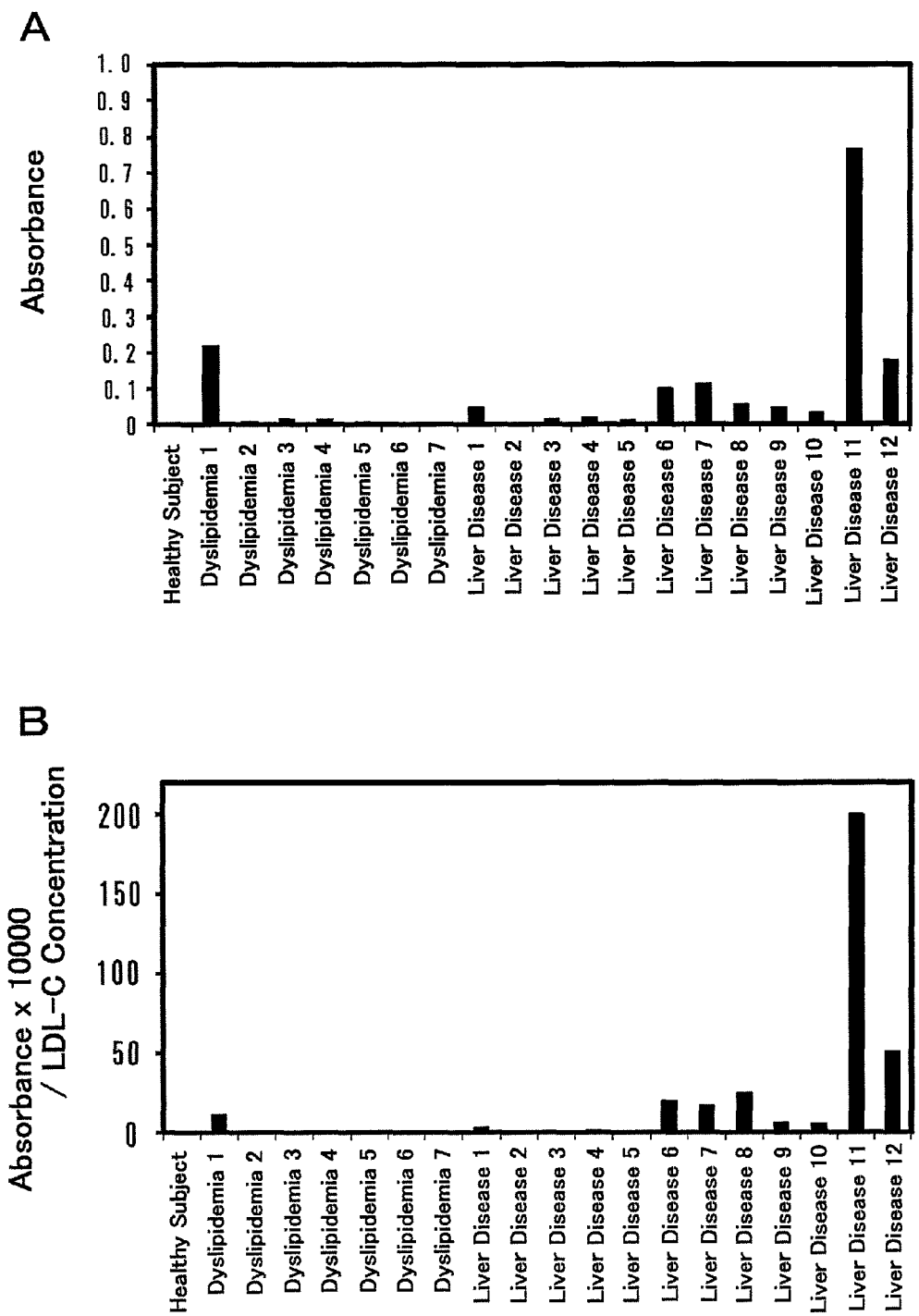
FIG. 11 shows results of ELISA of sera from a healthy subject (n=1), patients with dyslipidemia (n=7), and patients with liver disease (n=12), with an immobilized G11-6 antibody (A); and results as obtained by dividing values of the measured absorbance of each sample by values of the LDL-C concentration in serum of each sample (B).

In addition, as shown in FIG. 11B, the measured value of the absorbance of each sample was divided by the serum LDL-C concentration of each sample. The results demonstrated that a difference between the measured values of the patients with liver disease and those of the healthy subject or the dyslipidemia patients increased. In one hand, the measured values of the patients with liver disease were large. On the other hand, the measured values of the healthy subject and the patients with dyslipidemia decreased. These results demonstrated that when a measured value of absorbance in an ELISA with an immobilized G11-6 antibody was divided by a serum LDL-C concentration, the resulting value increased in a liver-disease-specific manner.

Example 6

Reactivity Toward Gel Filtration Eluates of Serum from Patient with Different Disease in ELISA with Immobilized G11-6 Antibody (1) Reactivity toward Gel Filtration Eluates of Total Lipoprotein Fraction in Various ELISAs Serum was collected from a healthy subject, and was subjected to density gradient centrifugation as previously reported (T. Hirano et al., J. Atherosclerosis and Thrombosis, vol. 12, p. 67-72, 2005) to separate lipoproteins. Specifically, 2 mL of serum from each of a patient with liver disease and a

TABLE 2

|  | Sex (Male:Female) | Age | TC (mg/dL) | TG (mg/dL) | PL (mg/dL) | HDL-C (mg/dL) | LDL-C (mg/dL) |
| --- | --- | --- | --- | --- | --- | --- | --- |
| Healthy Subject | 1:0 | 24 | 196 | 131 | 236 | 60 | 114 |
| Patient with Dyslipidemia | 4:3 | 48.9 ± 16.7 | 285 ± 87 | 541 ± 778 | 315 ± 141 | 44 ± 13 | 153 ± 48 |
| Patient with Liver Disease | 6:6 | 54.8 ± 13.9 | 151 ± 67 | 113 ± 117 | 188 ± 68 | 48 ± 25 | 83 ± 45 |

(2) ELISA with Immobilized G11-6 Antibody

An ELISA with an immobilized G11-6 antibody was carried out according to a procedure described in Example 3(2) [2-2]. Here, instead of using the serum samples of Example 3(1), used was a total of 20 samples of this Example (1), including sera from 1 healthy subject, 7 individuals of a group of patients with dyslipidemia, and 12 individuals of a group of patients with liver disease. FIG. 11A shows the results. In addition, the measured value of absorbance of each sample was divided by the serum LDL-C concentration of each sample that had been determined in this Example (1). FIG. 11B shows the results.

Equation:Measured Value of Absorbance×10000/Serum LDL-C Concentration Determined in This Example  (1)

As shown in FIG. 11A, the absorbance of a healthy subject is almost zero, but the measured values of dyslipidemia patients 1 to 7 were higher than those of the healthy subject on the whole. In particular, it was found that the measured value of the absorbance of dyslipidemia patient 1 was larger than young healthy subject was collected, and was adjusted at a specific gravity, d, of d=1.225 kg/L. The serum was centrifuged with an ultracentrifuge, OptimaMAX ultracentrifuge (Beckman Coulter, Inc.), and a rotor MLN-80 (Beckman Coulter, Inc.) under conditions at 50000 rpm and 15° C. for 20 hours. Then, the upper layer (d<1.225 kg/L) was recovered as a total lipoprotein fraction. Subsequently, gel filtration chromatography was carried out according to a procedure described in Example 1(5) to fractionate 0.5 mL of each eluate. The eluates were designated in sequence as eluate No. 1, eluate No. 2, . . . , and eluate No. 28. With regard to each eluate of eluate Nos. 5, 7, 9, 11, 12, 13, 14, 15, 16, 18, 20, 22, 25, and 28, the TC concentration was then determined using a Cholestest CHO (Sekisui Medical Co., Ltd.) and a HITACHI Automatic analyzer 7170 (Hitachi High-Technologies Corporation) according to the attached protocol.

Following that, each eluate of eluate Nos. 5, 7, 9, 11, 12, 13, 14, 15, 16, 18, 20, 22, 25, and 28 was used as a sample, and an ELISA with an immobilized G11-6 antibody was carried out according to a procedure described in Example 3(2) [2-2]. In addition, each eluate of eluate Nos. 5, 7, 9, 11, 12, 13, 14, 15, 16, 18, 20, 22, 25, and 28 was diluted 10 times with the attached sample diluent. By using these eluates as samples, an ELISA with an immobilized anti-oxidized-phospholipid antibody was carried out according to a procedure described in Example 3(3). Furthermore, each eluate of eluate Nos. 5, 7, 9, 11, 12, 13, 14, 15, 16, 18, 20, 22, 25, and 28 was diluted 500 times with the attached sample diluent. By using these eluates as samples, an ELISA with an immobilized anti-MDA-LDL antibody was carried out according to a procedure described in Example 3(4).

Figure 12:
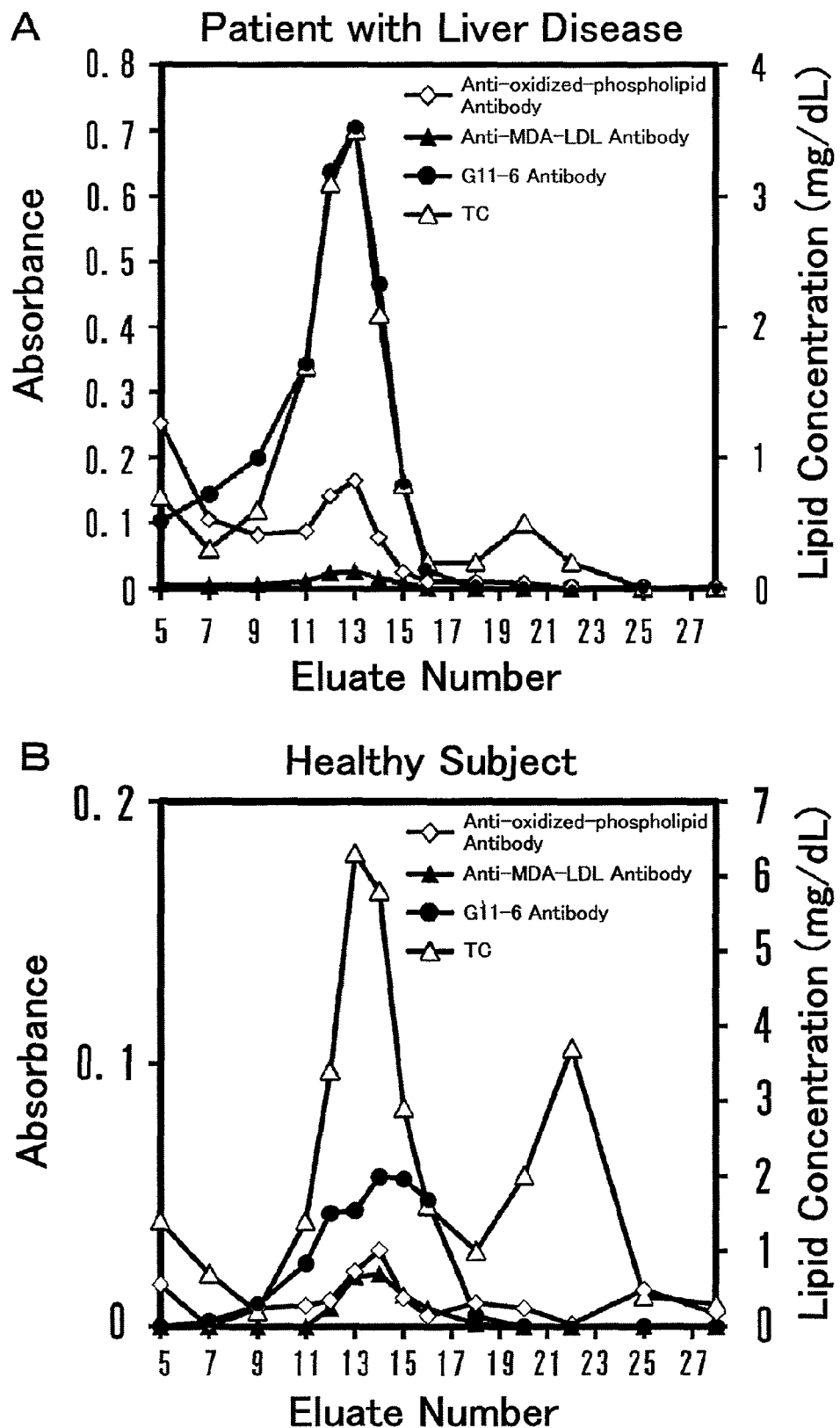
FIG. 12 shows results of the determination of TC concentration in gel filtration eluates of the total lipoprotein from a patient with liver disease, and ELISA of the eluates with an immobilized G11-6 antibody, with an immobilized anti-oxidized-phospholipid antibody, and with an immobilized anti-MDA-LDL antibody (A); and results of determination of the TC concentration in gel filtration eluates of the total lipoprotein from a healthy subject, and ELISA of the eluates with an immobilized G11-6 antibody, with an immobilized anti-oxidized-phospholipid antibody, and with an immobilized anti-MDA-LDL antibody (B).

FIG. 12A shows the results of a TC concentration determination and various ELISAs using serum from a patient with liver disease. FIG. 12B shows the results regarding serum from a healthy subject.

FIG. 12A demonstrated that in a patient with liver disease, eluate No. 13 had a maximum TC concentration. In any of an ELISA with an immobilized G11-6 antibody, an ELISA with an immobilized anti-oxidized-phospholipid antibody, and an ELISA with an immobilized anti-MDA-LDL antibody, the eluate No. 13 also had maximum absorbance.

The TC concentration reflects a concentration of each lipoprotein in a total lipoprotein. Thus, these results verified that the G11-6 antibody specifically reacts with TG-rich LDL present in a patient with liver disease at a high concentration. In addition, the peak of the TC concentration and the peak of reactivity in an ELISA with an immobilized G11-6 antibody were matched with the peaks of reactivity in an ELISA with an immobilized anti-oxidized-phospholipid antibody and an ELISA with an immobilized anti-MDA-LDL antibody, both of which were commercially available ELISAs for oxidized LDL. This result demonstrated that the TG-rich LDL is oxidized LDL and the G11-6 antibody reacts with oxidized LDL.

In contrast, FIG. 12B demonstrated that although in a young healthy subject, elute No. 13 had a maximum TC concentration, elute No. 14 had maximum absorbance in any of an ELISA with an immobilized G11-6 antibody, an ELISA with an immobilized anti-oxidized-phospholipid antibody, and an ELISA with an immobilized anti-MDA-LDL antibody.

These results verified that a healthy subject has oxidized small dense LDL, namely oxidized LDL whose particle size is smaller than that of native-LDL, and that the G11-6 antibody reacts with such oxidized LDL and specifically reacts with the oxidized small dense LDL in a healthy subject.

(2) Reactivity Toward Gel Filtration Eluates of Serum in Various ELISAs

A total of 6 serum samples was collected from each of 1 patient with liver disease, 1 patient with non-alcoholic steatohepatitis (NASH), 2 patients with dyslipidemia (referred to as dyslipidemia 1 and dyslipidemia 2), and 2 healthy subjects (referred to as healthy subject 1 and healthy subject 2). Gel filtration chromatography was carried out according to a procedure described in Example 1(5) to fractionate 0.5 mL of each eluate. The eluates were designated in sequence as eluate No. 1, eluate No. 2, . . . , and eluate No. 28. With regard to each eluate of eluate Nos. 1 to 28, the TC, TG, and PL concentrations were then determined according to a procedure described in Example 5(1).

Following that, each eluate of eluate Nos. 1, 3, 5, 8, 10, 11, 12, 13, 14, 15, 16, 18, 21, 24, and 28 was used as a sample, and an ELISA with an immobilized G11-6 antibody was carried out according to a procedure described in Example 3(2) [2-2]. Each eluate of eluate Nos. 1, 3, 5, 8, 10, 11, 12, 13, 14, 15, 16, 18, and 24 was diluted 500 times with the attached sample diluent. By using these eluates as samples, an ELISA with an immobilized anti-MDA-LDL antibody was carried out according to a procedure described in Example 3(4).

Figure 13:
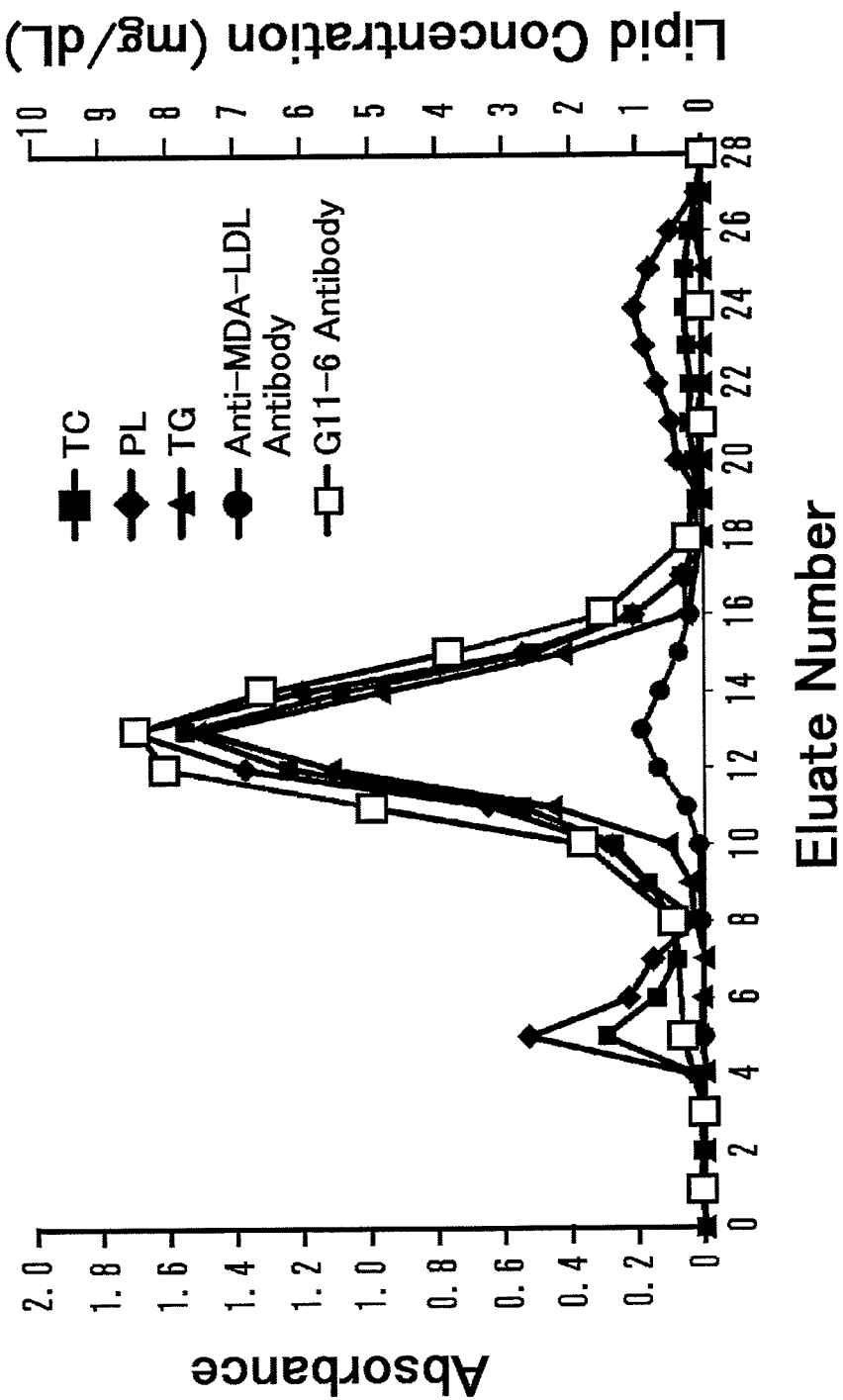
FIG. 13 shows results of the determination of TC concentration, TG concentration, and PL concentration in gel filtration eluates of serum from a patient with liver disease (n=1), and ELISA of the eluates with an immobilized G11-6 antibody, and with an immobilized anti-MDA-LDL antibody.
Figure 14:
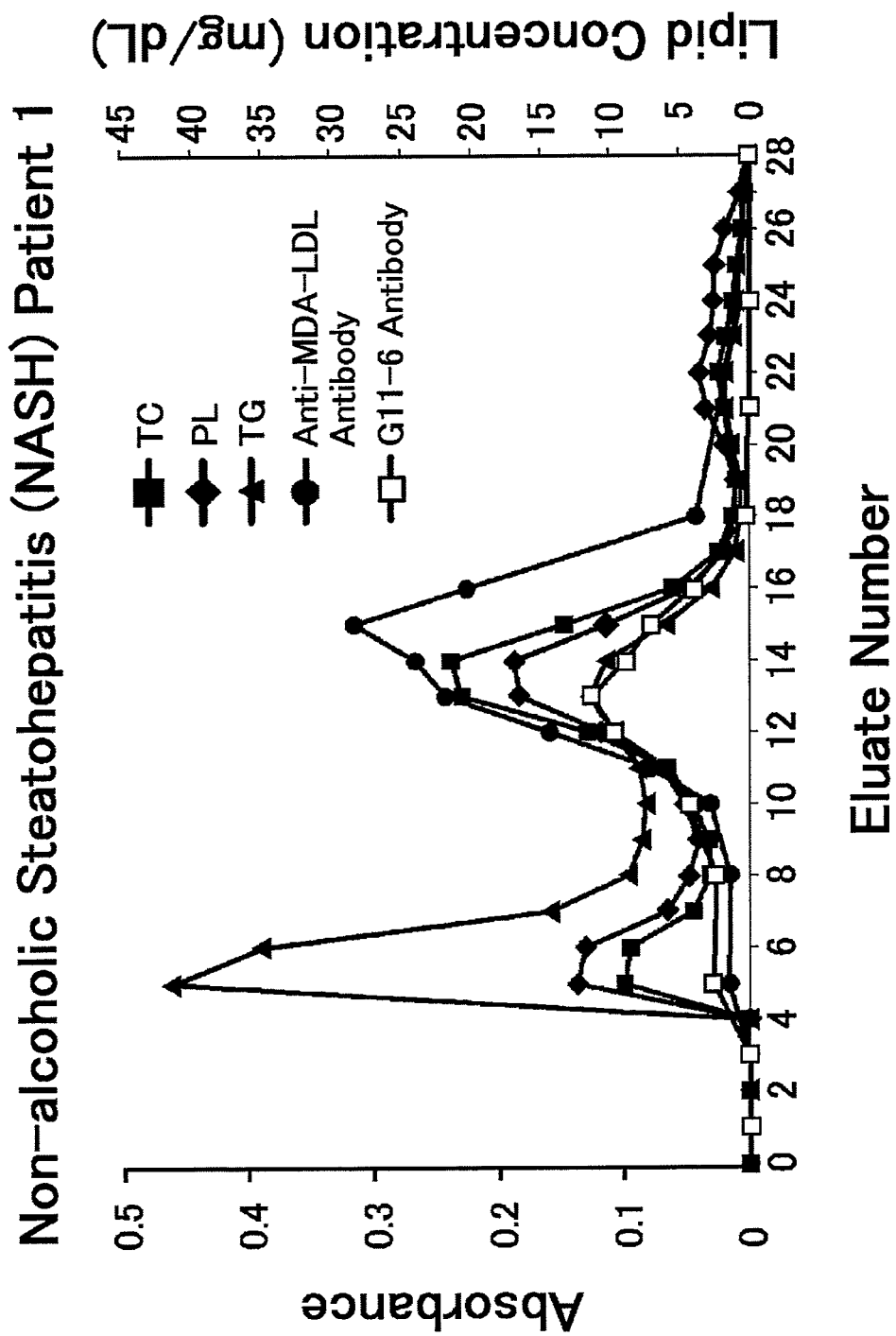
FIG. 14 shows results of the determination of TC concentration, TG concentration, and PL concentration in gel filtration eluates of serum from a patient with NASH (n=1), and ELISA of eluates with an immobilized G11-6 antibody, and with an immobilized anti-MDA-LDL antibody.
Figure 16:
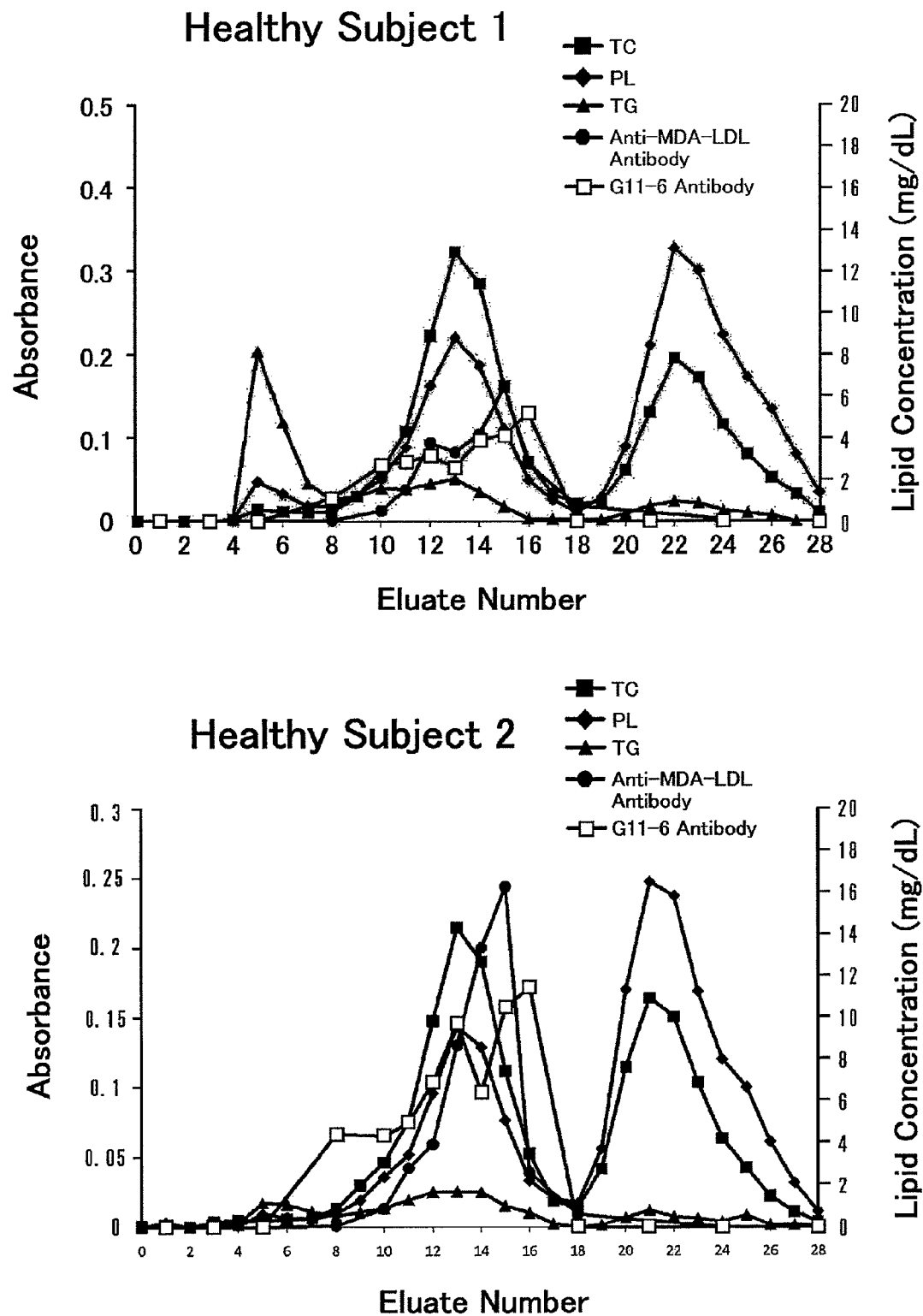
FIG. 16 shows results of the determination of TC concentration, TG concentration, and PL concentration in gel filtration eluates of sera from healthy subjects (n=2), and ELISA of the eluates with an immobilized G11-6 antibody, and with an immobilized anti-MDA-LDL antibody.

FIG. 13 shows the results regarding lipid concentration determinations and various ELISAs using serum from a patient with liver disease (n=1). FIG. 14 shows the results using serum from a patient with NASH (n=1). FIG. 15 shows the results using sera from patients with dyslipidemia (n=2). FIG. 16 shows the results using sera from healthy subjects (n=2).

FIG. 13 demonstrated that in a patient with liver disease, eluate No. 13 had maximum TC, TG, and PL concentrations, and had maximum absorbance in any of an ELISA with an immobilized G11-6 antibody and an ELISA with an immobilized anti-MDA-LDL antibody.

These results provided results similar to those of FIG. 12A in this Example (1), and verified that the G11-6 antibody specifically reacts with TG-rich LDL; the TG-rich LDL is oxidized LDL; and the G11-6 antibody reacts with the oxidized LDL.

In addition, FIG. 14 demonstrated that in a patient with NASH, eluate No. 14 had maximum TC and PL concentrations; eluate No. 5 had a maximum TG concentration; eluate No. 13 had maximum absorbance in an ELISA with an immobilized G11-6 antibody; and eluate No. 15 had maximum absorbance in an ELISA with an immobilized anti-MDA-LDL antibody.

These results verified that a patient with NASH has oxidized LDL whose particle size is similar to that of native-LDL, and that the G11-6 antibody reacts with such oxidized LDL and specifically reacts with the oxidized LDL whose particle size is similar to that of native-LDL in a patient with NASH. In addition, the anti-MDA-LDL antibody highly reacted with oxidized small dense LDL, namely oxidized LDL whose particle size was smaller than that of native-LDL. The G11-6 antibody, however, reacted little with oxidized small dense LDL. The present inventors believed that this was because the oxidized small dense LDL in a patient with NASH was highly oxidized as described in the following Examples.

In addition, FIG. 15 demonstrated that in a patient with dyslipidemia, eluate No. 13 had maximum TC, TG, and PL concentrations; eluate No. 11 had maximum absorbance in an ELISA with an immobilized G11-6 antibody; and eluate No. 14 or 15 had maximum absorbance in an ELISA with an immobilized anti-MDA-LDL antibody.

These results verified that a patient with dyslipidemia has oxidized remnant lipoprotein, namely oxidized LDL whose particle size is larger than that of native-LDL, and that the G11-6 antibody reacts with such oxidized LDL and specifically reacts with the oxidized remnant lipoprotein in a patient with dyslipidemia. In contrast, the anti-MDA-LDL antibody was demonstrated to react little with the oxidized remnant lipoprotein. In addition, in a manner similar to the case of using serum from a patient with NASH, when serum from a patient with dyslipidemia was used, the anti-MDA-LDL antibody highly reacted with oxidized small dense LDL, namely oxidized LDL whose particle size was smaller than that of native-LDL. The G11-6 antibody, however, reacted little with oxidized small dense LDL. The present inventors believed that this was because the oxidized small dense LDL in a patient with dyslipidemia was highly oxidized as described in the following Examples.

In addition, FIG. 16 demonstrated that in healthy subjects, eluate No. 13 had maximum TC and PL concentrations; eluate No. 13 or 5 had a maximum TG concentration; eluate No. 16 had maximum absorbance in an ELISA with an immobilized G11-6 antibody; and eluate No. 15 had maximum absorbance in an ELISA with an immobilized anti-MDA-LDL antibody.

These results provided results similar to those of FIG. 12B in this Example (1). These results confirmed that a healthy subject has oxidized small dense LDL, namely oxidized LDL whose particle size is smaller than that of native-LDL, and that the G11-6 antibody reacts with such oxidized LDL and specifically reacts with the oxidized small dense LDL in a healthy subject.

In addition, the results shown in FIGS. 13 to 16 demonstrated that even when eluates were obtained by directly subjecting serum to gel filtration chromatography without separation of a total lipoprotein fraction by density gradient centrifugation, an ELISA with an immobilized G11-6 antibody exhibited enough sensitivity to specifically detect oxidized LDL.

Example 7

Figure 17:
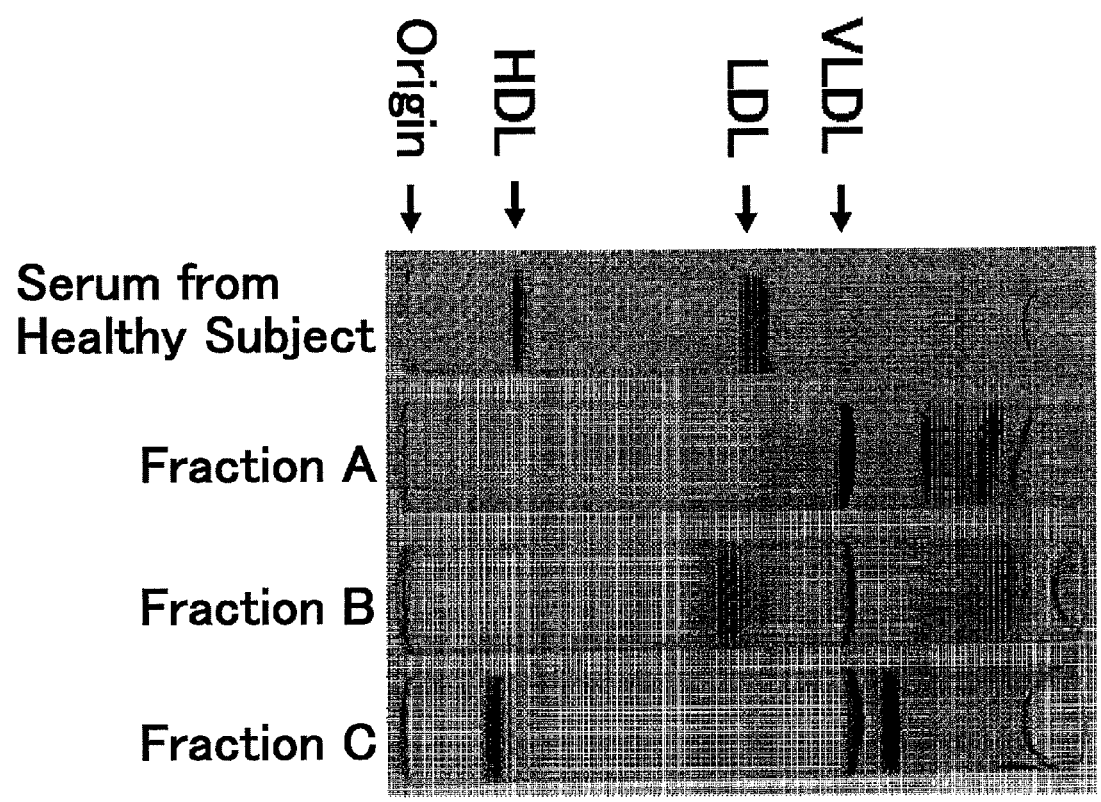
FIG. 17 shows a result of polyacrylamide gel electrophoresis of A, B, and C fractions as obtained by carrying out density gradient centrifugation of serum from a healthy subject.

Reactivity Toward Metal-Oxidized LDL in ELISA with Immobilized G11-6 Antibody (1) Preparation of Native-LDL Fractions
[1-1] Separation of Lipoprotein by Density Gradient Centrifugation Serum was collected from a healthy subject, and was subjected to density gradient centrifugation as previously reported (T. Hirano et al., J. Atherosclerosis and Thrombosis, vol. 12, p. 67-72, 2005) to separate lipoproteins. Specifically, 2 mL of serum from a healthy subject was prepared at a specific gravity, d, of d=1.019 kg/L, and was centrifuged with a ultracentrifuge, OptimaMAX ultracentrifuge (Beckman Coulter, Inc.), and a rotor MLN-80 (Beckman Coulter, Inc.) under conditions at 40000 rpm and 15° C. for 20 hours. Then, the upper layer (d<1.019 kg/L) was recovered as A fraction. Subsequently, the lower layer was prepared at a specific gravity, d, of d=1.063 kg/L, and was centrifuged with the above ultracentrifuge and rotor under conditions at 50000 rpm and 15° C. for 18 hours. The resulting upper layer (1.019 kg/L<d<1.063 kg/L) was collected as B fraction, and the lower layer was collected as C fraction.
[1-2] Examination of Lipoproteins by Polyacrylamide Gel Electrophoresis Serum from a healthy subject, A fraction, B fraction, and C fraction of this Example (1) [1-1] were subjected to polyacrylamide gel electrophoresis by using a commercially available lipoprotein analysis kit (Lipophor; Jokoh, Inc.) according to the attached protocol. FIG. 17 shows the results.

As shown in FIG. 17, B fraction differed from A fraction and C fraction, and failed to contain HDL but did contain LDL. Hence, the B fraction was employed as a native-LDL solution.
[1-3] Determination of Protein Concentration in the Native-LDL Solution The B fraction of this Example (1) [1-1], that is, a native-LDL solution, was dialyzed against PBS as a dialysis solution at 4° C. overnight. Then, the protein concentration was determined by a procedure described in Example 1(2) [2-4], and the fraction was diluted with PBS at 0.5 mg/mL.
(2) Preparation of Metal-Oxidized LDL The following concentrations and amounts of copper sulfate were added to 120 μL of the native-LDL solution (0.5 mg/mL) of this Example (1) [1-3], and the mixtures were incubated at 37° C. for 0.5, 1, 2, 4, 8, and 24 hours to prepare metal-oxidized LDL solutions with different degrees of oxidation as follows.

<a->1.6 μL of 250 μmol/L copper sulfate, no dialysis, and use immediately after oxidation treatment.
<a-1>1.6 μL of 250 μmol/L copper sulfate, no dialysis, and storage at 4° C. for 24 hours.
<a-1w>1.6 μL of 250 μmol/L copper sulfate, no dialysis, and storage at 4° C. for 1 week.
<a+1>1.6 μL of 250 μmol/L copper sulfate, dialysis, and overnight dialysis at 4° C.
<a+1w>1.6 μL of 250 μmol/L copper sulfate, dialysis, and after overnight dialysis at 4° C., storage at 4° C. for 6 days.
<b->1.6 μL of 500 μmol/L copper sulfate, no dialysis, and use immediately after oxidation treatment.
<c->6.0 μL of 500 μmol/L copper sulfate, no dialysis, and use immediately after oxidation treatment.
<d->6.0 μL of 1000 μmol/L copper sulfate, no dialysis, and use immediately after oxidation treatment.

Figure 18:
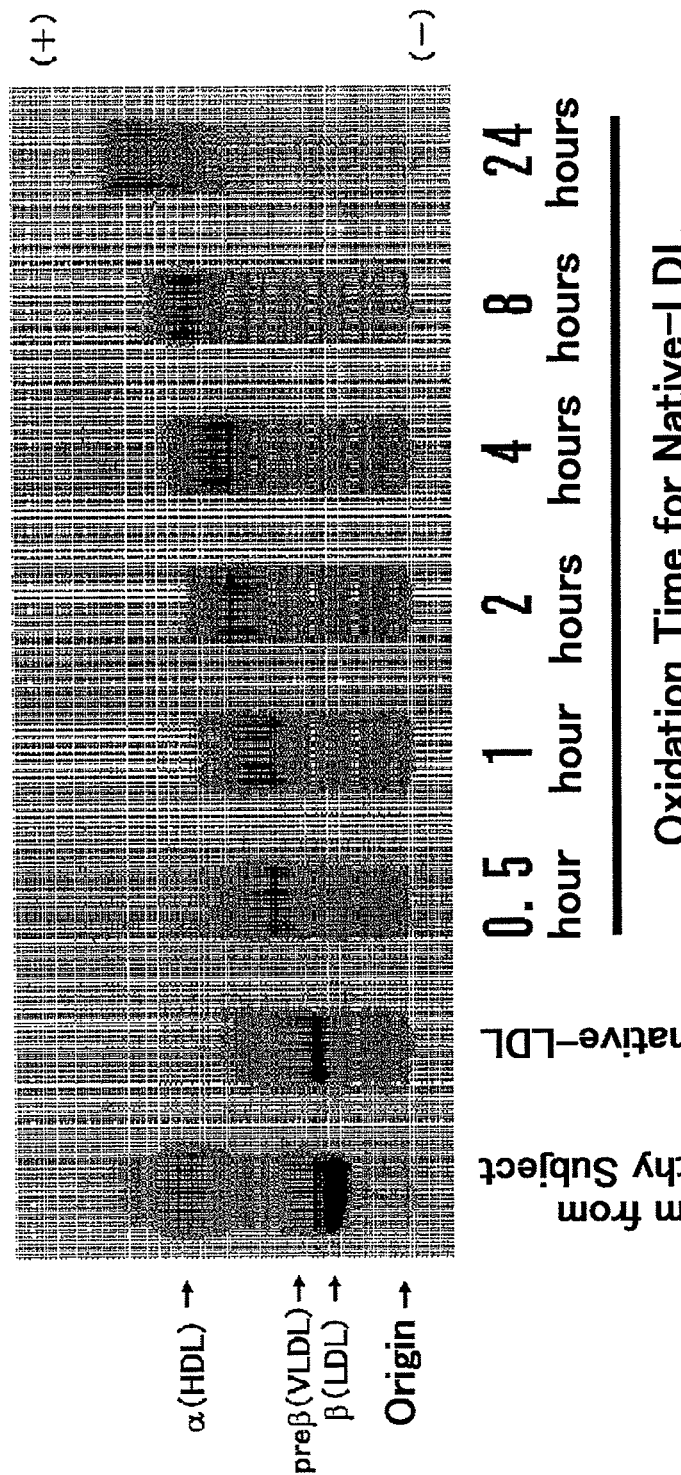
FIG. 18 shows a result of agarose gel electrophoresis of solutions containing the metal-oxidized LDLs produced by oxidization of Native-LDL with varying oxidation time.

The above samples <a->, <b->, <c->, and <d-> were used immediately after incubation for the respective set periods. The above <a-1> was incubated for the respective set periods, stored at 4° C. for 24 hours, and then used. The above <a-1w> was incubated for the respective set periods, stored at 4° C. for 1 week, and then used. The above <a+1> was incubated for the respective set periods, dialyzed against PBS as a dialysis solution at 4° C. overnight, and then used. The above <a+1w> was incubated for the respective set periods, dialyzed against PBS as a dialysis solution at 4° C. overnight, stored at 4° C. for 6 days, and then used.
(3) Examination of Degree of Oxidation of Metal-Oxidized LDL The metal-oxidized LDL solution of the sample <a+1> of this Example (2) was subjected to agarose gel electrophoresis according to a procedure described in Example 1(1). FIG. 18 shows the results.

As shown in FIG. 18, bands of metal-oxidized LDL were detected at a position located closer to the anode side than that of native-LDL. In addition, the migration distance to the anode side increased and was proportional to the incubation time after the addition of copper sulfate. This result demonstrated that the native-LDL oxidation proceeded as the incubation time after the addition of copper sulfate was proportional to the distance.
(4) Reactivity Toward Metal-Oxidized LDL in ELISA with Immobilized G11-6 Antibody (Comparison on Additive Amount of Copper Sulfate)

Figure 19:
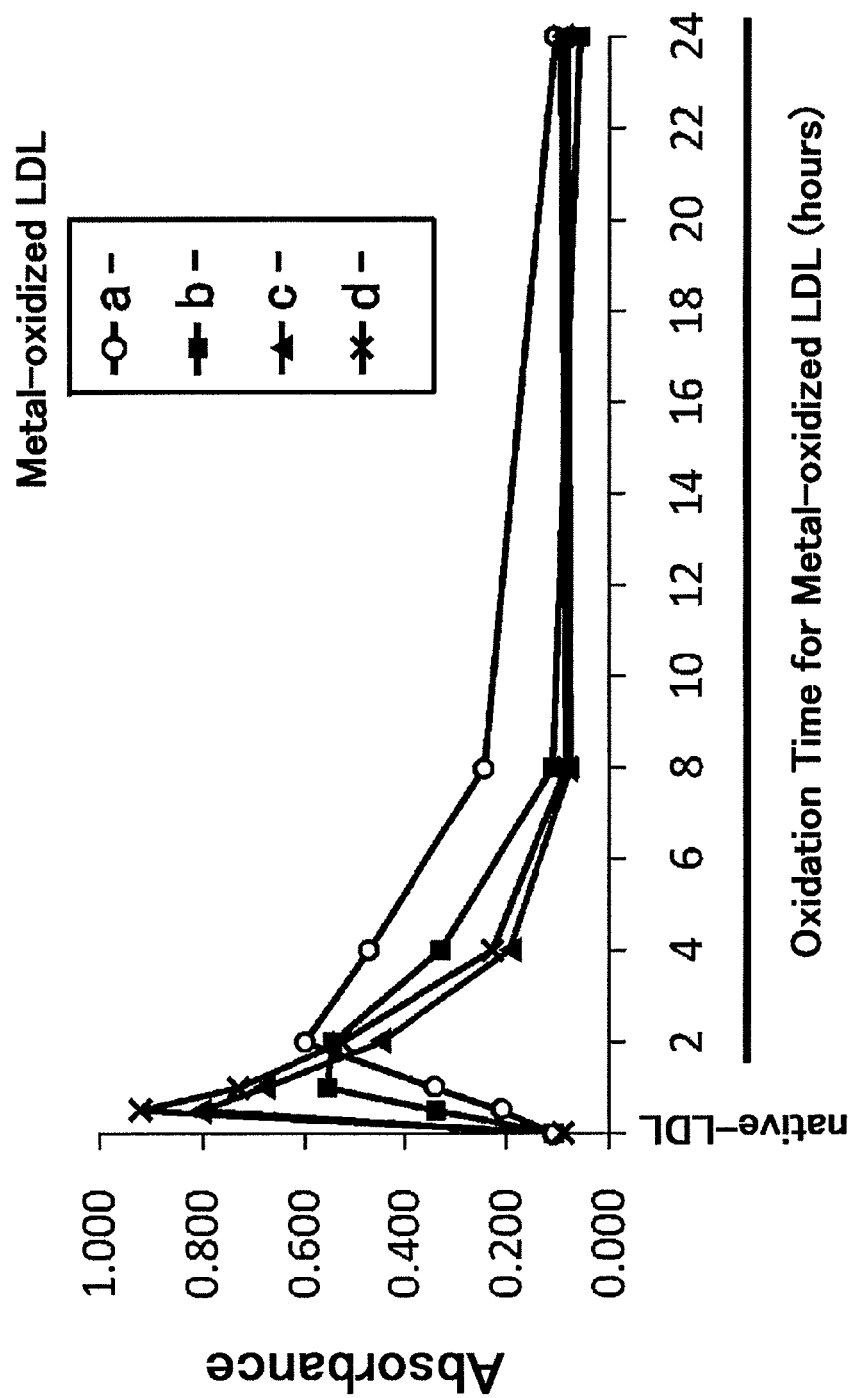
FIG. 19 shows results of ELISA with an immobilized G11-6 antibody on metal-oxidized LDLs <a–>, <b–>, <c–>, and <d–>. The ordinate represents absorbance in the ELISA. The abscissa represents the oxidation time of the metal-oxidized LDLs used as ELISA samples.

An ELISA with an immobilized G11-6 antibody was carried out according to a procedure described in Example 3(2) [2-2]. Instead of using the serum sample of Example 3(1), the metal-oxidized LDL of each of the samples <a->, <b->, <c->, and <d-> was used. FIG. 19 shows the results.

FIG. 19 demonstrated that in <a->, the absorbance increased until 2 hours of oxidation time, but the absorbance decreased at or after 4 hours of oxidation time. Then, the absorbance was equivalent to that of native-LDL at 24 hours of oxidation time. In <b->, the absorbance increased until 1 hour of oxidation time, but the absorbance decreased at or after 2 hours of oxidation time. Then, the absorbance was equivalent to that of native-LDL at or after 8 hours of oxidation time. In <c-> and <d->, the absorbance became maximum at 0.5 hour of oxidation time. The absorbance decreased at or after 1 hour of oxidation time. Then, the absorbance was equivalent to that of native-LDL at or after 8 hours of oxidation time.

These results demonstrated that an ELISA with an immobilized G11-6 antibody exhibited higher reactivity toward slightly oxidized LDL, and exhibited a little reactivity toward unoxidized native-LDL and highly oxidized LDL.

Figure 20:
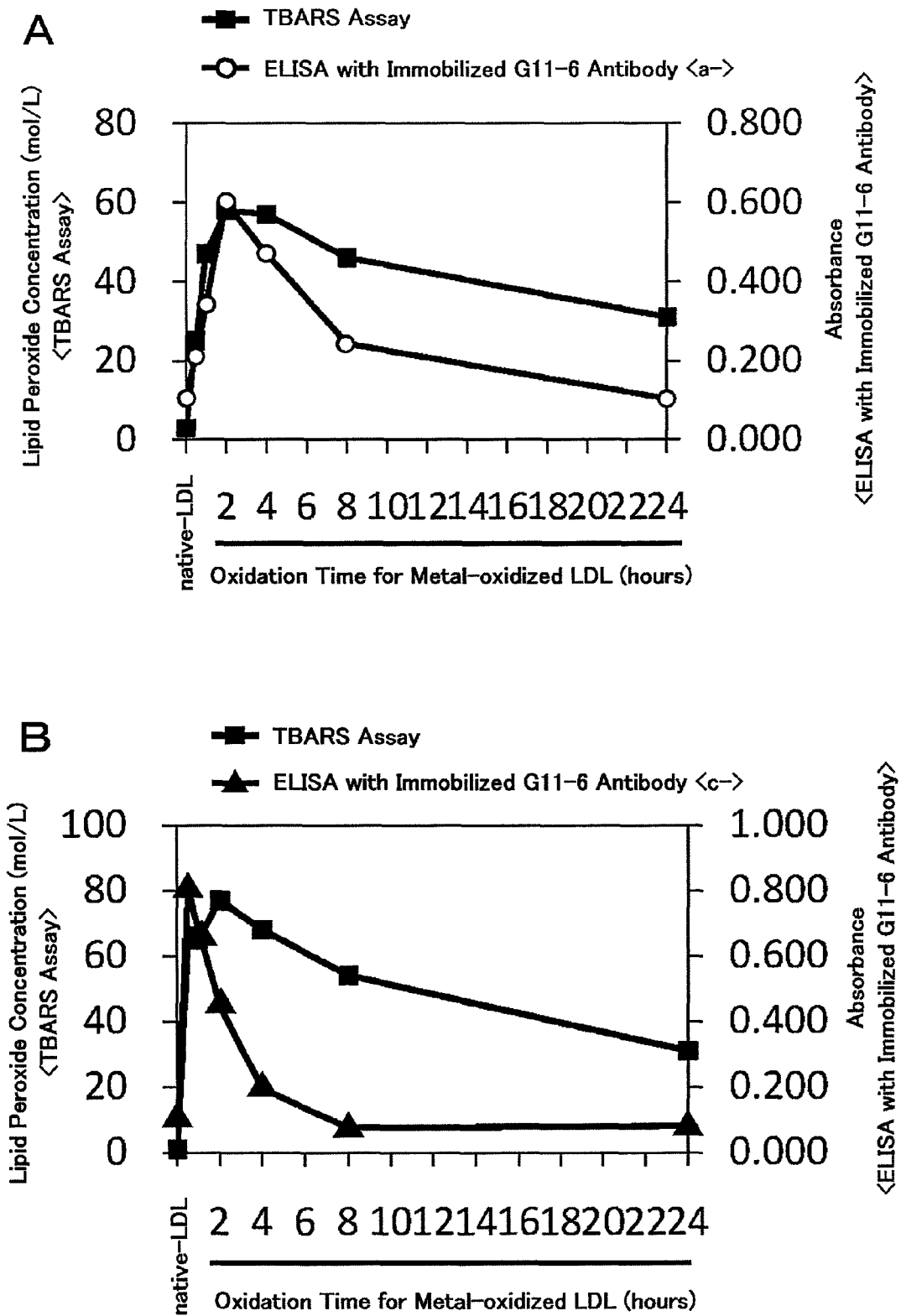
FIG. 20 shows results of the determination of lipid peroxide concentration in metal-oxidized LDL <a–> by TBARS assay and ELISA thereof with an immobilized G11-6 antibody (A: the ordinate represents absorbance of the ELISA and the lipid peroxide concentration; the abscissa represents the oxidation time of metal-oxidized LDL used as an ELISA and TBARS sample); and results of the determination of lipid peroxide concentration in metal-oxidized LDL <c–> by a TBARS assay, and ELISA thereof with an immobilized G11-6 antibody (B: the ordinate represents absorbance of the ELISA and the lipid peroxide concentration; the abscissa represents the oxidation time of metal-oxidized LDL used as an ELISA and TBARS sample).

(5) Determination of Lipid Peroxide Concentration of Metal-Oxidized LDL by TBARS Assay With regard to metal-oxidized LDL of <a–> and <c–> in this Example (2), the lipid peroxide concentration was determined using a TBARS assay kit (Cayman Chemical Company) according to the attached protocol. Specifically, an equivalent amount of acetic acid was mixed with sodium hydroxide. Thiobarbituric acid was added at 36.8 mmol/L. The mixture was dissolved to prepare a coloring reagent. Next, 1 mL of the coloring reagent and 25 μL of an SDS solution were each added to 25 μL of the metal-oxidized LDL solution of each of <a–> and <c–> in this Example (2), and mixed and incubated at 100° C. for 1 hour. Then, the mixture was placed on ice for 1 minute to stop the reaction. Subsequently, the mixture was centrifuged under conditions at room temperature and 12000 rpm for 10 minutes. After that, the supernatant was collected and dispensed in a 96-well microplate (Sumitomo Bakelite Co., Ltd.) at 150 μL/well. Finally, the absorbance at a wavelength of 550 nm was read with a microplate reader (Model680; Bio-Rad Laboratories, Inc.). FIG. 20A shows the results regarding <a–> together with the results regarding <a–> of this Example (4). FIG. 20B shows the results regarding <c–> together with the results regarding <c–> of this Example (4).

As shown in FIGS. 20A and 20B, a similar change in the lipid peroxide concentration was detected in the samples <a–> and <c–>. That is, in either case, the lipid peroxide concentration increased until the oxidation time passed 2 hours. After the oxidation time had passed 4 hours, the lipid peroxide concentration moderately decreased. In contrast, in an ELISA with an immobilized G11-6 antibody, a distinct change in absorbance was detected between the samples <a–> and <c–>. Specifically, in the case of <a–>, the absorbance increased until the oxidation time passed 2 hours, and the absorbance rapidly decreased after the oxidation time had passed 4 hours. At 24 hours of oxidation time, the absorbance was equivalent to that of native-LDL. In the case of <c–>, at 0.5 hour of oxidation time, the absorbance became maximum. After the oxidation time had passed 1 hour, the absorbance rapidly decreased. Then, at 8 hours of oxidation time, the absorbance was equivalent to that of native-LDL.

These results demonstrated that an ELISA with an immobilized G11-6 antibody exhibited higher reactivity toward slightly oxidized LDL, but exhibited a little reactivity toward highly oxidized LDL. In contrast, thiobarbituric acid was found to have similar reactivity toward any of slightly oxidized LDL and highly oxidized LDL.

(6) Reactivity Toward Metal-Oxidized LDL in ELISA with Immobilized G11-6 Antibody (Comparison on Storage of Metal-Oxidized LDL for 24 Hours and the Presence or Absence of Dialysis Treatment)

Figure 21:
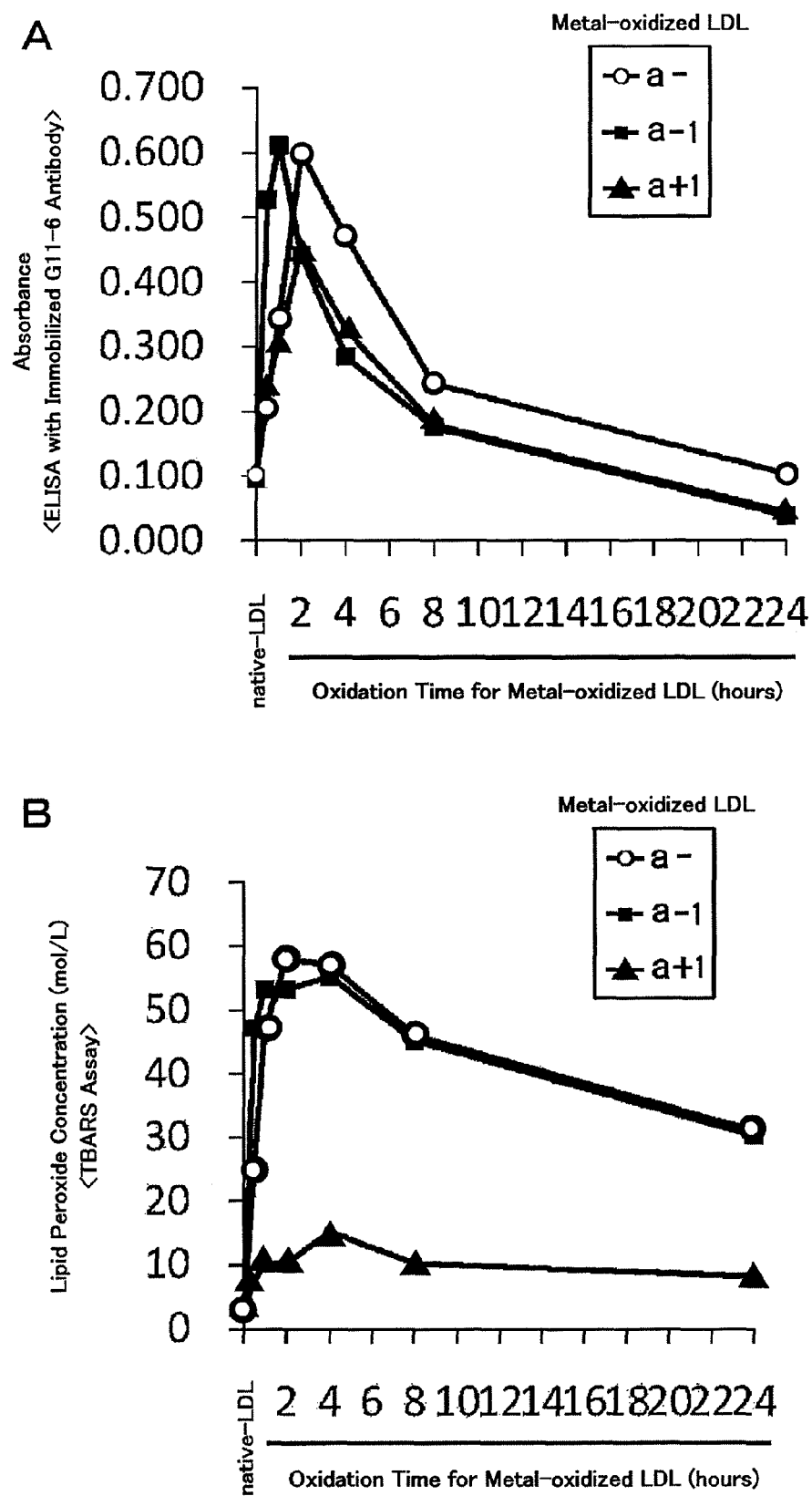
FIG. 21 shows results of ELISA of metal-oxidized LDLs <a–>, <a–1>, and <a+1> with an immobilized G11-6 antibody (A: the ordinate represents absorbance of the ELISAs; the abscissa represents the oxidation time of metal-oxidized LDLs used as ELISA samples); and results of the determination of lipid peroxide concentration in metal-oxidized LDLs <a–>, <a–1>, and <a+1> by a TBARS assay (B: the ordinate represents the lipid peroxide concentration; the abscissa represents the oxidation time of metal-oxidized LDLs used as TBARS samples).

An ELISA with an immobilized G11-6 antibody was carried out according to a procedure described in Example 3(2) [2-2]. Instead of using the serum samples of Example 3(1), the metal-oxidized LDL of each of the samples <a–1> and <a+1> of this Example (2) was used. FIG. 21A shows the results together with the results regarding <a–> of this Example (4).

In addition, with regard to the metal-oxidized LDL of <a–1> and <a+1> of this Example (2), the lipid peroxide concentration was determined by a procedure described in this Example (5). FIG. 21B shows the results together with the results regarding <a–> of this Example (5).

FIG. 21A demonstrated that in an ELISA with an immobilized G11-6 antibody, the absorbance of <a–1> increased until the oxidation time passed 1 hour. After the oxidation time had passed 2 hours, the absorbance decreased. Then, at 16 hours of oxidation time, the absorbance was equivalent to that of native-LDL. In addition, in the case of <a+1>, the absorbance increased until the oxidation time passed 2 hours. After the oxidation time had passed 4 hours, the absorbance was reduced. Then, at about 16 hours of oxidation time, the absorbance was equivalent to that of native-LDL.

These results demonstrated that in an ELISA with an immobilized G11-6 antibody, the maximum absorbance was observed for the metal-oxidized LDL that had undergone a shorter oxidation time in the case of <a–1> than <a–> and <a+1>. This revealed that the oxidation of the metal-oxidized LDL proceeded during storage at 4° C. In addition, the absorbance of <a+1> was the almost same value as or a somewhat lower value than that of <a–>. This demonstrated that an antigen against G11-6 antibody in the metal-oxidized LDL was not a substance that was removed by dialysis. In addition, when the oxidation time passed 2 hours, the absorbance of <a–1> and <a+1> was somewhat lower than that of <a–>. This demonstrated that after the oxidation time had passed 2 hours, the metal-oxidized LDL had decreased reactivity toward the G11-6 antibody due to its storage at 4° C. for 24 hours regardless of the presence or absence of dialysis treatment.

Meanwhile, FIG. 21B demonstrated that in the case of <a–1>, the lipid peroxide concentration increased until the oxidation time passed 4 hours, and after the oxidation time had passed 8 hours, the concentration moderately decreased. In contrast, the lipid peroxide concentration of <a+1> markedly decreased regardless of the oxidation time, compared with that of <a–> and <a–1>.

These results demonstrated that a change in the lipid peroxide concentration is similar between <a–1> and <a–>. Thus, the storage at 4° C. failed to cause a change in the lipid peroxide concentration which exerted reactivity toward thiobarbituric acid. In addition, a thiobarbituric acid reactive substance in the metal-oxidized LDL was found to be a substance capable of being removed by dialysis.

(7) Reactivity Toward Metal-Oxidized LDL in ELISA with Immobilized G11-6 Antibody (Comparison on Storage of Metal-Oxidized LDL for 1 Week and the Presence or Absence of Dialysis Treatment)

Figure 22:
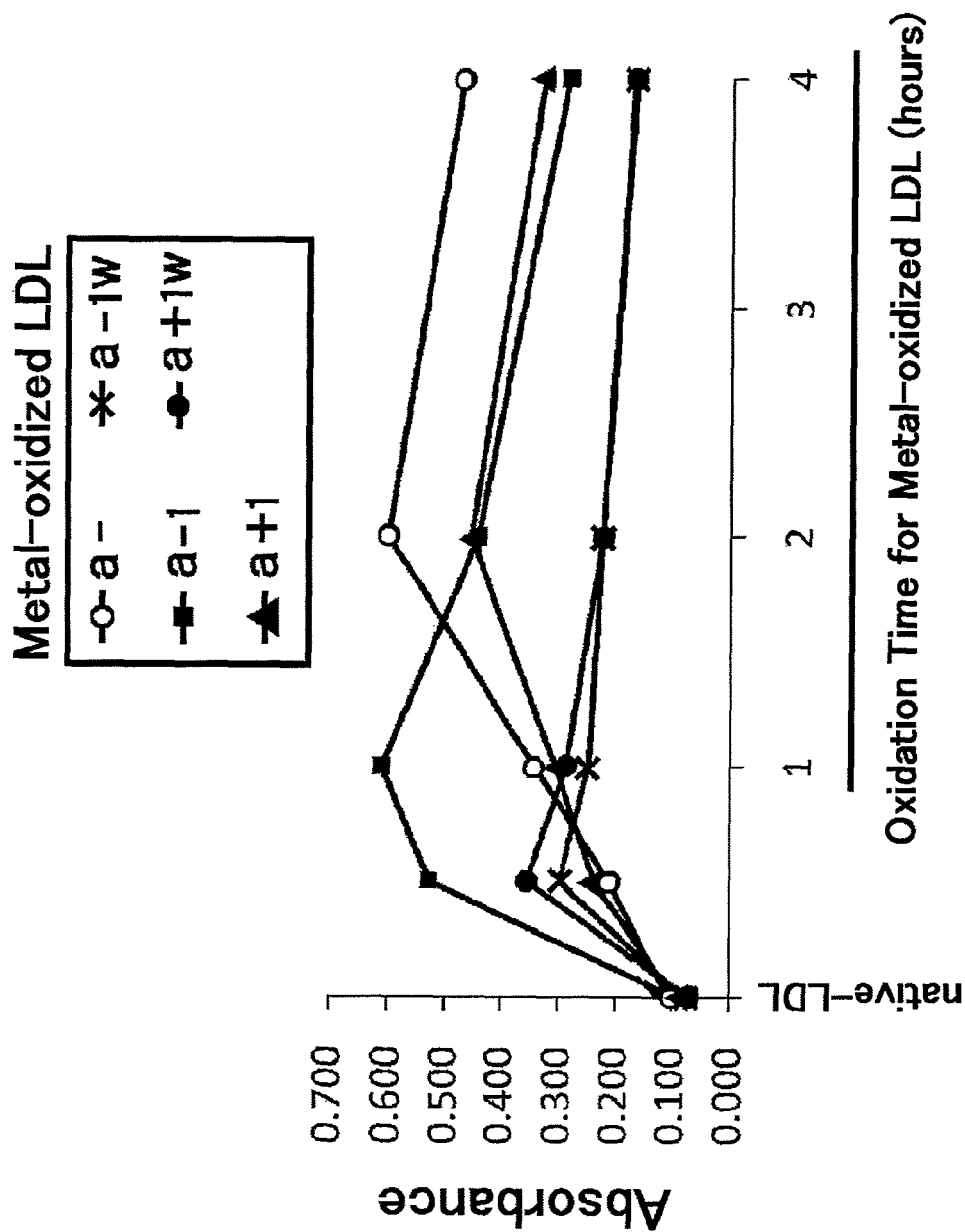
FIG. 22 shows results of ELISA of metal-oxidized LDLs <a–>, <a–1>, <a+1>, <a–1w>, and <a+1w> with an immobilized G11-6 antibody. The ordinate represents absorbance of the ELISA. The abscissa represents the oxidation time of the metal-oxidized LDLs used as ELISA samples.

An ELISA with an immobilized G11-6 antibody was carried out according to a procedure described in Example 3(2) [2-2]. Instead of using the serum samples of Example 3(1), used was the metal-oxidized LDL of each of the samples <a–1w> and <a+1w> of this Example (2), whose incubation time after the addition of copper sulfate was 0.5, 1, 2, or 4 hours. FIG. 22 shows the results together with the results regarding the ELISA with an immobilized G11-6 antibody of this Example (6).

As shown in FIG. 22, a similar change in absorbance between <a–1w> and <a+1w> was detected. In either case, at 0.5 hour of oxidation time, the absorbance became maximum. After the oxidation time had passed 1 hour, the absorbance decreased. In addition, <a–1w> and <a+1w> exhibited lower absorbance than <a–>, <a–1>, and <a+1> after the oxidation time had passed 1 hour.

These results demonstrated that after the oxidation time had passed 1 hour, the metal-oxidized LDL had decreased reactivity toward the G11-6 antibody due to its storage at 4° C. for 1 week regardless of the presence or absence of dialysis treatment.

Example 8

Reactivity Toward Metal-Oxidized LDL in ELISA with Immobilized G11-6 Antibody (Comparison on Reactivity in Various ELISAs with Different Antibody)

(1) Preparation of Metal-Oxidized LDL

Cooper sulfate was added at 3.33 μmol/L to 120 μL of the native-LDL solution (0.5 mg/mL) of Example 7(1) [1-3], and the mixture was incubated at 37° C. for 0.5, 1, 2, 3, 4, 6, 8, and 24 hours to prepare metal-oxidized LDL solutions with different degrees of oxidation. The metal-oxidized LDL solutions prepared were immediately used as ELISA samples.

(2) Various ELISAs for Metal-Oxidized LDL

The metal-oxidized LDL as prepared in this Example (1) was used as a sample, and an ELISA with an immobilized G11-6 antibody was carried out according to a procedure described in Example 3(2) [2-2]. The attached sample diluent was used to dilute the metal-oxidized LDL as prepared in this Example (1) by 2500 times. By using them as samples, an ELISA with an immobilize anti-oxidized-phospholipid antibody was carried out according to a procedure described in Example 3(3). The attached sample diluent was used to dilute the metal-oxidized LDL as prepared in this Example (1) by 1000 times. By using them as samples, an ELISA with an immobilized anti-MDA-LDL antibody was carried out according to a procedure described in Example 3(4).

In addition, in order to check the state of apolipoprotein B in the metal-oxidized LDL at the respective oxidation times, a sandwich ELISA was performed which had an anti-apolipoprotein B antibody as a solid-phase antibody and had an anti-apolipoprotein B antibody as a detection antibody. Specifically, the ELISA was carried out according to a procedure described in Example 3(2) [2-2]. Instead of using 5 μg/mL of the G11-6 antibody of Example 1(5), 10 μg/mL of a goat anti-apolipoprotein B polyclonal antibody of Example 3(2) <2-1-2> was used. Also, instead of using the serum samples that had been diluted 20 times of Example 3(1), used was the metal-oxidized LDL that had been diluted at 0.1 μg/mL as prepared in this Example (1). In addition, instead of using ALP-SA (Zymed Laboratories, Inc.) that had been diluted 250 times, used was ALP-SA (Zymed Laboratories, Inc.) that had been diluted 500 times.

(3) Determination of Lipid Peroxide Concentration in Metal-Oxidized LDL by TBARS Assay The lipid peroxide concentration in the metal-oxidized LDL as prepared in this Example (1) was determined by a TBARS assay according to a procedure described in Example 7(5).

(4) Determination of Conjugated Diene in Metal-Oxidized LDL

In order to be used as an index for lipid oxidation, the conjugated diene in the metal-oxidized LDL at each oxidation time was determined. Specifically, PBS was used to dilute the metal-oxidized LDL as prepared in this Example (1) at 0.04 mg/mL, and the absorbance at a wavelength of 234 nm was read with a spectrophotometer (V-530; JASCO Corporation).

Figure 23:
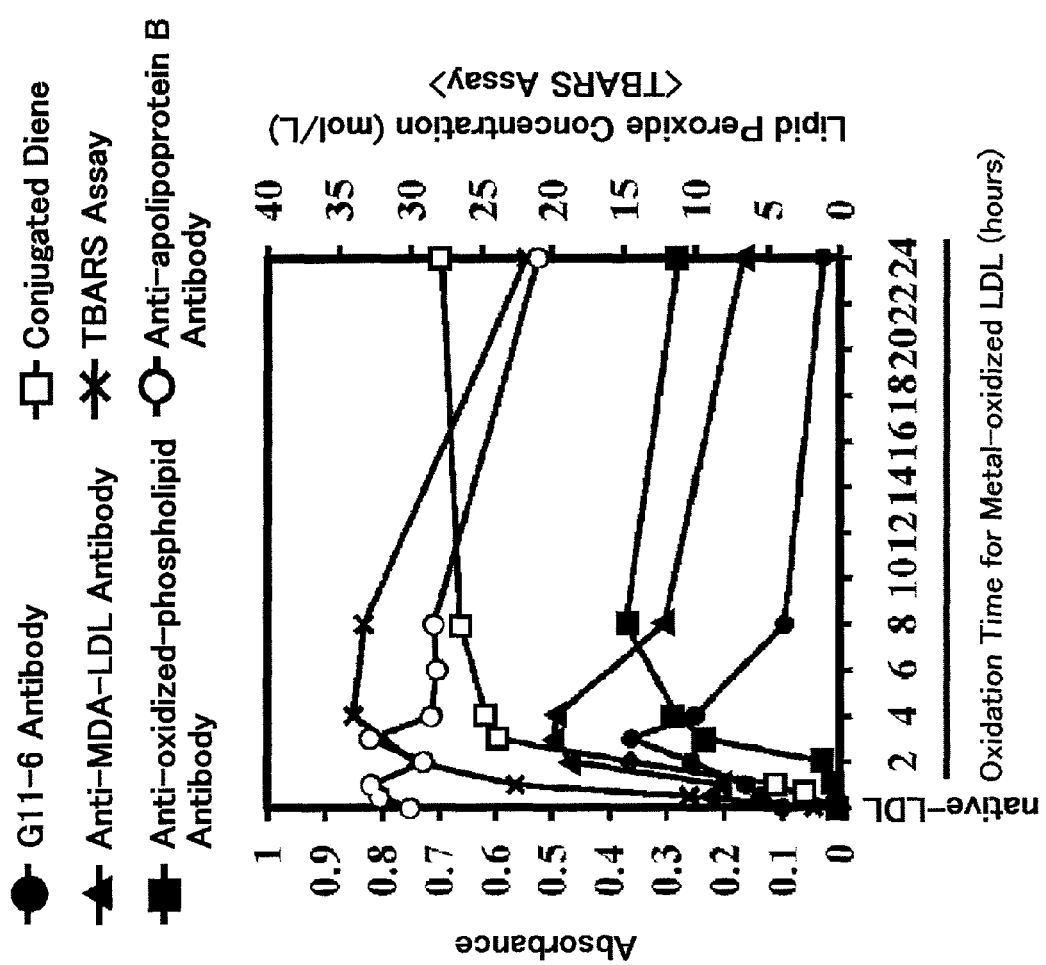
FIG. 23 shows results of ELISA of metal-oxidized LDL with an immobilized G11-6 antibody, with an immobilized anti-oxidized-phospholipid antibody, with an immobilized anti-MDA-LDL antibody, and with an immobilized anti-apolipoprotein B antibody, and the determination of lipid peroxide concentration by a TBARS assay, and of conjugated diene in the metal-oxidized LDL. The ordinate represents absorbance of the ELISA and the conjugated diene determination. The abscissa represents the oxidation time of the metal-oxidized LDL used as a sample.

FIG. 23 shows the results of these Examples (2), (3), and (4). FIG. 23 demonstrated that in an ELISA with an immobilized G11-6 antibody, the absorbance increased until the oxidation time passed 3 hours. After the oxidation time had passed 4 hours, the absorbance decreased. Then, at 8 hours of oxidation time, the absorbance was equivalent to that of native-LDL. At 24 hours of oxidation time, the absorbance was lower than that before oxidation. Meanwhile, in an ELISA with an immobilized anti-oxidized-phospholipid antibody, the absorbance increased until the oxidation time passed 8 hours. At 24 hours of oxidation time, the absorbance slightly decreased. In an ELISA with an immobilized anti-MDA-LDL antibody, the absorbance increased until the oxidation time passed 3 hours. After the oxidation time had passed 4 hours, the absorbance decreased. At 24 hours of oxidation time, the absorbance was equivalent to that of native-LDL. In an ELISA with anti-apolipoprotein B antibodies as a solid-phase antibody and a detection antibody, the absorbance was high until the oxidation time passed 8 hours. At 24 hours of oxidation time, the absorbance slightly decreased. According to a TBARS assay, the lipid peroxide concentration increased until the oxidation time passed 4 hours. After the oxidation time had passed 8 hours, the absorbance slightly decreased. When the conjugated diene was determined, the absorbance steeply increased until the oxidation time passed 3 hours. After the oxidation time had passed 4 hours, the absorbance gradually increased along the oxidation time.

These results verified that an ELISA with an immobilized G11-6 antibody exhibited higher reactivity toward slightly oxidized LDL, but exhibited a little reactivity toward unoxidized native-LDL and highly oxidized LDL. In addition, a change in absorbance in an ELISA with an immobilized G11-6 antibody differed from any of a change in absorbance in an ELISA with an immobilized anti-MDA-LDL antibody and an ELISA with an immobilized anti-oxidized-phospholipid antibody. Thus, the G11-6 antibody was demonstrated to recognize, as an antigen, a site distinct from a site recognized by the anti-MDA-LDL antibody or the anti-oxidized-phospholipid antibody in the oxidized LDL. Furthermore, it was demonstrated that the site recognized as an antigen by the G11-6 antibody correlated with neither apolipoprotein B nor the lipid peroxide concentration that exerted reactivity toward thiobarbituric acid and conjugated diene.

The invention claimed is:

1. A monoclonal antibody comprising a heavy chain variable region comprising the amino acid sequence set forth in SEQ ID NO: 10 and a light chain variable region, wherein the heavy chain variable region comprises, in the order from its N-terminus, the amino acid sequence set forth in SEQ ID NO: 8, the amino acid sequence set forth in SEQ ID NO: 9, and the amino acid sequence set forth in SEQ ID NO: 10; and wherein the light chain variable region comprises, in the order from its N-terminus, the amino acid sequence set forth in SEQ ID NO: 13, the amino acid sequence set forth in SEQ ID NO: 14, and the amino acid sequence set forth in SEQ ID NO: 15.

2. The monoclonal antibody of claim 1, wherein the heavy chain variable region consists of the amino acid sequence set forth in SEQ ID NO: 7.

3. The monoclonal antibody according to claim 1, further comprising a light chain variable region consisting of the amino acid sequence set forth in SEQ ID NO: 12.

4. A monoclonal antibody which is produced from a hybridoma deposited under accession number NITE BP-916.

5. The monoclonal antibody according to claim 1, wherein a degree of reactivity between the monoclonal antibody and an antigen set forth in (b) is smaller than a degree of reactivity between the monoclonal antibody and an antigen set forth in (a) in an ELISA (Enzyme-linked immunosorbent assay) using the monoclonal antibody as a solid-phase antibody and an anti-apolipoprotein B antibody as a detection antibody:
  (a) a metal-oxidized low-density lipoprotein as obtained by reacting a native low-density lipoprotein (native-LDL) at a final concentration of 0.493 g/L with copper sulfate at a final concentration of 3.29 μmol/L at 37° C. for 0.5 hour; and
  (b) a metal-oxidized low-density lipoprotein as obtained by reacting the native low-density lipoprotein (native-LDL) at a final concentration of 0.493 g/L with copper sulfate at a final concentration of 3.29 μmol/L at 37° C. for 24 hours.

6. The monoclonal antibody according to claim 1, wherein a degree of reactivity between the monoclonal antibody and an antigen set forth in (b) is smaller than a degree of reactivity between the monoclonal antibody and an antigen set forth in (a) in an ELISA Enzyme-linked immunosorbent assay) using the monoclonal antibody as a solid-phase antibody and an anti-apolipoprotein B antibody as a detection antibody:
  (a) an oxidized remnant lipoprotein as collected from a patient with dyslipidemia; and
  (b) a native low-density lipoprotein (native-LDL) as collected from said patient with dyslipidemia.

7. The monoclonal antibody according to claim 2, further comprising a light chain variable region consisting of the amino acid sequence set forth in SEQ ID NO: 12.

8. The monoclonal antibody according to claim 1, wherein the monoclonal antibody reacts specifically with an oxidized low density lipoprotein.

9. The monoclonal antibody according to claim 7, wherein the monoclonal antibody reacts specifically with an oxidized low density lipoprotein.

* * * * *